(12) United States Patent
Altieri

(10) Patent No.: US 6,238,875 B1
(45) Date of Patent: May 29, 2001

(54) DIAGNOSTIC METHODS USEFUL IN THE CHARACTERIZATION OF LYMPHOPROLIFERATIVE DISEASE CHARACTERIZED BY INCREASED EPR-1

(75) Inventor: Dario C. Altieri, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 08/189,309

(22) Filed: Jan. 28, 1994

Related U.S. Application Data

(63) Continuation-in-part of application No. 07/988,897, filed on Dec. 10, 1992, now abandoned, which is a continuation of application No. 07/667,957, filed on Mar. 12, 1991, now abandoned.

(51) Int. Cl.$^7$ .................. G01N 33/53; G01N 33/536; G01N 33/574; G01N 33/563

(52) U.S. Cl. .................. 435/7.23; 435/7.1; 435/7.2; 435/7.92; 435/7.93; 435/7.94; 435/7.95; 435/7.21; 436/512; 436/536; 436/518; 436/538; 436/813

(58) Field of Search .................. 424/155.1, 153.1; 435/7, 7.1, 7.21, 7.23, 7.2, 7.92, 7.93, 7.94, 7.95, 240.27; 436/512, 536, 518, 538, 813; 530/387.1, 387.7, 388.22, 388.25, 388.73, 388.75, 388.7, 388.8, 388.85, 389.3, 389.6, 389.7, 391.3, 809, 866

(56) References Cited

FOREIGN PATENT DOCUMENTS

9216558 * 10/1992 (WO).

OTHER PUBLICATIONS

Altieri, et al., "Regulated CA$^{2+}$ Signalling Through Leukocyte CD11b/CD18 Integrin", *Biochem, J.* 288: 465–473 (1992).
Worfolk, et al., "Factor Xa Interacts With Two Sites on Monocytes With Different Functional Activities", *Blood 80*: 1989–1997 (1992).
Bar–Shavit, et al., "Chemotactic Response of Monocytes to Thrombin", *J. Cell. Biol. 96*: 282–285 (1983).
Schwartz, "Costimulation of T Lymphocytes: The Role of CD28, CTLA–4, and B7/BB1 in Interleukin–2 Production and Immunotherapy", *Cell 71*: 1065–1068 (1992).
Stubbs, et al., "cDNA Cloning of a Mouse Mammary Epithelial Cell Surface Protein Reveals the Existence of Epidermal Growth Factor–Like Domains Linked to Factor VIII–Like Sequences", *PNAS USA 87*: 8417–8421 (1990).
Weber, et al., "Activation Through CD3 Molecule Leads to Clonal Expansion of all Human Peripheral Blood T Lymphocytes: Functional Analysis of Clonally Expanded Cells", *J. Immunol. 135*: 2337–2342 (1985).

Geppert, et al., "Accessory Cell Independent Proliferation of Human T4 Cells Stimulated By Immobilized Monoclonal Antibodies to CD3", *J. Immunol. 138*: 1660–1666 (1987).
Chan, et al., "New Insights Into T–Cell Antigen Receptor Structure and Signal Transduction", *Curr. Opin. Immunol. 4*: 246–251 (1992).
Janeway, "The T Cell Receptor as a Multicomponent Signalling Machine: CD4/CD8 Coreceptors and CD45 in T Cell Activation", *Ann. Rev. Immunol. 10*: 645–674 (1992).
Lefranc, et al., "Two Tandemly Organized Human Genes Encoding the T–Cell γ Constant–Region Sequences Show Multiple Rearrangement in Different T–Cell Types", *Nature 316*: 464–466 (1985).
Brenner, et al., "Two Forms of the T–Cell Receptor γ Protein Found on Peripheral Blood Cytotoxic T Lymphocytes", *Nature 325*: 689–694 (1987).
Miles, L.A., et al., Fibrinolysis 2: 61 (1988).
Morrissey, et al., Cell 50: 129 (1987).
Nesheim, M. E., et al., J. Biol. Chem. 254: 10952 (1979).
Chen, L. B., et al., PNAS USA 72: 131 (1975).
Glenn, K.C., et al., Nature 278: 711 (1979).
Baker, J. B., et al., Nature 278: 743 (1979).
Unkeless, J. C., et al., J. Exp. Med. 137: 85 (1973).
Sullivan, L. M., et al., Cell 45: 905 (1986).
Boyle, M.D.P., et al., J. Immunol. 139: 169 (1987).
Bar–Shavit, R., et al., Science 220: 728 (1983).
Redelman, D., et al., J. Immunol. 124: 870 (1980).
Chang, T. W., et al., J. Immunol. 124: 1028 (1980).
Suffys, P., et al., Eur. J. Biochem. 178: 257 (1988).
Scuderi, P., J. Immunol. 143: 168 (1989).

(List continued on next page.)

*Primary Examiner*—Ronald B. Schwadron
(74) *Attorney, Agent, or Firm*—Emily Holmes; Thomas Fitting

(57) ABSTRACT

A new class of cellular receptors extensively homologous but not identical to coagulation factors V and VIII is identified. These new cell surface receptors are designated effector cell protease receptors (EPRs) and include EPR-1, which is shown to bind protease ligands. The DNA and amino acid residue sequences of the receptor are also described. The invention also discloses methods, sequences and vectors useful in the purification and synthesis of cellular receptors of the present invention.

Antibody compositions capable of immunoreacting with the receptor or with polypeptides containing the identified amino acid residue sequences and related therapeutic and diagnostic protocols are also described, as are polypeptides, compositions and methods relating to the inhibition of T lymphocyte proliferation using the antibodies disclosed herein. The receptors are also demonstrated to bind coagulation factor Xa, which binding is inhibited by various disclosed monoclonal antibodies to the receptors. The present invention also discloses polypeptides, antibodies and compositions capable of stimulating or co-stimulating lymphocyte proliferation.

14 Claims, 17 Drawing Sheets

OTHER PUBLICATIONS

Masson, D., et al., Cell 49: 679 (1987).
Jenne, D., et al., PNAS USA 85: 4814 (1988).
Masson, D., et al., J. Biol. Chem. 260: 9069 (1985).
Pasternack, M. S., et al., Nature 322: 740.12 (1986).
Podack, E. R., et al., J. Exp. Med. 160: 695 (1984).
Gershenfeld, H. K., et al., Science 232: 854 (1986).
Jenne, D., et al., J. Immunol. 140: 318 (1988).
Lobe, C. G., et al., Science 232: 858 (1986).
Gershenfeld, H. K., et al., PNAS USA 85: 1184 (1988).
Duke, R. C., et al., J. Exp. Med. 170: 1451 (1989).
Dennert, G., et al., PNAS USA 84: 5004 (1987).
Altieri, et al., J. Biol. Chem. 264 (5): 2969 (1989).
Altieri, et al., J. Immunol. 145: 246 (1990).
Cornelissen, et al., Nucl. Acids Res. 14: 2157–2169 (1986).
McGeoch, et al., J. Gen. Virol. 69: 1531–1574 (1988).
Sibold, et al., Mol. Gen. Genetics 214: 439–450 (1988).
Gerard, Meth. Enzymol. 182: 529–539 (1990).
Ostrove, Meth. Enzymol. 182: 357–379 (1990).
Lewin, Genes, John Wiley & Sons, N.Y., 1987, p. 104.
De la Hera et al., Eur. J. Immunol., 18:1131–1134, 1988.*
Mitus et al., Chapter 30, From: "Clinical Oncology", Ed. Holleb et al., American Cancer Society, 1991, pp. 426–429.*
ATCC Catalogue of Cell Lines and Hybridomas, 7th Ed., American Type Culture Collection, 1992, p. 297.*
Seaver, Gen. Eng. News, 14: 10,21, 1994.*
Sambrook et al., "Molecular Cloning: A Lab Manual", Cold Spring Harbor, 1984, pp. 8.3, 8.11–8.22, 8.46–8.51, 10.2–10.12 and 11.5–11.12.*
Matsudaira, Methods in Enzymology, vol. 182, pp. 602–614, 1990.*

* cited by examiner

```
AAATGACAGGCTTTTATTTCTCAGGAGATGACCTCCAGAGGTTTCCAGGAAGCTGTAACAAT         72
                 MetThrSerArgGlyPheGlnArgSerCysAsnAsn                  12

CCACCCTGCAGCTTCTATGACAGGGAGGAGGGCGAATCAAATCCATCATCTTAGCCAGACTTCAGCCTGCG 144
ProProCysSerSerMetThrGlyArgArgAlaAsnGlnIleHisLeuThrProAspPheSerLeuArg    36

GAGCTGCTGCCTCCAAAGAAAGCGGGGACCTGGTCTCTCCCCCGTGTGGAGAACTGACAGA          216
GluLeuLeuProProLysLysAlaGlyThrTrpAlaAspCysValSerProProCysGlyGluArgAspArg 60

TGTGAAGGTTGGGCTGACAGACACACCTGCAGCAGCCCAGCCACCTGCCAAGTCCACACTCAGGAC    288
CysGluGlyTrpAlaAspArgHisThrAlaCysSerSerProAlaSerThrCysGlnValHisThrGlnAsp 84

TGTGACAGCCTCAACAACATGAGGTCCAGACACATTCACTGTGGAAGGCTCTGCCACGCGAACAAAGCTGTC 360
CysAspSerLeuAsnAsnMetArgSerArgHisIleHisCysGlyArgLeuCysHisAlaAsnLysAlaVal 108

AGCTCTAGCAAAAGGGACACTGCCTTCTTCCCTCACTTGTAAGCCCGGAATCAAAACAGC          432
SerSerLysArgAspThrAlaPhePheLeuProHisPheSerProGlyLysProGlyAsnGlnAsnSer   132

AAAAATGAGCCCCAAAAAGAGAGAGAGAAGCAGCAGCAGCCACTGTTACCCAGCAGCACCCGCTGCACAG 504
LysAsnGluProProLysLysArgGluArgSerSerHisCysTyrProAlaAlaProAlaAlaGln      156

GCAGAAGCACCTCGGTGCCACTTTCAAGACAAAACAAGAGCAGTTGAAACATCTAATTGAAAATGTTG  576
AlaGluAlaProLeuValProLeuSerArgGlnAsnLysSerThrValGluThrSerAsnLeuLysMetLeu 180
```

FIG.IA

```
ATCTCCTTTCCTAAGACATTGCTAAGGGGCCTAAGGGCTGGTGGCACCAGGAATAAACCCTGGAAGT    648
IleSerPheProLysThrLeuLeuArgGlyProGlnGluGlyTrpTrpHisGlnGlyIleAsnProGlySer    204

GGTGCAGCCACTCTGGGACCAGGACCTCCAATCCATCGAGGCCCTGCTCGATGGCACGG    720
GlyAlaAlaThrLeuGlyProGlySerSerGluArgProGlnSerIleGluAlaSerCysSerMetAlaArg    228

CGCACTTCTTGCGAGTTCCTCAAATTTCTTCTTATTGTTGGTTTCCTTTGCAATTTGTTCTTGGCT    792
ArgThrPhePheAlaValSerSerAsnSerPheLeuLeuLeuValSerPheAlaIleLeuPheLeuAla    252

CTTTCTCTGTCCAGTTTCAAAAATTCACCAAGGGTTAATTCTTCAAACTGCTTCTTGACAGAAAGGAAAGCG    864
LeuSerLeuSerPheLysAsnSerProArgValAsnSerAsnCysPheLeuThrGluArgLysAla    276

CAACCGGACGAATGCTTTTATGTTCCTCTATGGGTCGTCATCTGGCTCCCAGCCTTCCAGCTCCTTGAAG    936
GlnProAspGluCysPheLeuCysSerSerMetGlySerSerGlySerGlnProSerSerLeuLys    300

CAGAAGAAACACTGGGCCAAGTCTCGGCTCGTTTCCTCAGTGGGCAGTGGATGAAGCCAGCCATCCGC    1008
GlnLysLysHisTrpAlaLysSerGlySerPheSerValGlyGlnTrpMetLysProAlaSerAlaIleArg    324

TCCGGGGTGCAGGCGCAGCCCTCCAAGAAGGCCAGTTCTTGAATGTAGAGAGATGCGGTGTCCTTGAGAAAGG    1080
SerGlyValGlnArgSerProProArgArgAlaSerEnd    337

GCTGCCAGGCAGGGGCAACGTCGGGCACCCATGCCGCCACTTCTGCCAACGGGTCCGGCGATTC    1152
AAATCTGAGACAG    1165
```

FIG.1B

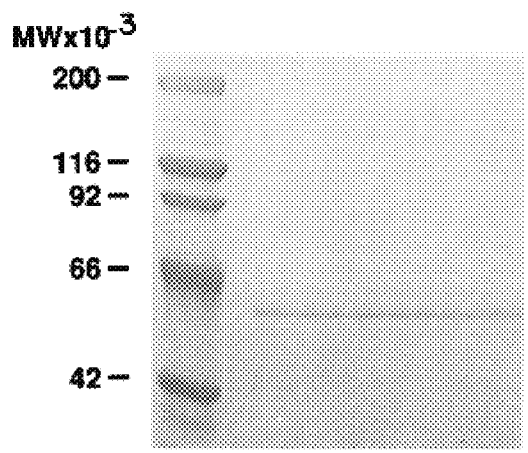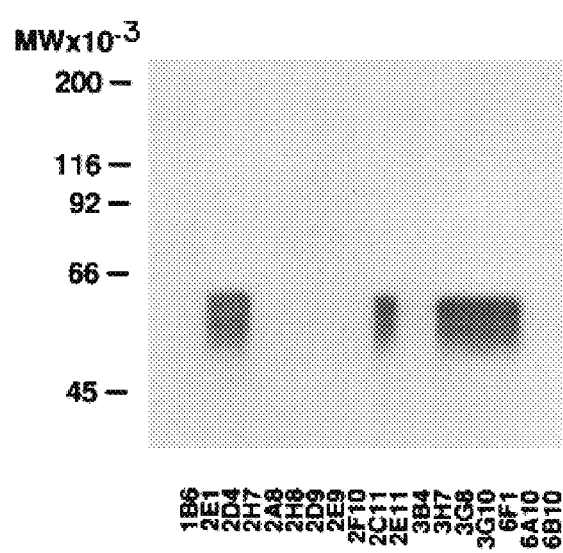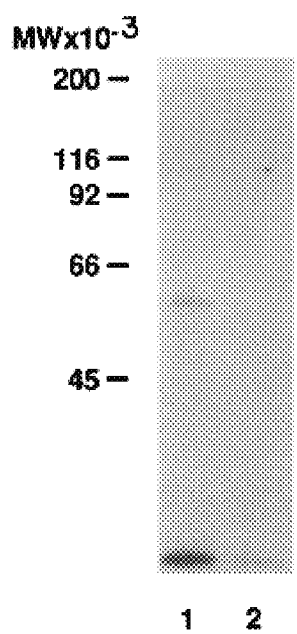
FIG.2A  FIG.2B
FIG.2C

```
         1201                                                              1260
    fv   VLHKSNETSL PTDLNQTLPS MDFGWI.ASL PDHNQNSSND TG................ QASC
fviiic   VVGKGEFTKD VGLKEMVFPS SRNLFL.TNL DNLHENNTHN QEKKIQEEIE KKETLIQENV
  epr1   .......... .......... .......... .......... .......... MTSRGPQRSC 1261                                                              1320
    fv   PPGLYQTVPP EEHY..QTFP ..IQDPDQMH STSDPSHR.S SSHELSEMLE YDRSHKSFPT
fviiic   VLHQIHTVTG TKNFMKNLFL ..LSTRQNVE GSYDGAYA.P VLQDFRSLND STNRTKKHTA
  epr1   NNHPCSSMTG RRANQIHHLT PDFSLRELLP PKKAGTWADC VSPPCGERDR CEGWADRHTA 1321                                                              1380
    fv   DISQMSPSSE HEVWQT.... VISPDLSQVT LSPELSQTNL SPDLSHTTLS PELIQRNLSP
fviiic   HFSKKGEEEN LEGLGNQTKQ IVEKYACTTR ISPNTSQQNF VTQRSKRALK Q..HKLPLEE
  epr1   CSSPASTCQV H....HQDCD SLNNMRSRHI HCGRLCHANK AVSSSKRI..D TAFFLDHFSP 1381                                                              1440
    fv   ALGQMPISPD LSHTTLSPDL .SHTTLSLDL SQTNLSPELS QTNLSPALGQ MPISPDLSHT
fviiic   TELEKRIIVD DTSTQWSKNM .KHLTPS.TL TQIDY..... NEKERGAITQ SPLSDCL...
  epr1   GKPGNQNSKN GPPKKRERER SSHCYEAAPA AQAEAPLVPL SRQNKSTVET SNLKMLISFP 1441                                                              1500
    fv   TLSLDFSQTN LSP.ELSHMT LSPELSQTNL S.....HALG QMPISPDLSH TTLSLDFSQT
fviiic   TRSHSIPQAN RSPLPIIAKVS SHPSIRPIYL T.....RVLF Q.DNSSHLPA ASYRKKDSGV
  epr1   KTLLRGPQEG WWHQGIN... ..HGSGAATL G.....PGSS ERPQSIEASC SMARRTFFAV 1501                                                              1560
    fv   NLSPELSQT. ...NLSPALG QMPLSPDPSH TTLSLDLSQT NLSPELSQTN LSPDLSEMPL
fviiic   QESSHFLQGA KKNNUSLAID TLEMTGDQRE VG.SLGTSAT NSVTYRKVEN TVLPKPDLPK
  epr1   SSNSFELLL. ....VSFAIL FLALSLSSFK NSPRVNSSNC FLTERKAQPD ECFLCSSMGS 1561                                                              1620
    fv   FADLSQIPLT PDLDQMT... ...LSPDLG. ..ETDLSPNF GQMSLSPDLS QVT...LSPDI
fviiic   TSGKVELLHK VHIYQKD... ...LFPTET. .SNGSPGHL .......DLV EGS..LLQGT
  epr1   SSGS...QHS SSLKQKK... ...HWAKSG. ..SFSVGQWM KPASAIRSGV QRS..PPRRA 1621                                                              1680
    fv   SDTTLLPDLS QISPPPDLDQ IFYPSESSQS LLLQ...... EFNESFPYPD L.GQMPSPSS
fviiic   EGAIKWNEAN RPGKVPFLRV ATESSAKTPS KLLDPLAWDN HYGTQIPKEE WKSQEKSPEK
  epr1   SS........ .......... .......... .......... .......... ..........
```

FIG.17

DIAGNOSTIC METHODS USEFUL IN THE CHARACTERIZATION OF LYMPHOPROLIFERATIVE DISEASE CHARACTERIZED BY INCREASED EPR-1

CROSS-REFERENCE TO RELATED APPLICATIONS

The present application is a continuation-in-part of U.S. patent application Ser. No. 07/988,897, filed Dec. 10, 1992 (abandoned), which is a continuation of U.S. patent application Ser. No. 07/667,957, filed Mar. 12, 1991 (abandoned), the disclosures of which are incorporated by reference herein.

This invention was made with government support under Contract Nos. PO1CA41085 and RO1 HL-43773 awarded by the National Institutes of Health. The government has certain rights in the invention.

TECHNICAL FIELD

The present invention relates to a new class of extracellular receptor molecules which are extensively homologous to, but are not identical to, coagulation factors V and VIII. The DNA and amino acid residue sequences of the receptor are described, as are antibody compositions capable of immunoreacting with the receptor or with polypeptides containing the identified amino acid residue sequences and related therapeutic and diagnostic protocols. Agents, compositions and methods useful in inhibiting normal and abnormal T lymphocyte proliferation using the antibodies disclosed herein are also disclosed. The disclosed receptors may also bind coagulation factor Xa, which binding is inhibited by the disclosed first generation monoclonal antibodies to the receptors.

BACKGROUND

It has become increasingly clear that the same enzymes that participate in blood coagulation and fibrinolysis also mediate additional and disparate biologic functions. With surprising analogies to the mechanisms of hormone-mediated growth factor activity, thrombin exerts a potent mitogenic effect on various cell types in a reaction exquisitely coordinated by specific cellular receptors (Chen, L. B., et al., *Proc. Natl. Acad. Sci. USA*, 72: 131 (1975); Glenn, K. C., et al., *Nature*, 278: 711 (1979); Baker, J. B., et al., *Nature*, 278: 743 (1979)). Similarly, the delicate balance between mitogenesis, malignant transformation, protooncogene expression, and cell differentiation has been shown to be profoundly influenced by protease activity (Unkeless, J. C., et al., *J. Exp. Med.*, 137: 85 (1973); Sullivan, L. M., et al., *Cell*, 45: 905 (1986); and Fenner, F. et al. in *The Orthopoxviruses* Academic Press (San Diego) (1989)).

In addition to preserving coagulation and fibrinolytic mechanisms (Furie, et al., *Cell* 53: 505–518 (1988)), certain proteases influence pleiotropic cellular responses, such as motility (Ossowski, *Cell* 52: 321–328 (1988)), differentiation (Bories, et al., *Cell* 59: 959–968 (1989)), and mitogenesis (Glenn, et al., *Nature* 278: 711–714 (1979); Kirchheimer, et al., *PNAS USA* 86: 5424–5428 (1989)), through the signalling properties of specialized protease receptors. As a result of ligand-dependent local proteolysis (Vu, et al., *Cell* 64: 1057–1068 (1991)) or physical receptor occupancy (Appella, et al., *J. Biol. Chem.* 262: 4437–4440 (1987)), protease receptors initiate complex pathways of cell activation with release of intracellular second messengers (Vu, et al., Id. (1991); Paris, et al., *J. Biol. Chem.* 259: 10989–10994 (1984)), protein phosphorylation (Golden, et al., *J. Cell Biol.* 111: 3117–3127 (1990)), and transcription of early activation genes (Daniel, et al., *J. Biol. Chem.* 261: 9579–9582 (1986)).

It has also been reported that abnormal expression of growth factor receptors contributes to certain neoplasias (Ulrich, et al., *Nature* 309: 418–425 (1984); Sherr, et al., *Cell* 41: 665–676 (1985); Downward, et al., *Nature* 307: 521–527 (1984)), but whether it also participates in human leukemogenesis remains uncertain. (See, e.g., Sawyers, et al., *Cell* 64: 337–350 (1991); Heard, et al., *Cell* 51: 663–673 (1987); Meeker, et al., *Blood* 76: 285–289 (1990).)

Various immune-inflammatory reactions are also affected by protease activity. The binding of urokinase as well as of thrombin to their complementary cellular receptors produces a potent chemotactic reaction with local accumulation of neutrophils and monocytes in vivo (Bovie, M. D. P., et al., *J. Immunol.*, 139: 169 (1987); Bar-Shavit, R., et al., *Science*, 220: 728 (1983)). Moreover, synthetic protease inhibitors have been shown to decrease or abolish NK- and CTL-mediated target cell lysis, as well as monocyte synthesis and release of TNF-α (Redelman, D., et al., *J. Immunol.*, 124: 870 (1980); Chang, T. W., et al., *J. Immunol.*, 124: 1028 (1980); Suffys, P., et al., *Eur. J. Biochem.*, 178: 257 (1988); Scuderi, P., *J. Immunol.*, 143: 168 (1989)).

This concept of a more direct participation of proteases in specific cellular immune effector functions has recently been reinforced by the identification of a family of related serine proteases in cytotoxic NK and CTL clones (Masson, D., et al., *Cell*, 49: 679 (1987)). These serine proteases, termed granzymes (Jenne, D., et al., *Proc. Natl. Acad. Sci. USA*, 85: 4814 (1988)), are compartmentalized in subcellular granules together with the pore-forming protein perforin and are locally released during the polarized exocytosis associated with the formation of endothelial:T cell conjugates (Masson, D., et al., *J. Biol. Chem.*, 260: 9069 (1985); Pasternack, M. S., et al., *Nature*, 322: 740.12 (1986); Podack, E. R., et al., *J. Exp. Med.*, 160: 695 (1984)).

As revealed by molecular cloning, several granzymes share a remarkable degree of homology with other serine proteases involved in coagulation and fibrinolysis, and particularly with the plasma coagulation proteases factors IXa and Xa (Jenne, D., et al., *Proc. Natl. Acad. Sci. USA*, 85: 4814 (1988); Gershenfeld, H. K., et al., *Science*, 232: 854 (1986); Jenne, D., et al., *J. Immunol.*, 140: 318 (1988); Lobe, C. G., et al., *Science*, 232: 858 (1986); Gershenfeld, H. K., et al., *Proc. Natl. Acad. Sci. USA*, 85: 1184 (1988)). While compelling evidence has accumulated suggesting a direct role for perforin in target cell injury (Masson, D., et al., *J. Biol. Chem.*, 260: 9069 (1985), Duke, R. C., et al., *J. Exp. Med.*, 170: 1451 (1989)), the participation and mechanistic role of the granzymes or other serine proteases in the lytic process remains unclear (Dennert, G., et al., *Proc. Natl. Acad. Sci. USA*, 84: 5004 (1987)).

It is also important to appreciate that the assembly of proteolytic activities on cellular surfaces initiates a variety of essential biologic responses. Specific high affinity receptors coordinate such interactions, protect the protease from inactivation by ubiquitous extracellular inhibitors, and provide optimal spatial alignment for the catalytic efficiency of the enzyme. The regulated association of coagulation and fibrinolytic proteins with a variety of cells may well exemplify these mechanisms of specialized protease-cell interactions (Miles, L. A., et al., *Fibrinolysis*, 2: 61 (1988); Morrissey, et al., *Cell*, 50: 129 (1987); Nesheim, M. E., et al., *J. Biol. Chem.*, 254: 10952 (1979)).

Binding of the coagulation protease factor Xa to vascular cells was originally recognized as the molecular prerequisite for the assembly of the prothrombinase complex with membrane-bound factor V/Va (Tracy, et al., *J. Biol. Chem.* 260: 2119–2124 (1985); Rodgers, et al., *PNAS USA* 80: 7001–7005 (1983)). However, more recent studies have also postulated the existence of additional cell surface receptors for factor Xa, distinct from factor V/Va. Activated rabbit alveolar macrophages express a factor Xa receptor only in part immunologically related to factor V/Va, that promotes prothrombin activation in the absence of factor V/Va (McGee, et al., *J. Exp. Med.* 164: 1902–1914 (1986)).

Using monoclonal antibody (mAb) strategy, similar findings were independently reported on human monocytes and monocytic cells (Altieri, et al., *J. Biol. Chem.* 264: 2969–2972 (1989)). Membrane expression of this leukocyte factor Xa receptor, denominated Effector cell Protease Receptor-1 (EPR-1), was dynamically regulated by cell activation, with an 8- to 10-fold increased surface expression during lymphocyte proliferation in vitro (Altieri, et al., *J. Immunol.* 145: 246–253 (1990)). Although of lower affinity as compared with the factor Va:factor Xa interaction (Tracy, et al., Id. (1985)), binding of factor Xa to EPR-1 promoted prothrombin activation (Altieri et al., Id. (1989)) or the generation of intermediate products of factor IX activation (Worfolk, et al., *Blood* 80: 1989–1997 (1992)) at the monocyte surface.

The primary structure of EPR-1 has now been elucidated by functional cloning and mammalian cell expression in the cDNA. The results indicate that EPR-1 is a novel transmembrane glycoprotein receptor for factor Xa, potentially implicated in protease-dependent mechanisms of intracellular signal transduction. Anti-EPR-1 antibodies described herein have also been found to possess novel utilities and capabilities.

BRIEF SUMMARY OF THE INVENTION

In this general context, the findings disclosed herein are particularly significant. Not only does the present disclosure describe a new class of extracellular receptor molecules; immunosuppressive agents acting on clonotypic and polyclonal T lymphocyte proliferation are also disclosed.

For example, it is now disclosed herein that in a test population of patients with Chronic Lymphocytic Leukemia (CLL, n=30) 90% abnormally expressed a cell surface antigen denominated Effector cell Protease Receptor-1 (EPR-1) (Altieri, et al., *J. Biol. Chem.* 264: 2969–2972 (1989); Altieri, et al., *J. Immunol.* 145: 246–253 (1990); Worfolk, et al., *Blood* 80: 1989–1997 (1992)), at a 5- to 50-fold higher density than that of normal controls.

Molecular cloning of the cDNA for EPR-1 revealed the sequence of a novel transmembrane molecule, characterized by a unique cysteine-rich extracellular module and by a cytoplasmic domain homologous to the Draf-1 proto-oncogene with numerous potential serine/threonine phosphorylation sites. Ligand binding to EPR-1 induces lymphocyte mitogenesis, and selected monoclonal antibodies to EPR-1 completely abolish T cell receptor-mediated normal lymphocyte proliferation in vitro. It is now proposed that EPR-1 is a novel cellular marker of potential pathophysiologic relevance in CLL, and a member of a previously unrecognized class of mitogenic receptors implicated in growth-associated signalling in normal and leukemic lymphocytes.

Thus, in one aspect, the present invention relates to a new class of cellular receptor molecules. The receptor molecules share regions of homology with certain coagulation cofactors, such as human coagulation factors V and VIII. Functionally, the receptor molecules bind serine protease ligands, such as the circulating proteins factor Xa, factor IX/IXa and plasmin(ogen). A preferred receptor molecule, referred to herein as EPR-1, is extensively homologous to, but different from, human factor V, and is also able to bind factor Xa. Polypeptides containing an amino acid residue sequence homologous to EPR-1 are also contemplated.

Therefore, in one embodiment, the invention contemplates an EPR-1 protein having an amino acid residue sequence as shown in FIG. 1 and identified herein as SEQ ID NO 2. In another embodiment, EPR-1 protein is capable of immunoreacting with antibodies secreted by a hybridoma selected from the group consisting of 2E1, 2C11, 2D4, 3H7, 3G8, 3G10, and 6F1. In an alternative embodiment, an EPR-1 protein is capable of immunoreacting with antibodies secreted by a hybridoma selected from the group consisting of 12H1, 9D4, 7G12, and 13E5. In yet another embodiment, the protein is isolated from a cell line selected from the group consisting of THP-1, neutrophils, NK cells, and MOLT 13.

The present invention also contemplates an EPR-1 protein or polypeptides comprising one or more sequential subsets thereof. In one embodiment, an EPR-1 polypeptide or protein includes an amino acid residue sequence corresponding to residue nos. 48–76 of SEQ ID NO 2, which are represented by the formula ADCVSPPCGERDRCEG-WADRHTACSSPAS (SEQ ID NO 3). In another embodiment, an EPR-1 polypeptide or protein includes an amino acid residue sequence at least 75%, preferably at least 80%, more preferably at least 90%, homologous to the sequence represented by the formula ADCVSPPCGER-DRCEGWADRHTACSSPAS (SEQ ID NO 3).

In one embodiment, the protein or polypeptide is isolated from a MOLT13 cell line. In another embodiment, the MOLT13 cell line comprises a MOLT13 #3 cell line having ATCC Accession No. CRL 10638.

It is further contemplated that an EPR-1 protein or polypeptide according to the present invention may be prepared via recombinant means. In one embodiment, the protein is expressed in eucaryotic cells transfected with an expression vector. For example, in one variation, the protein is expressed in Chinese hamster ovary (CHO) cells transfected with a plasmid containing a nucleotide sequence encoding the protein of SEQ ID NO 2. In another variation, the nucleotide sequence is at least 75% homologous to SEQ ID NO 1. In yet another variation, the nucleotide sequence encoding an EPR-1 protein of the present invention is the sequence identified herein as SEQ ID NO 1.

The present invention also contemplates EPR-1 protein molecules having an amino acid residue sequence at least 75% homologous to an amino acid residue sequence identified herein as SEQ ID NO 2. In one embodiment, the EPR-1 protein is capable of binding factor Xa.

EPR-1 polypeptides are also contemplated herein. In various embodiments, an EPR-1 polypeptide comprises one or more immunoreactive epitopes. In another variation, a polypeptide of the present invention is capable of immunoreacting with antibodies secreted by a hybridoma selected from the group consisting of 2E1, 2C11, 2D4, 3H7, 3G8, 3G10, and 6F1. In an alternative embodiment, an EPR-1 polypeptide is capable of immunoreacting with antibodies secreted by a hybridoma selected from the group consisting of 12H1, 9D4, 7G12, and 13E5. In various preferred embodiments, the antibodies are monoclonal. In one embodiment, an EPR-1 polypeptide has an amino acid residue sequence represented by the following formula:

ADCVSPPCGERDRCEGWADRHTACSSPAS (residue nos. 48–76 of SEQ ID NO 2) (SEQ ID NO 3).

In another embodiment, an EPR-1 polypeptide is able to immunoreact with an antibody secreted by hybridoma 2E1; in another variation, the polypeptide has an amino acid residue sequence at least 75% homologous to the amino acid residue sequence represented by the formula ADCVSPPCGERDRCEGWADRHTACSSPAS (residue nos. 48–76 of SEQ ID NO 2) (SEQ ID NO 3).

The present invention also contemplates synthetic, non-toxic, bioactive molecules capable of inhibiting lymphocyte proliferation, wherein the molecules are capable of binding to EPR-1 and reproducing the immunosuppressive effect of antibodies secreted by a hybridoma selected from the group consisting of 2E1, 2C11, 2D4, 3H7, 3G8, 3G10, and 6F1. In a preferred embodiment, the molecules are capable of binding to EPR-1 and reproducing the immunosuppressive effect of antibodies secreted by hybridoma 2E1.

In another embodiment, the present invention contemplates an isolated nucleic acid molecule encoding a protein having an amino acid residue sequence identified herein as SEQ ID NO 2. In various embodiments, the nucleic acid comprises RNA, DNA, or a combination thereof. In one preferred embodiment, a nucleic acid molecule according to the present invention comprises a deoxyribonucleotide sequence as shown in FIG. 1 and identified herein as SEQ ID NO 1. In another variation, a nucleic acid molecule according to the present invention is recombinant.

In various other embodiments, a nucleic acid molecule according to the present invention encodes one or more polypeptides comprising sequential subsets of an EPR-1 protein disclosed herein. In one variation, a nucleic acid molecule as described herein encodes an EPR-1 polypeptide or protein which includes an amino acid residue sequence corresponding to residue nos. 48–76 of SEQ ID NO 2, which are represented by the formula ADCVSPPCGERDRCEGWADRHTACSSPAS (SEQ ID NO 3). In another variation, a nucleic acid sequence encodes an EPR-1 polypeptide or protein having an amino acid residue sequence at least 75%, preferably at least 80%, more preferably at least 90%, homologous to the sequence represented by the formula ADCVSPPCGERDRCEGWADRHTACSSPAS (residue nos. 48–76 of SEQ ID NO 2) (SEQ ID NO 3).

The invention also contemplates an immunologically active molecule including an antibody combining site capable of immunoreacting with an EPR-1 polypeptide or protein, but which does not immunoreact with factor V. In various embodiments, an immunologically active molecule may comprise an antibody molecule or a fragment thereof, including those selected from the group consisting of Fab, Fab', F(ab')$_2$ and F$_v$. In alternative embodiments, an immunologically active molecule comprises an antibody combining site.

In other variations, an antibody combining site according to the present invention is produced by a hybridoma selected from the group consisting of 2E1, 2C11, 2D4, 3H7, 3G8, 3G10, and 6F1. In another aspect, the hybridoma is selected from the group consisting of 12H1, 7G12, 9D4, and 13E5.

In various preferred embodiments, the immunologically active molecules comprise monoclonal antibodies or fragments thereof. In other embodiments, an immunologically active molecule is capable of immunoreacting with a protein is isolated from the MOLT13 #3 cell line having ATCC Accession No. CRL 10638.

The present invention also contemplates methods of inhibiting antigen-specific T cell proliferation in an individual in need of treatment, comprising administering to the individual a therapeutically effective amount of an immunologically active molecule that binds EPR-1. In one embodiment, the EPR-1 is membrane-bound. In another embodiment, the EPR-1 is free of cell membranes (i.e., in soluble form), or is in isolated and/or purified form.

In another embodiment, the invention contemplates a method of blocking immune responsiveness in an individual for a predetermined length of time without provoking an irreversible systemic immunosuppressive effect, comprising administering to the individual a therapeutically effective amount of an immunologically active molecule that immunoreacts with EPR-1. In one embodiment, the EPR-1 is membrane-bound. In another embodiment, the EPR-1 is free of cell membranes (i.e., in soluble form), or is in isolated and/or purified form.

In all the various methods disclosed herein, the immunologically active molecule comprises an antibody molecule or fragment thereof, wherein the antibody molecule or fragment includes an antibody combining site. In alternative variations, the antibody fragment is selected from the group consisting of Fab, Fab', F(ab')$_2$ and F$_v$. The invention further contemplates that the antibody combining site is produced by a hybridoma selected from the group consisting of 2E1, 2C11, 2D4, 3H7, 3G8, 3G10, and 6F1. In another variation, the antibody combining site is produced by a hybridoma selected from the group consisting of 7G12, 12H1, 9D4, and 13E5. In various preferred embodiments, the antibody combining site is monoclonal.

The invention also contemplates a diagnostic method useful in the characterization of lymphoproliferative disease, comprising the steps of: (a) obtaining a cell-containing vascular fluid sample from an individual; (b) admixing the sample with an immunologically active molecule capable of immunoreacting with EPR-1; (c) maintaining the admixture under biological assay conditions for a time period sufficient for any cells expressing EPR-1 to immunoreact with the immunologically active molecules to form an immunocomplex; (d) separating the immunocomplex from any unreacted immunologically active molecules present in the admixture; and (e) determining the presence of immunoreaction product formed thereby.

The aforementioned method may further comprise the step of correlating the amount of product detected in step (e) with the amount of EPR-1 expressed by the cells. In one variation, the immunologically active molecules may be labeled. In yet another variation, the disease is chronic lymphocytic leukemia (CLL) or EPR-1$^+$ type hairy cell leukemia (HCL).

In a somewhat different vein, the present invention also contemplates a method of inducing lymphocyte proliferation, comprising administration of an effective amount of an EPR-1 ligand. In one embodiment, the ligand comprises factor Xa or a factor Xa homolog. In another embodiment, the ligand is selected from the group consisting of soluble molecules, cell-associated molecules, cytokines, and lymphocyte co-stimulatory agents.

In another aspect, the present invention discloses potential immunosuppressive agents which inhibit clonotypic T lymphocyte proliferation and block abnormal expansion and/or reactivity of T lymphocytes. The within-disclosed novel agents have a unique selectivity; i.e., they do not appear to interact directly with the T cell receptor, thus reducing the risk of additional perturbations of T cell function. Such agents are potentially useful in all conditions requiring targeted immunosuppression, such as autoimmune disorders, diabetes, transplant rejection, and hematopoietic (lymphocyte) malignancies, to name a few examples.

A preferred embodiment of the invention comprises a purified protein that has a relative molecular weight of about 62–74 kDa and may further comprise an amino acid residue sequence as illustrated in FIG. 1 (SEQ ID NO 2). In another embodiment, the purified protein has a relative molecular weight within the 62–74 kDa range, depending upon the cell line from which it is purified and the extent of glycosylation of the molecule. For example, an EPR-1 protein derived from mononuclear cells may have a relative molecular weight of about 62 kDa, while an EPR-1 protein derived from THP-1 cells may have a relative molecular weight of about 74 kDa.

The invention also contemplates proteins or polypeptides having EPR-1 activity which are at least 75% homologous, preferably 80% homologous, more preferably at least 85% homologous, and even more preferably at least 90% homologous, to the EPR-1 protein identified herein as SEQ ID NO 2. The invention also contemplates proteins and polypeptides encoded by a nucleotide molecule substantially homologous to SEQ ID NO 1.

In another aspect of the invention, an EPR-1 protein of the present invention immunoreacts with an antibody according to the present invention. In one embodiment, the antibody is produced by the hybridoma designated 12H1 (ATCC Accession No. HB 10637). In another embodiment, the antibody is produced by the hybridoma designated 2E1. In yet another aspect of the invention, the protein is the EPR-1 protein isolated from the cell line designated MOLT13 #3 (ATCC Accession No. CRL 10638). Another variation contemplates that the EPR-1 protein has an amino acid residue sequence substantially homologous to SEQ ID NO 2.

The invention also contemplates a DNA molecule encoding the amino acid residue sequence identified herein as SEQ ID NO 2. A preferred DNA molecule is illustrated in FIG. 1 and is identified therein (and herein) as SEQ ID NO 1.

Also contemplated by the present invention is a DNA segment that codes for a protein or polypeptide as defined previously and a vector, i.e., self-replicating DNA molecule, including the DNA segment.

A method of assaying for the presence of an EPR-1 receptor molecule on a cell surface is also contemplated. The method comprises the steps of:

(a) admixing a cell or cell lysate suspected of expressing the receptor molecule with an antibody composition described before, such as hybridoma 12H1;

(b) maintaining the admixture for a time sufficient to form an immunoreaction product; and (c) determining the presence of immunoreaction product and thereby detecting presence of the receptor molecule.

Also contemplated is a method of monitoring the response to treatment of a patient having a disease associated with one of the within-described proteins or polypeptides, wherein the proteins or polypeptides are localized on cells present in a body sample withdrawn from the patient and are useful as markers for the disease state. The method comprises assaying for the marker using an antibody composition such as those described herein; repeating the assay after a course of treatment; and determining the patient's response to treatment as a function of the amount of that cell surface protein present after treatment. An exemplary disease state which may be monitored according to this invention is chronic lymphocytic leukemia (CLL).

BRIEF DESCRIPTION OF THE DRAWINGS

FIG. 1 illustrates the EPR-1 cDNA sequence and the protein translation.

FIG. 2 illustrates the characterization of EPR-1 using first- and second-generation monoclonal antibodies. In FIG. 2A, EPR-1 ($M_r$ ~62 kDa) was affinity-purified from MOLT13 lymphocyte extracts using mAb 12H1, electrophoresed on a single-well 7.5% SDS polyacrylamide slab gel under non-reducing conditions and stained with Coomassie blue. In FIG. 2B, immunopurified EPR-1 shown in A was electroblotted to IMMOBILON (poly-vinylidene flouride membrane) membranes and incubated with the indicated anti-MOLT13 hybridomas in a slot blotter apparatus, followed by $^{125}$I-F(ab')$_2$ goat anti-mouse IgG and autoradiography. In FIG. 2C, $^{125}$I-surface labelled PBMC extracts were immunoprecipitated with a positive anti-MOLT13 hybridoma shown in FIG. B (mAb 2E1, lane 1), or with control mAb 6B4 (lane 2). MW, relative molecular weight markers ($\times 10^{-3}$).

In FIG. 8A, 1 µg/ml soluble OKT3 is utilized to activate T-cell response. Increasing amounts of anti-EPR-1 antibody 2E1 (closed squares) and mIgG (murine IgG; open squares) were added to the stimulated cells, as indicated on the horizontal axis (Ab concentration, in µg/ml), and $^3$H-TdR uptake (in cpm) was determined.

In FIG. 8B, 0.5 µg/well immobilized OKT3 was utilized to activate T-cell response. Increasing amounts of 2E1 (closed squares) and of mIgG (open squares) were added to the stimulated cells, as indicated on the horizontal axis, and $^3$H-TdR uptake (in cpm) was determined.

In FIG. 8C, a mixed lymphocyte culture (mlc) was used. (MLCs are generally alloreactive, as noncompatible cells in such cultures activate each other.) Varying concentrations of mOKT4a (closed triangles), 2E1 (closed squares) and mIgG (open squares) were added, as indicated on the horizontal axis, and $^3$H-TdR uptake was determined.

FIGS. 11A, 11B, and 12 show that 2E1 inhibits IL-2 receptor expression and IL-2 generation. IL-2 concentrations were assayed as described herein 24, 48, and 72 hours after OKT3 stimulation. After 24 hours, small amounts of IL-2 were detected in the supernatant following 2E1 administration, as shown, while substantial amounts of IL-2 were present in all other OKT3-stimulated wells. In FIGS. 11A and B, IL-2 concentration (pg/ml) is shown on the vertical axis. In FIG. 11A, IL-2 generation was measured after 24 hours. The bars shown on the horizontal axis represent results when no OKT3, OKT3, OKT3+2E1, OKT3+mouse IgG, and OKT3 (1 ng/ml) were administered. FIG. 11B illustrates IL-2 kinetics at 24, 48, and 72 hours (horizontal axis) in wells receiving no OKT3 (open squares); OKT3 (large closed squares); OKT3+2E1 (closed triangles); OKT3+mouse IgG2a (closed circles); and OKT3 (1 ng/ml only; small closed square). (At all data points, the amount of OKT3 administered was 1 µg/ml, unless indicated otherwise.)

In FIG. 12A, mean chamber number (vertical axis) is plotted against hours (0–96), with readings taken at 24, 48, and 72 hours.

In FIG. 13A, TNF-β kinetics are illustrated. TNF-β (pg/ml, vertical axis) is plotted against time in hours (horizontal axis). Data for cells receiving no OKT3 (open squares), OKT3 (large closed squares), OKT3+2E1 (closed triangles), OKT3+mouse IgG2a (closed circles) and OKT3 (1 ng/ml only, small closed squares) are indicated. (At all data points, the amount of OKT3 administered was 1 µg/ml, except where indicated otherwise.)

In FIG. 14A, proliferation, as measured by $^3$H-TdR uptake (in cpm), is plotted against time in hours. Results of the administration of OKT3 (closed squares); OKT3+murine IgG2a (closed circles); OKT3+2E1 (closed triangles); and no OKT3 (open squares) are indicated. Except where indicated otherwise, 1 µg/ml of OKT3 was administered as a stimulant.

FIG. 17 illustrates regions of homology or similarity between EPR-1 (SEQ ID NO 2), factor V (SEQ ID NO 4), and Factor VIIIc (SEQ ID NO 5). Boxed areas indicate identity of amino acid residues among the three sequences. Conservative substitutions, and regions of identity between factors V and VIIIc only, have also been identified but are not presently indicated in the figure.

DETAILED DESCRIPTION OF THE INVENTION

A. Definitions

Figure 3A:
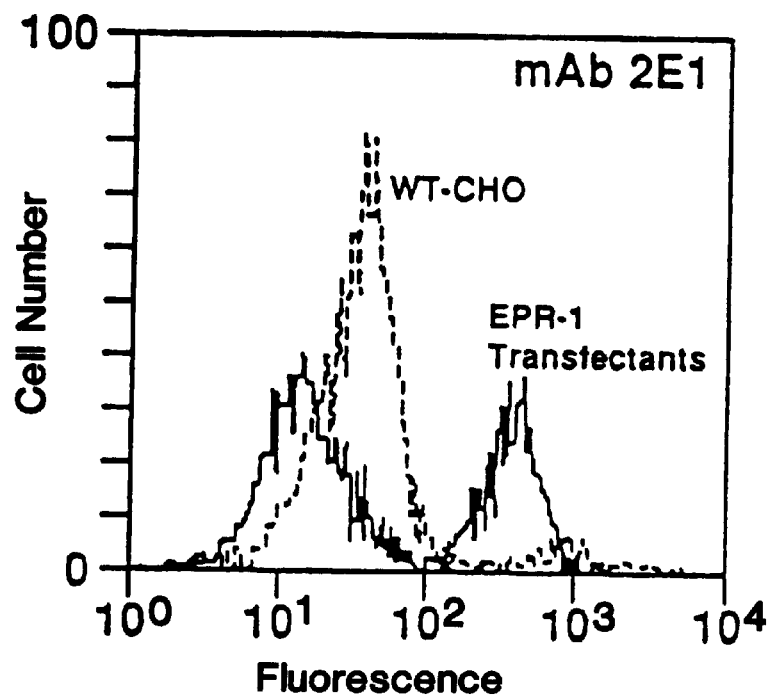
FIG. 3 illustrates mammalian cell expression of EPR-1 cDNA. A full length EPR-1 cDNA was inserted in the mammalian cell expression vector pRC/CMV (Invitrogen, San Diego, Calif.), oriented, and transfected into Chinese Hamster Ovary (CHO) cells by electroporation. Forty-eight hours after transfection, CHO cells were diluted fifteen fold and cultivated in DMEM (Whittaker) selection media supplemented with 0.7 mg/ml Geneticin (G418, GIBCO, Grand Island, N.Y.). After two weeks' culture in DMEM/Geneticin selection media, wild type (WT) CHO cells or EPR-1 transfectants were harvested and analyzed for their reactivity with anti-EPR-1 mAbs 12H1 or 2E1 by flow cytometry.
Figure 3B:
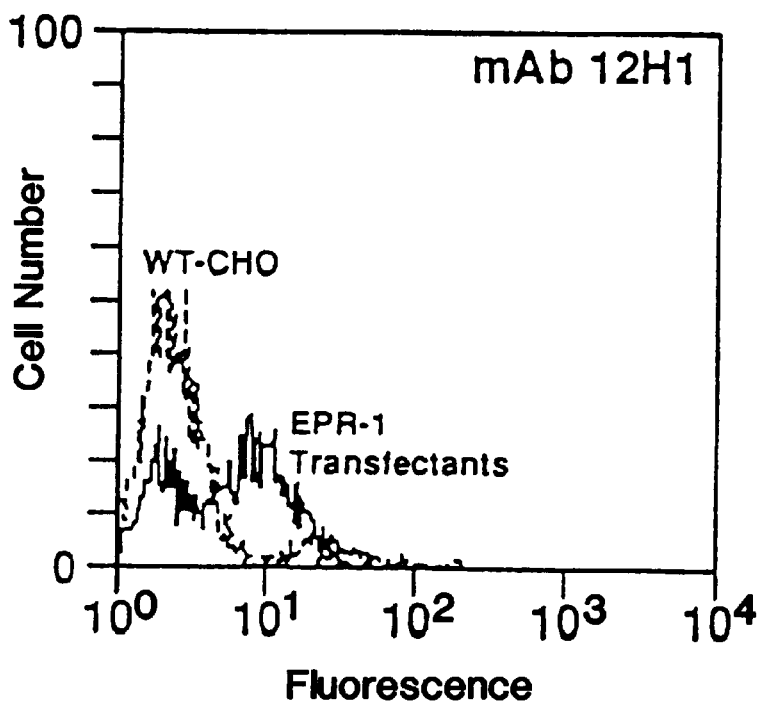

Amino Acid Residue Secuence: a series of two or more amino acid residues joined via peptide linkages between adjacent residues to form a peptide or polypeptide. An amino acid residue sequence is conveniently represented by the one or three letter abbreviations for its constituent amino acids. The abbreviations used herein for amino acids are those provided at 37 C.F.R. §1.822(b) (2) and are reproduced in the following Table of Correspondence:

TABLE OF CORRESPONDENCE

| ABBREVIATION | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| J | Xaa | Unspecified |

The individual residues comprising an amino acid residue sequence herein may be in the D or L isomeric form as long as the desired functional property is retained by molecule(s) incorporating the amino acid residue sequence. Also, the amino acid residue sequence may include post-translationally modified amino acids, e.g., hydroxylated, glycosylated amino acid residues, or residues linked via disulfide bonds. In addition, an amino acid residue sequence can include one or more modified or unusual amino acids, such as those listed in 37 C.F.R. §1.822(b) (4), which are incorporated herein by reference. An amino acid residue sequence can be represented by the abbreviations corresponding to its constituent amino acids in which a hyphen between two adjacent abbreviations indicates a peptide linkage between the corresponding residues.

Antibody: a polypeptide which chemically binds to a haptenic group, i.e., ligand. The term antibodies, as used herein, includes immunoglobulin molecules and immunologically active fragments of immunoglobulin molecules. Such portions known in the art as Fab, Fab', F(ab')$_2$ and F$_v$ are included. Typically, antibodies bind ligands that range in size from about 6 to about 34 Å with association constants in the range of about $10^4$ to $10^{10}$ M$^{-1}$, and as high as $10^{13}$ M$^{-1}$. Antibodies can bind a wide range of ligands, including small molecules such as steroids and prostaglandins, biopolymers such as nucleic acids, proteins and polysaccharides, and synthetic polymers such as polypropylene. An "antibody combining site" is that structural portion of an antibody molecule comprised of a heavy and light chain variable and hypervariable regions that specifically binds (immunoreacts with) antigen. The term "immunoreact" in its various forms is used herein to refer to binding between an antigenic determinant-containing molecule (antigen) and a molecule containing an antibody combining site such as a whole antibody molecule or a portion thereof. An "antigenic determinant" is the structural portion of the antigen that is immunologically bound by an antibody combining site. The term is also used interchangeably with "epitope". Antibodies can bind a single epitope of an antigen (monoclonal) or multiple epitopes (polyclonal). The term monoclonal antibody may be abbreviated herein as mAb.

Ligand: a molecule having a structural region that binds specifically to a particular receptor molecule, usually via electrostatic forces and/or hydrogen bonds.

Peptide/Polypeptide: Polypeptide and peptide are terms used interchangeably herein to designate a series of at least two and generally no more than about 50 amino acid residues connected one to the other by peptide bonds between the alpha-amino and carboxy groups of adjacent residues. The primary structure of a polypeptide has a primary amine group at one terminus and a carboxylic acid group at the other terminus of the polymer. Thus, a polypeptide may be represented by the formula:

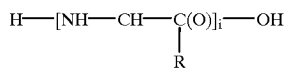

where R is a side chain characteristic of a given amino acid residue and i indicates the number of amino acid residues comprising the polymer which number is two or more. A polypeptide can comprise one or more amino acid residue sequences. Also, a polypeptide in aqueous solution is usually in one or more zwitterionic forms depending on the pH of the solution.

Protein: a single polypeptide or set of crosslinked polypeptides generally comprising more than about 50 amino acid residues connected one to the other as in a polypeptide. Proteins can have chemical crosslinking, i.e., via disulfide bridges, within the same polypeptide chain or between adjacent polypeptides. Proteins can be glycosylated in which case they are called glycoproteins.

Receptor: Receptor and receptor protein are terms used herein to indicate a biologically active proteinaceous molecule that specifically binds to (or with) another molecule (e.g., a ligand).

Substantially homologous means that a particular subject sequence or molecule, for example, a mutant sequence, varies from a reference sequence by one or more substitutions, deletions, or additions, the net effect of which does not result in an adverse functional dissimilarity between reference and subject sequences. For purposes of the present invention, amino acid sequences having greater than 75% similarity, preferably greater than 80% similarity, more preferably greater than 90% similarity, equivalent biological activity, and equivalent expression characteristics are considered substantially homologous and are included within the scope of proteins defined by the terms "serine protease receptor", "EPR-1", and "EPR-1 peptide or polypeptide". Amino acid sequences having greater than 40 percent similarity are considered substantially similar. For purposes of determining homology or similarity, truncation or internal deletions of the reference sequence should be disregarded, as should subsequent modifications of the molecule, e.g., glycosylation. Sequences having lesser degrees of homology and comparable bioactivity are considered equivalents. Similarly, nucleotide sequences at least 75% homologous to that identified herein as SEQ ID NO 1 are considered substantially homologous.

B. EPR-1

FIG. 1 illustrates the EPR-1 cDNA sequence and protein translation. Methods used were essentially as follows. Full length EPR-1 cDNA clones were isolated by screening at high stringency (65° C., 5×SSC) the following human cDNA libraries using λ104 as a probe: λgt11 MLT, λgt10 HEL (erythroleukemia cells), λgt11 HUVEC (human umbilical vein endothelial cells), and pcDNAII Daudi (Invitrogen, San Diego, Calif.). A total of 28 independent clones were isolated, plaque purified, subcloned in PBSKS⁻ (except clones from pcDNAII), and characterized by restriction analysis. DNA sequencing was carried out on both strands of Exonuclease III (Promega, Madison, Wis.)-generated nested deletions using Sequenase (USB, Cleveland, Ohio).

In order to isolate cDNA clones encoding EPR-1, a novel mAb panel was raised against the EPR-1⁺ cell line MOLT13. Seven of the mAbs from the panel reacted with MOLT13 cells as determined by flow cytometry (not shown), and strongly bound to affinity-purified EPR-1 in Western blots (FIGS. 2A and 2B). One of them, 2E1, was selected for further investigations. Monoclonal antibody 2E1 immunoprecipitated EPR-1 from $^{125}$I-surface-labelled PBMC extracts (FIG. 2C).

As opposed to the broad $M_r$ ~74 kDa band previously resolved from THP-1 cells (Altieri, et al., Id. (1989), EPR-1 isolated from PBMC extracts appeared as a sharper band of $M_r$ ~62 kDa (FIG. 2). This apparent molecular heterogeneity was further investigated. In agreement with prior observations (Altieri, et al., Id. (1989)), mAb 2E1 immunoprecipitated EPR-1 as a broad $M_r$ ~74 kDa band from $^{125}$I-surface labeled THP-1 cells (FIG. 2), indistinguishable for molecular weight and structural organization from the band immunoprecipitated by the first generation anti-EPR-1 mAbs 12H1 and 13E5 under the same experimental conditions (FIG. 2). The data confirmed the recognition of mAb 2E1 for EPR-1 (FIG. 2) and suggested that variations in EPR-1 Mr between PBMC and THP-1 cells might reflect cell-specific differences in receptor glycosylation (see below). At variance with the first anti-EPR-1 mAb panel (Altieri, et al., Id. (1989)), mAb 2E1 only slightly inhibited prothrombin activation on THP-1 cells (not shown), thus implicating a different epitope recognition.

Immunoscreening of a human lymphocyte expression library (λgt11 cDNA library) with one of these mAbs (2E1) yielded a single positive clone (λ104) that hybridized in Northern blots with a message of 1.9 Kb in RNA extracted from various hemopoietic EPR-1⁺ cell lines. Full length EPR-1 clones were isolated by screening human cDNA libraries using λ104 as a probe.

The consensus EPR-1 cDNA sequence deduced from 28 independent clones is 1,165 bp long and contains a 36 bp 5' untranslated region and a 115 bp 3' untranslated region. (FIG. 1). The initiating methionine was assigned to the first in-frame ATG which is preceded by a motif that conforms well to the Kozak's consensus for initiation of translation in eukaryotes (CCGAGATG) (see Kozak, M. *Nucleic Acids Res.* 12: 857–870 (1984)). An in-frame TGA termination codon is found 33 bp upstream of the putative initiating ATG (FIG. 1). Analysis of the predicted protein translation reveals that the EPR-1 protein is unusually basic (pI=11.6) and consists of 337 amino acid residues with an estimated molecular weight of 36,822. In addition to the two N-linked glycosylation sites at positions 168 and 265 (FIG. 1), there are four O-linked glycosylation sites at positions 2, 76, 170, and 174, plus a chondroitin sulfate attachment site at position 204, that altogether may provide anchoring for additional carbohydrate chains to account for cell-specific variations in EPR-1 relative molecular weight ($M_r$) of 62–74 kDa (see above).

The first 100 amino acid residues following the initiating methionine contain the mAb 2E1 immunoreactive epitope (mapped to residues 48–76) and feature a unique cysteine-rich module, followed by a highly charged and surface-exposed region (residues 125–150), and by a putative membrane-spanning domain of 26 hydrophobic amino acids (FIG. 1). The mAb 2E1 epitope on EPR-1 comprises the following amino acid residues (using single-letter format):

```
48                              76
ADCVSPPCGERDRCEGWADRHTACSSPAS            (SEQ ID NO 3)

(SEQ ID NOS 2, residue 48-76).
```

The 81 amino acid-long EPR-1 cytoplasmic tail is highly rich in serine residues (26%), and contains at least 15 potential serine/threonine phosphorylation sites with consensus sequences for protein kinase C, cAMP-dependent kinase, growth-associated histone kinase, and glycogen synthase kinase (Pearson, et al., *Methods Enzymol.* 200: 62–81 (1991)) (FIG. 1).

The authenticity of the cloned cDNA as EPR-1 (Altieri, et al., Id. (1989); Altieri, et al., Id. (1990); Worfolk, et al., Id. (1992)) was validated using two independent experimental approaches. First, CHO cells stably transfected with EPR-1 cDNA strongly reacted by flow cytometry with both generations of anti-EPR-1 mAbs 12H1 and 2E1 (FIGS. 3A and B). These data also confirm the expected membrane orientation of the molecule (mAb 2E1 epitope outside), even if, similarly to other secreted and membrane-anchored proteins (Rapoport, *Crit. Rev. Biochem.* 20: 73–137 (1986)), a hydrophobic amino-terminus leader sequence is not evident from the EPR-1 sequence (FIG. 1).

Quantitative studies further confirmed that the CHO cells stably transfected with EPR-1 cDNA expressed significantly greater levels of EPR-1 protein than EPR-1$^+$ cell lines such as THP and MOLT13; in general, EPR-1 expression was five-fold higher in the transfected CHO cells (data not shown).

Second, a rabbit polyclonal antibody generated against an EPR-1 bacterial fusion protein (bp248–1121) immunoblotted EPR-1 as a major $M_r$ ~62 kDa band from PBMC extracts, while no specific bands were detected by a preimmune serum under the same experimental conditions (data not shown).

Figure 5A:
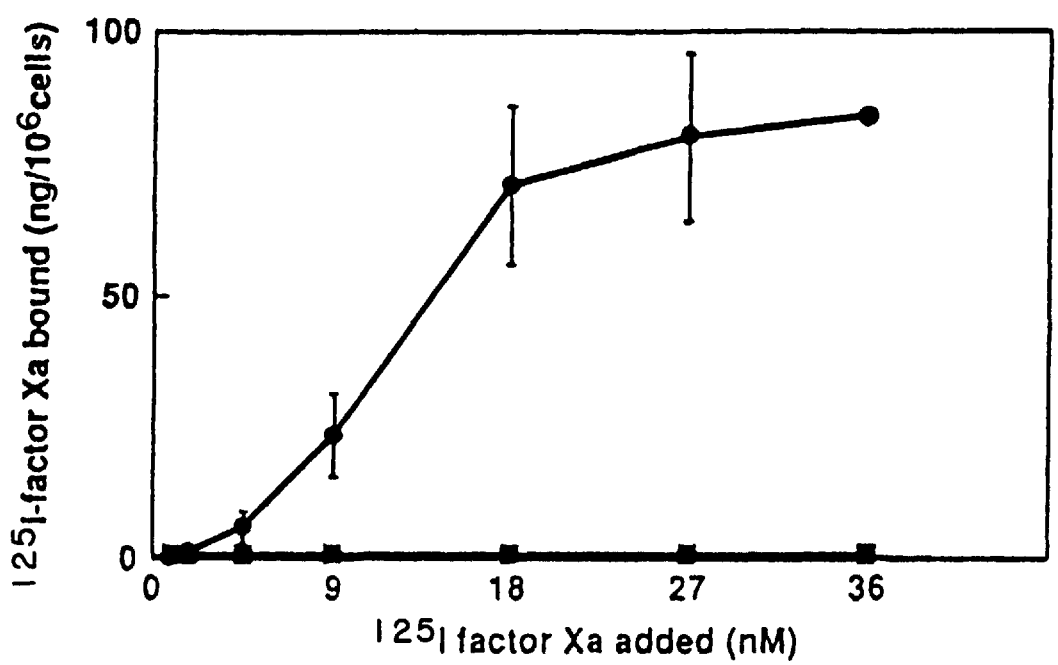
FIGS. 5A and B illustrate EPR-1 function in transfected cells. In FIG. A, wild-type (WT) CHO cells (closed squares) or EPR-1 CHO transfectants (closed circles) were incubated with increasing concentrations of $^{125}$I-factor Xa (0.45–36 nM) for 15 minutes at 22° C. in the presence of 2.5 mM CaCl$_2$. Non-specific binding was assessed in the presence of a 50-fold molar excess of unlabeled factor Xa and was subtracted from the total to calculate net specific binding. Data are the mean±S.E.M. of two independent experiments. $^{125}$I-factor Xa bound at saturation (27 nM) to EPR-1 CHO transfectants corresponded to 729,000±102,000 molecules/cell.
Figure 5B:
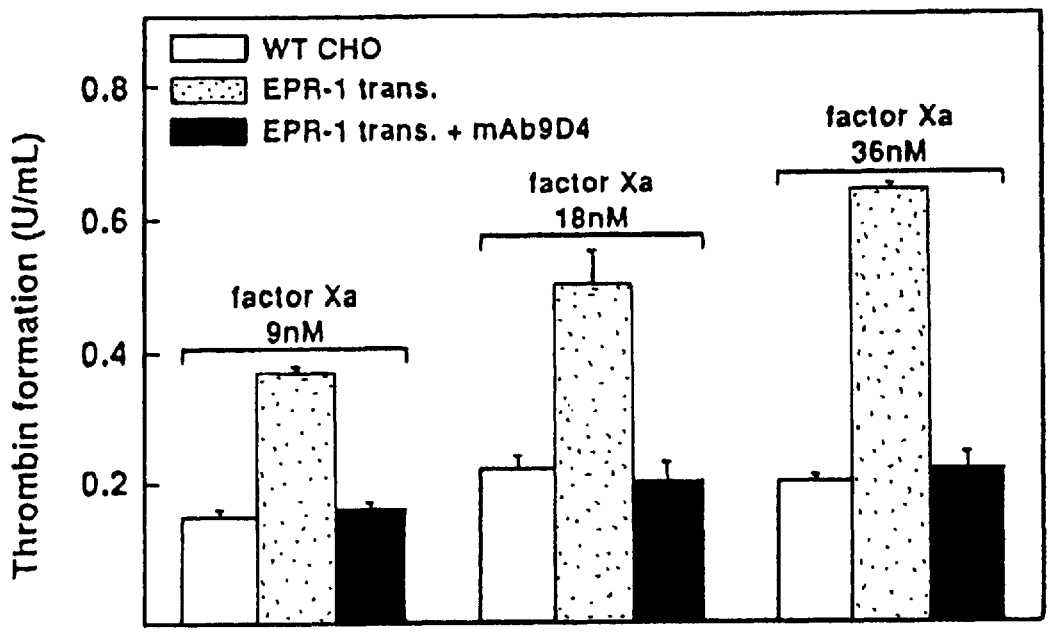
In FIG. 5B, WT CHO cells or EPR-1 CHO transfectants at 1×10$^5$/ml were preincubated with the indicated increasing concentrations of factor Xa, 10 µg/ml prothrombin, and 2.5 mM CaCl$_2$ for 5 minutes at 22° C. Thrombin formation in the presence or in the absence of anti-EPR-1 mAb 9D4 (Altieri, et al., Id. (1990)) was assessed by a sensitive clotting assay as described (Altieri, et al., Id. (1989)). Data are expressed as mean±S.E.M. of two independent experiments.

The EPR-1 recognition for factor Xa postulated in our previous studies (Altieri, et al., Id. (1989); Altieri, et al., Id. (1990)) was substantiated using genetically engineered transfectants. While no specific interaction of $^{125}$I-factor Xa with WT CHO cells could be demonstrated (FIG. 5A), EPR-1 CHO transfectants bound $^{125}$I-factor Xa in a specific and saturable reaction, regulated by an apparent $K_d$ of ~10–15 nM, with maximal association of 80 ng factor Xa/10$^6$ cells (FIG. 5A). Under these experimental conditions and in the absence of exogenous factor V/Va, EPR-1 CHO transfectants promoted prothrombin activation in a factor Xa-concentration-dependent manner (FIG. 5B), although apparently in a quantitatively and kinetically less efficient reaction as compared with that mediated by membrane assembly of the prothrombinase complex with factor V/Va (Tracy, et al., *J. Biol. Chem.* 260: 2119–2124 (1985)). Finally, preincubation of EPR-1 CHO transfectants with anti-EPR-1 mAb 9D4 blocked $^{125}$I-factor Xa binding and prothrombin activation, in agreement with previous observations (Altieri, et al., Id., (1989) and (1990)). (See FIGS. 5A and 5B.)

Computer searches of available databases revealed limited evidence of homologous sequences to EPR-1. A comparison of the amino acid residue sequences of EPR-1, factor V, and factor VIIIc provides some evidence of homologous regions shared by the three molecules (see FIG. 17). FIG. 17 illustrates regions of homology or similarity between EPR-1, factor V, and Factor VIIIc. Boxed areas indicate identity of amino acid residues among the three sequences. Conservative substitutions, and regions of identity between factors V and VIIIc only, have also been identified but are not presently indicated in the figure.

Thus, the immunologic cross-reactivity with factor V/Va displayed by the first generation of anti-EPR-1 mAbs (Altieri, et al., Id. (1989)) might reflect their recognition of shared discontinuous epitope(s) (Reeves, et al., *J. Clin. Invest.* 84: 562–567 (1989)), and/or common posttranslational component(s) (Hoffman, et al., *PNAS USA* 84: 2523–2527 (1987)). In this context, a 10-residue cluster surrounding the N- and O-linked glycosylation sites at positions 168–170 in EPR-1 (SEQ ID NO 1) share a 54% identity with factor V sequence residues 818–829, including the two carbohydrate attachment sites.

As for other protease receptors (Appella, et al., Id. (1987); Roldan, et al., *EMBO J.* 9: 467–474 (1990)), the large number of potential phosphorylation sites in the EPR-1 cytoplasmic tails suggests a possible role for this molecule in protease-dependent mechanisms of intracellular signal transduction. Whether or not factor Xa binding is associated with EPR-1 proteolysis and generation of a truncated, activating receptor (Vu, et al., Id. (1991)), is currently not known. Although this possibility should be considered for the numerous proteolytic sensitive sites in the EPR-1 extracellular domain, including an Arg$^{229}$–Thr$^{230}$ potential factor Xa cleavage site, physical occupancy of EPR-1 with the first generation mAb 13E5 was sufficient to increase cytosolic free [Ca$^{2+}$]$_i$ in single adherent lymphocytes. The pathophysiologic relevance of EPR-1 ligand recognition might reside in its potential participation in early molecular events of vascular injury and atherosclerosis. As a consequence of factor Xa binding to EPR-1, locally generated thrombin or factor Xa itself (Gasic, et al., *PNAS USA* 89: 2317–2320 (1992)) might induce platelet aggregation and secretion (Shuman, *Ann. N.Y. Acad. Sci.* 485: 349–368 (1986)), leukocyte chemotaxis (Bar-Shavit, et al., *J. Cell. Biol.* 96: 282–285 (1983)), and proliferation of smooth muscle cells (Gasic, et al., Id. (1992)), thus contributing to the establishment of the atherosclerotic plaque (Ross, *Nature* 362: 801–809 (1993)). The availability of EPR-1 cDNA and of EPR-1 transfectants should help elucidate the molecular requirements of factor Xa recognition and the potential signalling pathways associated with EPR-1 occupancy.

Clone λ104 was isolated from immunoscreening of 1×10$^6$ IPTG-induced plaques of a human lymphocyte (MLT) λgt11 cDNA library using anti-EPR-1 mAb (data not shown). The immunoreactive clone λ104 was plaque purified, subcloned in the EcoRI site of pBluescript (pBSKS$^-$, Stratagene, La Jolla, Calif.) and characterized by restriction digest. It was then sequenced on both strands by the dideoxy chain termination method using Sequenase (USB, Cleveland, Ohio).

Molecular cloning of the cDNA for EPR-1 reveals the sequence of a novel transmembrane molecule, characterized by a unique cysteine-rich extracellular module and by a cytoplasmic domain with numerous potential serine/threonine phosphorylation sites.

EPR-1 is proposed herein to be a novel cellular marker of potential pathophysiologic relevance in CLL, and a member of a previously unrecognized class of mitogenic receptors implicated in growth-associated signalling in normal and leukemic lymphocytes.

As noted above, in a preferred embodiment of the invention, an EPR-1 protein comprises the amino acid residue sequence illustrated in FIG. 1 (SEQ ID NO 2), although it is to be understood that proteins and polypeptides sharing significant homologies with all or a portion of the illustrated sequence are also encompassed by the present invention. Characteristically, the protein has a relative molecular weight of about 62–74 kDa, as resolved in immunoprecipitation from surface iodinated lymphocytes or from monocyte extracts.

In a further preferred embodiment, the protein is isolated from the cell line designated MOLT13 #3 and has a relative molecular weight of about 62–74 kDa. The MOLT13 #3 cell line was deposited at the American Type Culture Collection (ATCC) 12301 Parklawn Drive, Rockville, Md., USA 20852, on Jan. 11, 1991 and received Accession Number CRL 10638.

In another embodiment of the invention, the protein is immunoreactive with certain antisera to human factor V as well as with polyclonal antibodies purified from the antisera, e.g., by immunoadsorption on immobilized, purified human factor V. In a further aspect of the invention, the protein immunoreacts with antibodies to human factor VIII. Hence, although the instant EPR protein is not a human factor V or VIII protein per se, it possesses epitopes that are cross-reactive with ligands for certain epitopes of factors V and VIII.

In a further preferred embodiment of the invention, the isolated protein immunoreacts with antibodies such as those produced by the hybridoma designated 12H1, which was deposited on Jan. 11, 1991, at the ATCC and was given the designation ATCC HB 10637. Other preferred hybridomas include those designated as 2C11, 2D4, 2E1, 3H7, 3G8, 3G10, and 6F1. Hybridoma 2E1 was deposited on Jan. 27, 1994, at the ATCC, and was given the designation ATCC HB 11536.

These deposits were made pursuant to, and in compliance with, all applicable provisions of the Budapest Treaty as described herein. The cell lines, hybridomas, and antibodies of the present invention are described further hereinbelow.

C. Polypeptides

A polypeptide of the present invention is derived from a new class of cell surface receptors designated effector cell protease receptors (EPRs), as members of the class bind protease ligands and tend to be found on many types of inflammatory effector cells. The first member of this class (EPR-1) is shown to bind protease ligands, of which human factor Xa is prototypic.

A polypeptide of the present invention corresponds in amino acid residue sequence to one or more amino acid residue sequence subsets of EPR-1. Moreover, a polypeptide according to the present invention may have pronounced homologies with the amino acid residue sequence of human coagulation factor V, or the amino acid residue sequence of factor Va. A polypeptide of the invention may also exhibit homology in sequence to a polypeptide portion of factor VIII, as well as to a polypeptide of the murine protein denominated MFG E-8 (Stubbs et al., *PNAS USA* 87: 8417 (1990)). however, a polypeptide of the present invention is not identical to, and is distinguishable from, factors V, Va, VIII, and murine MFG E-8.

A polypeptide of the present invention may also comprise a 29 amino acid-long region included within the first 100 residues following the initiating methionine of EPR-1 (residues 48–76) corresponding to the mAb 2E1 epitope on EPR-1. This 29 amino acid-long region comprises an amino acid residue sequence represented by the formula:

ADCVSPPCGERDRCEGWADRHTACSSPAS (residue nos. 48–76 of SEQ ID NO 2) (SEQ ID NO 3).

It is also anticipated that polypeptides homologous to this amino acid residue sequence will be useful. Homologous peptides are preferably at least 50% homologous to the mAb 2E1 epitope; more preferably, they are at least 75% homologous; even more preferably, they are at least 85% homologous; most preferably, they are at least 90–95% homologous.

In another embodiment, a polypeptide of this invention has an amino acid residue sequence comprising a sequential subset of the EPR-1 protein. In one variation, the polypeptide is a protein having a molecular weight of about 62–74 kDa. Preferably, the polypeptide or protein also binds to an anti-EPR-1 antibody; most preferably, the polypeptide or protein has an amino acid residue sequence at least 75% homologous to that identified herein as SEQ ID NO 2. More preferably, they are at least 85% homologous; even more preferably, they are at least 90% homologous; most preferably, they are at least 95% homologous to the protein identified herein as SEQ ID NO 2.

A polypeptide of the present invention can be used to generate a variety of useful antibodies by means described herein. Additionally, a polypeptide of the present invention may be used in competitive assays—e.g., to compete with EPR-1 for binding to an anti-EPR-1 antibody. Alternatively, a polypeptide of the present invention may be used to generate antibodies (or fragments thereof) to various portions of, or epitopes on, EPR-1.

In addition, a polypeptide of the present invention may be used to inhibit or disrupt T cell proliferation via binding to or occupying the receptor (i.e., counter-receptor) to which an EPR-1 receptor molecule would typically bind—that is, such a polypeptide would compete with EPR-1 for binding to the counter-receptor. The various utilities of the polypeptides noted herein will further be apparent from the discussion provided hereinbelow.

Typically an instant polypeptide is not glycosylated, i.e., it is synthesized either directly by standard peptide synthesis techniques or by procaryotic host expression of a recombinant DNA molecule of the present invention. A eucaryotically produced polypeptide of the present invention is typically glycosylated.

An instant polypeptide can incorporate a variety of changes, such as insertions, deletions, and substitutions of amino acid residues which are either conservative or nonconservative, as long as the resulting polypeptide molecule exhibits the desired properties. The "desired properties" as referred to herein include that the polypeptide is immunogenic in a suitable host and able to generate antibodies to the EPR-1 molecule or a polypeptide homologous to at least a portion of EPR-1, at least in the denatured state as is found in an SDS-PAGE gel, but preferably, also in the "natural" or "native" state (i.e., the state in which EPR-1 is expressed on cells). An additional desired property is that the polypeptide is antigenic when expressed on cells or in its denatured state so that antibodies immunoreactive with the EPR-1 molecule also immunoreact with the instant polypeptide.

When an instant polypeptide incorporates conservative substitutions of the sequences corresponding to EPR-1 as discussed herein, the substituted amino acid residues are preferably replaced by another, biologically similar amino acid residue such that the resulting polypeptide has an amino acid residue sequence that is different from (i.e., is less than 50% homologous to) a sequence of factor V, factor VIII or sequence MFG E-8. Some examples of conservative substitutions include substitution of a hydrophobic residue such as isoleucine, valine, leucine or methionine for another hydrophobic residue. Also, a polar residue such as arginine, glycine, glutamic acid, aspartic acid, glutamine, asparagine, and the like, can be conservatively substituted for another member of this group. Still another aspect of a polypeptide incorporating conservative substitutions occurs when a substituted amino acid residue replaces an unsubstituted parent amino acid residue. Examples of substituted amino acids may be found at 37 C.F.R. §1.822(b) (4), which species are incorporated herein by reference. When the polypeptide has an amino acid residue sequence that corresponds to the sequence of EPR-1 but has one or more conservative substitutions, preferably no more than about 40%, more preferably not more than about 30%, and even more preferably no more than about 20%, of the amino acid residues of the native protein are substituted. Polypeptides having no more than about 5–10% conservative substitutions are even more preferred.

A polypeptide of the present invention can be synthesized by any of the peptide synthetic techniques known to those skilled in the art. A summary of some of the techniques available can be found in J. M. Stuard and J. D. Young, "Solid Phase Peptide Synthesis", W.H. Freeman, Co., San Francisco (1969); J. Meinhofer, "Hormonal Proteins and Peptides" Vol. 2, pp. 46, Academic Press (New York) 1983; E. Schroder and K. Kubke, "The Peptides", Vol. 1, Academic Press (New York), 1965 for classical solution synthesis, and U.S. Pat. No. 4,631,211, the disclosures of which are incorporated herein by reference. When a polypeptide desired for use according to the present invention is relatively short (i.e., less than about 50 amino acid residues in length) direct peptide synthetic techniques are generally favored, usually by employing a solid phase technique such as that of Merrifield (*JACS* 85: 2149 (1963)). Appropriate protective groups usable in the aforementioned syntheses are described in the above texts and in J. F. W. McOmie, "Protective Groups in Organic Chemistry", Plenum Press, New York, 1973, which is incorporated herein by reference.

An instant polypeptide can also be synthesized by recombinant DNA techniques. Such recombinant techniques are favored especially when the desired polypeptide is relatively long (greater than about 50 amino acids residues in length). When recombinant DNA techniques are employed to prepare an instant polypeptide (see Section D hereinbelow), a DNA segment encoding the desired polypeptide is incorporated into a preselected vector that is subsequently expressed in a suitable host. The expressed polypeptide is then preferably purified by a routine method such as gel electrophoresis, immunosorbent chromatography, and the like.

Preferably, an EPR-1 polypeptide of this invention is further characterized by its ability to immunologically mimic an epitope (antigenic determinant) expressed by EPR-1. As used herein, the phrase "immunologically mimic" in its various grammatical forms refers to the ability of an EPR-1 polypeptide of this invention to immunoreact with an antibody of the present invention that immunoreacts with a native epitope of EPR-1 as defined herein.

It should be understood that a subject polypeptide need not be identical to the amino acid residue sequence of EPR-1, so long as it includes the required sequence and is able to affect lymphocyte proliferation, immunoreact with factor Xa, or immunoreact with an anti-EPR-1 antibody, as described herein.

A subject polypeptide includes any analog, fragment or chemical derivative of a polypeptide whose amino acid residue sequence is shown herein so long as the polypeptide is capable of immunoreacting with factor Xa or with an anti-EPR-1 antibody of the present invention. Therefore, a present polypeptide can be subject to various changes, substitutions, insertions, and deletions where such changes provide for certain advantages in its use. In this regard, an EPR-1 polypeptide of this invention corresponds to, rather than is identical to, a sequential subset of the EPR-1 sequence shown in FIG. 1, where one or more changes are made and it retains the ability to immunoreact with factor Xa or with an anti-EPR-1 antibody as described herein.

The term "analog" includes any polypeptide having an amino acid residue sequence substantially identical to a sequence specifically shown herein in which one or more residues have been conservatively substituted with a functionally similar residue and which displays the within-described abilities. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite inhibition activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine.

Also included as chemical derivatives are those peptides which contain one or more naturally occurring amino acid derivatives of the twenty standard amino acids. Examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained. As noted herein, polypeptides having an amino acid residue sequence 75–100% homologous to the EPR-1 sequence shown in FIG. 1 (SEQ ID NO 2) or a sequential subset thereof are especially preferred.

When a polypeptide of the present invention has a sequence that is not identical to the sequence of EPR-1 or a sequential subset thereof, it is typically because one or more conservative or non-conservative substitutions have been made, usually no more than about 30 number percent, and preferably no more than 10 number percent of the amino acid residues are substituted. Additional residues may also be added at either terminus of an EPR-1 polypeptide for the purpose of providing a "linker" by which the polypeptides of this invention can be conveniently affixed to a label or solid matrix, or carrier. Preferably, the linker residues do not form EPR-1 epitopes, i.e., are not similar in structure to EPR-1.

Amino acid residue linkers are usually at least one residue and can be 40 or more residues, more often 1 to 10 residues, but do not form EPR-1 epitopes. Typical amino acid residues used for linking are tyrosine, cysteine, lysine, glutamic and aspartic acid, or the like. In addition, a subject polypeptide can differ, unless otherwise specified, from the natural sequence of EPR-1 by the sequence being modified by terminal-$NH_2$ acylation, e.g., acetylation, or thioglycolic acid amidation, by terminal-carboxlyamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification.

When coupled to a carrier to form what is known in the art as a carrier-hapten conjugate, an EPR-1 polypeptide of the present invention is capable of inducing antibodies that immunoreact with EPR-1. In view of the well established principle of immunologic cross-reactivity, the present invention therefore contemplates antigenically related variants of the polypeptides disclosed herein. An "antigenically related variant" is a subject polypeptide that is capable of inducing antibody molecules that immunoreact with homologous polypeptides and preferably with EPR-1.

Any peptide of the present invention may also be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

An EPR-1 polypeptide can be used, inter alia, in the diagnostic methods and systems of the present invention. An EPR-1 polypeptide can also be used to prepare an inoculum as described herein for the preparation of antibodies that immunoreact with epitopes on EPR-1. In addition, an EPR-1 polypeptide can be used in vitro to inhibit the inactivation of Factor VIII or Factor V during procedures for purifying those factors as described herein. An EPR-1 polypeptide of this invention can also be used in the therapeutic methods of the present invention as disclosed hereinbelow.

D. Nucleic Acid Molecules

DNA segments (i.e., synthetic oligonucleotides) that encode EPR-1 can easily be synthesized by chemical techniques, for example, the phosphotriester method of Matteucci, et al., (*J. Am. Chem. Soc.* 103: 3185–3191 (1981)) or via using automated synthesis methods. In addition, larger DNA segments can readily be prepared by well known methods, such as synthesis of a group of oligonucleotides that define the DNA segment, followed by hybridization and ligation of oligonucleotides to build the complete segment.

Of course, by chemically synthesizing the coding sequence, any desired modifications can be made simply by substituting the appropriate bases for those encoding the native amino acid residue sequence.

Furthermore, DNA segments consisting essentially of structural genes encoding EPR-1 can be obtained from recombinant DNA molecules containing a gene that defines EPR-1, and can be subsequently modified, as by site directed mutagenesis, to introduce the desired substitutions.

The present invention thus includes a variety of novel and useful nucleic acid molecules. In one embodiment, a nucleic acid molecule according to the present invention encodes a protein homologous to the protein identified herein as SEQ ID NO 2. In another embodiment, a nucleic acid molecule according to the present invention comprises the DNA sequence illustrated in FIG. 1, identified herein as SEQ ID NO 1. In alternative embodiments, a nucleic acid sequence may comprise one or more sequential subsets of the molecule identified herein as SEQ ID NO 1, or may comprise a molecule encoding a polypeptide comprising one or more sequential subsets of the polypeptide identified herein as SEQ ID NO 2.

Still other preferred nucleic acid molecules comprise nucleic acid molecules encoding an amino acid residue sequence identical to, or at least 75% homologous to, an EPR-1 protein identified herein as SEQ ID NO 2 or a sequential subset thereof. In one embodiment, a nucleic acid molecule encodes a polypeptide or protein about 500–1000 amino acid residues in length. More preferably, the nucleic acid molecule encodes a polypeptide or protein of about 100–500 amino acids in length. Even more preferably, the nucleic acid molecule encodes a polypeptide or protein about 200–350 amino acids in length.

In other preferred embodiments, a nucleic acid molecule according to the present invention encodes a chimeric protein, a fusion protein, or a conjugate, wherein the amino acid sequence encoded by said nucleic acid molecule includes the sequence identified herein as SEQ ID NO 2, or a sequential subset thereof. In still other embodiments, the amino acid sequence encoded by said nucleic acid molecule is 75–100% homologous to SEQ ID NO 2, or a sequential subset thereof.

An especially preferred nucleic acid molecule of the present invention comprises a DNA molecule encoding a protein at least 75% homologous to the protein represented by SEQ ID NO 2. More preferably, a DNA (or nucleotide) molecule of the present invention encodes a protein that is 75–100% homologous to the protein identified herein as SEQ ID NO 2.

As noted hereinabove, proteins and polypeptides of the present invention may be synthesized (or otherwise modified) using recombinant techniques. Albeit DNA constructs are described herein as exemplary, it is expressly to be understood that RNA molecules are also contemplated for use as disclosed herein. For example, a protein or polypeptide of the present invention may be prepared and expressed as described in Example 4 hereinbelow.

When recombinant techniques are employed to prepare a polypeptide of the present invention, a nucleic acid (e.g., DNA) molecule or segment encoding the polypeptide is preferably used. A preferred DNA molecule contemplated by the present invention is operatively linked to a vector that is subsequently expressed in a suitable host. The molecule is "operatively linked" to the vector as used herein when it is ligated (covalently bound) thereto, according to common usage. The present invention also encompasses RNA molecules equivalent to the instantly-disclosed DNA molecules.

Nucleic acid molecules according to the present invention may readily be synthesized via chemical techniques, e.g., by the well-known phosphotriester method. (See, e.g., Matteuci et al., *JACS* 103: 3185 (1981).) By chemically synthesizing nucleic acid molecules, any desired substitution, insertion or deletion of an amino acid residue or sequence from a template polypeptide, e.g., the native protein, can be readily provided by simply making the corresponding changes in the nucleotide sequence of the DNA molecule.

Whenever an RNA molecule encoding a polypeptide of the present invention is used, the RNA molecule including the polypeptide coding molecule is transcribed into complementary DNA (cDNA) via a reverse transcriptase. The cDNA molecule can then be transcribed and translated as described herein to generate a desired polypeptide.

In a preferred aspect of the invention, a DNA nucleotide sequence (molecule) encoding at least one of the amino acid residue sequences of EPR-1 identified herein (e.g., SEQ ID NO 2) is operatively linked to a larger DNA molecule. The resultant DNA molecule is then transformed or transfected into a suitable host and expressed therein.

A nucleic acid molecule encoding an amino acid residue sequence according to the present invention can be provided with start and stop codons, or one or both of the start and stop codons can be provided by a larger nucleic acid molecule (e.g., a vector) operatively linked to the nucleic acid molecule so that only the corresponding polypeptide is generated. Alternatively, a nucleic acid sequence encoding additional amino acid residues can be provided at the 3' and/or 5' ends of the nucleic acid molecule so that a larger polypeptide is expressed having an amino acid residue sequence at either or both of its N-terminal and C-terminal ends in addition to an amino acid residue sequence of (or derived from) the EPR-1 molecule.

Another set of DNA molecules of the present invention encode a polypeptide having an amino acid residue sequence including the 2E1 monoclonal antibody epitope, which is represented by the formula ADCVSPPCGERDRCEG-WADRHTACSSPAS (SEQ ID NO 3) corresponding to the mAb 2E1 epitope on EPR-1. Preferably, the nucleotide molecule encodes a polypeptide of about 5–100 amino acid residues in length, more preferably about 4–50 amino acids in length, and even more preferably, about 3–30 amino acids in length.

A nucleic acid molecule according to the present invention may be produced by enzymatic techniques. Thus, restriction enzymes which cleave nucleic acid molecules at predefined recognition sequences can be used to isolate nucleic acid fragments from larger nucleic acid molecules containing the desired nucleic acid molecules such as the DNA (or RNA) that codes for the EPR-1 protein. Typically, DNA fragments produced in this manner will have cohesive, "overhanging" termini, in which single-stranded nucleic acid sequences extend beyond the double-stranded portion of the molecule. The presence of such cohesive termini is generally preferred over blunt-ended DNA molecules. The isolated fragments containing the desired coding sequence can then be ligated (cloned) into a suitable vector for amplification and expression.

Using PCR, it is possible to synthesize useful polypeptide-encoding nucleotide sequences which may then be operatively linked to a vector and used to transform or transfect an appropriate cell and expressed therein.

Particularly preferred methods for producing large quantities of recombinant EPR-1 polypeptides and proteins of the present invention rely on the use of preselected oligonucleotides as primers in a polymerase chain reaction (PCR) to form PCR reaction products as described herein.

If the DNA products described above are to be produced by (PCR) amplification, two primers, i.e., a PCR primer pair, must be used for each coding strand of nucleic acid to be amplified. The first primer becomes part of the nonsense (minus or complementary) strand and hybridizes to a nucleotide sequence conserved among the preferred gene's plus (or coding) strands. To produce coding DNA homologs, first primers are therefore chosen to hybridize to (i.e. be complementary to) conserved regions within the gene(s) of choice.

Second primers become part of the coding (plus) strand and hybridize to a nucleotide sequence conserved among minus strands. To produce the coding DNA homologs, second primers are therefore chosen to hybridize with a conserved nucleotide sequence at the 5' end of the coding gene such as in that area coding for the leader or first framework region. It should be noted that in the amplification of the coding DNA homologs the conserved 5' nucleotide sequence of the second primer can be complementary to a sequence exogenously added using terminal deoxynucleotidyl transferase as described by Loh et al., *Science* 243: 217–220 (1989). One or both of the first and second primers can contain a nucleotide sequence defining an endonuclease recognition site (restriction site). The site can be heterologous to the gene being amplified and typically appears at or near the 5' end of the primer.

The first primer of a PCR primer pair is sometimes referred to herein as the "sense primer" because it hybridizes to the coding or sense strand of a nucleic acid. In addition, the second primer of a PCR primer pair is sometimes referred to herein as the "antisense primer" because it hybridizes to a non-coding or antisense strand of a nucleic acid, i.e., a strand complementary to a coding strand. A plurality of first primers and/or a plurality of second primers can be used in each amplification, e.g., one species of first primer can be paired with a number of different second primers to form several different primer pairs. Alternatively, an individual pair of first and second primers can be used. Primers are also referred to as being either 5' or 3' primers indicating the ends or region of the DNA to which the primers hybridize. In this case, the 5' and 3' primers are respectively the antisense and sense primers.

When present, the restriction site-defining portion is typically located in a 5'-terminal non-priming portion of the primer. The restriction site defined by the first primer is typically chosen to be one recognized by a restriction enzyme that does not recognize the restriction site defined by the second primer, the objective being to produce a DNA molecule having cohesive termini that are non-complementary to each other and thus allow directional insertion into a vector.

In PCR, each primer works in combination with a second primer to amplify a target nucleic acid sequence. The choice of PCR primer pairs for use in PCR is governed by various considerations, as discussed herein. That is, the primers have a nucleotide sequence that is complementary to a sequence conserved in the gene of choice. Useful priming sequences are disclosed hereinafter.

The strategy used for cloning the selected genes will depend, as is well known in the art, on the type, complexity, and purity of the nucleic acids making up the various genes. Other factors include whether or not the genes are to be amplified and/or mutagenized.

In general, the exemplary genes are comprised of polynucleotide coding strands, such as mRNA and/or the sense strand of genomic DNA. If the polynucleotide sequence is in the form of double stranded genomic DNA, it is usually first denatured, typically by melting, into single strands. A gene sequence is subjected to a PCR reaction by treating (contacting) the sequence with a PCR primer pair, each member of the pair having a preselected nucleotide sequence. The PCR primer pair is capable of initiating primer extension reactions by hybridizing to nucleotide sequences, preferably at least about 10 nucleotides in length and more preferably at least about 20 nucleotides in length, conserved within the gene sequence.

In using PCR technology herein, a DNA primer molecule encoding one or more of the aforementioned amino acid residue sequences (e.g., SEQ ID NO 2) is preferably utilized. However, additional nucleotide sequences can be utilized or revealed by cloning the cDNA or genomic DNA encoding EPR-1 and smaller amino acid residue sequences thereof. A DNA probe molecule encoding an EPR-1 amino acid residue sequence identical to or derived from (e.g., a sequential subset of) an EPR-1 amino acid residue sequence such as that of FIG. 1 (SEQ ID NO 2) is preferred. One preferred DNA molecule comprises the DNA sequence illustrated in FIG. 1 (SEQ ID NO 1).

It should also be understood that the use of mixed, redundant primers that encode a targeted amino acid residue sequence utilizing different codons for the same amino acid residue is also contemplated.

The PCR reaction is performed by mixing the PCR primer pair, preferably a predetermined amount thereof, with the nucleic acids of the selected gene or DNA nucleotide sequence, preferably a predetermined amount thereof, in a PCR buffer to form a PCR reaction admixture. The admixture is maintained under polynucleotide synthesizing conditions for a time period, which is typically predetermined, sufficient for the formation of a PCR reaction product, thereby producing a plurality of different polypeptide-encoding DNA homologs.

The PCR reaction is performed using any suitable method. Generally it occurs in a buffered aqueous solution, i.e., a PCR buffer, preferably at a pH of 7–9, most preferably about 8. Preferably, a molar excess (for genomic nucleic acid, usually about $10^6:1$ primer:template) of the primer is admixed to the buffer containing the template strand. A large molar excess is preferred to improve the efficiency of the process. The PCR buffer also preferably contains the deoxyribonucleotide triphosphates dATP, dCTP, dGTP, and dTTP and a polymerase, typically thermostable, all in adequate amounts for primer extension (polynucleotide synthesis) reaction. Thus, for example, the resulting solution (PCR admixture) is heated to about 90° C.–100° C. for about 1 to 10 minutes, preferably from 1 to 4 minutes. After this heating period the solution is allowed to cool to 54° C., which is preferable for primer hybridization. The synthesis reaction may occur at room temperature up to a temperature above which the polymerase (inducing agent) no longer functions efficiently. Thus, for example, if DNA polymerase is used as inducing agent, the temperature is generally no greater than about 40° C. An exemplary PCR buffer comprises the following: 50 mM KCl; 10 mM Tris-HCl at pH 8.3; 1.5 mM $MgCl_2$; 0.001% (wt/vol) gelatin, 200 $\mu$M dATP; 200 $\mu$M dTTP; 200 $\mu$M dCTP; 200 $\mu$M dGTP; and 2.5 units Thermus aquaticus DNA polymerase I (U.S. Pat. No. 4,889,818, the disclosures of which are incorporated by reference herein) per 100 microliters of buffer.

The inducing agent may be any compound or system which will function to accomplish the synthesis of primer extension products, including enzymes. Suitable enzymes for this purpose include, for example, E. coli DNA polymerase I, Klenow fragment of E. coli DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above.

The inducing agent also may be a compound or system which will function to accomplish the synthesis of RNA primer extension products, including enzymes. In preferred embodiments, the inducing agent may be a DNA-dependent RNA polymerase such as T7 RNA polymerase, T3 RNA polymerase or SP6 RNA polymerase. These polymerases produce a complementary RNA polynucleotide. The high turn-over rate of the RNA polymerase amplifies the starting polynucleotide as has been described by Chamberlin et al., *The Enzymes*, ed. P. Boyer, PP. 87–108, Academic Press, New York (1982). Another advantage of T7 RNA polymerase is that mutations can be introduced into the polynucleotide synthesis by replacing a portion of cDNA with one or more mutagenic oligodeoxynucleotides (polynucleotides) and transcribing the partially-mismatched template directly as has been previously described by Joyce et al., *Nuc. Acid Res.* 17: 711–722 (1989). Amplification systems based on transcription have been described by Gingeras et al., in *PCR Protocols, A Guide to Methods and Applications*, pp 245–252, Academic Press, Inc., San Diego, Calif. (1990).

If the inducing agent is a DNA-dependent RNA polymerase and therefore incorporates ribonucleotide triphosphates, sufficient amounts of ATP, CTP, GTP and UTP are admixed to the primer extension reaction admixture and the resulting solution is treated as described above. The newly synthesized nucleic acid strand and its complementary strand form a double-stranded molecule which can be used in the succeeding steps of the process.

After producing various polypeptide-encoding DNA homologs for one or a plurality of different genes or DNA molecules, the DNA molecules are typically further amplified. While the DNA molecules can be amplified by classic techniques such as incorporation into an autonomously replicating vector, it is preferred to first amplify the molecules by subjecting them to a polymerase chain reaction (PCR) prior to inserting them into a vector. PCR is typically carried out by thermocycling i.e., repeatedly increasing and decreasing the temperature of a PCR reaction admixture within a temperature range whose lower limit is about 10° C. to about 40° C. and whose upper limit is about 90° C. to about 100° C. The preferred amplification procedure was performed as described in Example 1. The increasing and decreasing can be continuous, but is preferably phasic with time periods of relative temperature stability at each of temperatures favoring polynucleotide synthesis, denaturation and hybridization.

PCR amplification methods are described in detail in U.S. Pat. Nos. 4,683,192, 4,683,202, 4,800,159, 4,683,195 and 4,965,188 (the disclosures of which are incorporated by reference herein), and at least in several texts including "PCR Technology: Principles and Applications for DNA Amplification", H. Erlich, ed., Stockton Press, New York (1989); and "PCR Protocols: A Guide to Methods and Applications", Innis et al., eds., Academic Press, San Diego, Calif. (1990). Various preferred methods and primers for use as disclosed herein are also described in Nilsson, et al., *Cell* 58: 707 (1989), Ennis, et al., *PNAS USA* 87: 2833–7 (1990), and Zemmour, et al., *Immunogenetics* 33: 310–20 (1991), for example.

In particular, for amplifying nucleotide sequences for use in this invention, it is preferred to design primers from comparison of 5' and 3' untranslated regions of known allelic forms (if any), with selection of conserved sequences. Restriction sites may also be incorporated into the 5' and 3' primers to enable the amplification products to be subcloned into sequencing or expression vectors. It may also be helpful to place a 4-base spacer sequence proximal to the restriction site to improve the efficiency of cutting amplification products with enzymes.

In preferred embodiments only one pair of first and second primers is used per amplification reaction. The amplification reaction products obtained from a plurality of different amplifications, each using a plurality of different primer pairs, are then combined. However, the present invention also contemplates DNA homolog production via co-amplification (using two pairs of primers), and multiplex amplification (using up to about 8, 9 or 10 primer pairs).

E. Vectors

Expression of recombinant EPR-1 polypeptides and proteins of this invention is accomplished through the use of expression vectors into which the PCR amplified EPR-1 sequences described above have been inserted. The expression vectors may be constructed utilizing any of the well-known vector construction techniques. Those techniques, however, are modified to the extent that the translatable nucleotide sequence to be inserted into the genome of the host cell is flanked "upstream" of the sequence by an appropriate promoter and/or enhancer sequence.

The choice of vector to which a nucleotide segment of the present invention is operatively linked depends directly, as is well known in the art, on the functional properties desired, e.g., protein expression, and the host cell to be transformed or transfected, these being limitations inherent in the art of constructing recombinant DNA molecules. However, a vector contemplated by the present invention is at least capable of directing the replication, and preferably also expression, of the beneficial protein structural gene included in DNA segments to which it is operatively linked.

Thus, the present invention contemplates a vector that can be operatively linked to a nucleic acid molecule of the present invention to provide a self-replicating recombinant DNA molecule that encodes an instantly-disclosed EPR protein or polypeptide, preferably expressing the EPR-1 protein identified herein as SEQ ID NO 2. A preferred DNA molecule has the sequence shown in FIG. 1, identified herein as SEQ ID NO 1.

The recombinant molecule can be used to transform or transfect suitable host cells so that the host cells express the desired polypeptide. Hence, a preferred nucleic acid molecule may be regarded as self-replicating.

The choice of vector to which a nucleic acid molecule of the present invention is operatively linked depends, as is well known in the art, on the functional properties desired, e.g., efficiency of expression, the transformation or transfection host cell, and the like. However, a vector of the present invention is at least capable of directing the replication, and preferably also expression, of a nucleic acid molecule encoding an instant polypeptide or protein.

In many preferred embodiments, the vector also contains a selectable marker. After expression, the product of the translatable nucleotide sequence may then be purified using antibodies against that sequence. One example of a selectable marker is neomycin resistance. A plasmid encoding neomycin resistance, such as *phshsneo, phsneo*, or *pcopneo*, may be included in each transfection such that a population of cells that express the gene(s) of choice may be ascertained by growing the transfectants in selection medium.

In various embodiments, the translatable nucleotide sequence may be incorporated into a plasmid with an appropriate controllable transcriptional promoter, translational control sequences, and a polylinker to simplify insertion of the translatable nucleotide sequence in the correct orientation, and may be expressed in the host cells. Various host cells include a eucaryotic insect cell, such as *Spodoptera frugiperda*, or a procaryotic cell, such as *Escherichia coli*. Preferably, there are 5' control sequences defining a promoter for initiating transcription and a ribosome binding site operatively linked at the 5' terminus of the upstream translatable DNA sequence.

To achieve high levels of gene expression in transformed or transfected cells—for example, *E. coli*—it is necessary to use not only strong promoters to generate large quantities of mRNA, but also ribosome binding sites to ensure that the mRNA is efficiently translated. In *E. coli*, for example, the ribosome binding site includes an initiation codon (AUG) and a sequence 3–9 nucleotides long located 3–11 nucleotides upstream from the initiation codon (Shine et al., *Nature*, 254: 34 (1975)). The sequence, AGGAGGU, which is called the Shine-Dalgarno (SD) sequence, is complementary to the 3' end of *E. coli* 16S mRNA. Binding of the ribosome to mRNA and the sequence at the 3' end of the mRNA can be affected by several factors, including (1) the degree of complementarity between the SD sequence and 3' end of the 16S tRNA; and (2) the spacing and possibly the DNA sequence lying between the SD sequence and the AUG. (See, e.g., Roberts et al., *PNAS USA* 76: 760 (1979a); Roberts et al., *PNAS USA* 76: 5596 (1979b); Guarente et al., *Science* 209: 1428 (1980); and Guarente et al., *Cell* 20: 543 (1980).)

Optimization is generally achieved by measuring the level of expression of genes in plasmids in which this spacing is systematically altered. Comparison of different mRNAs shows that there are statistically preferred sequences from positions −20 to +13 (where the A of the AUG is position 0; see, e.g., Gold et al., *Ann. Rev. Microbiol.* 35: 365 (1981). Leader sequences have also been shown to influence translation dramatically (Roberts et al., 1979 a, b supra). Binding of the ribosome may also be affected by the nucleotide sequence following the AUG, which affects ribosome binding. (See, e.g., Taniguchi et al., *J. Mol. Biol.* 118: 533 (1978).)

Vectors for use in producing large quantities of the recombinant polypeptides and proteins of this invention may be designed for the expression of proteins in bacteria, in mammalian cells or in insect cells. For expression in bacterial *E. coli*, the expression vectors are preferably utilized in conjunction with bacterial "host" cells adapted for the production of useful quantities of proteins or polypeptides. Such vectors may include a procaryotic replicon i.e., a nucleotide sequence having the ability to direct autonomous replication and maintenance of the recombinant DNA molecule extra-chromosomally in a procaryotic host cell, such as a bacterial host cell, transformed therewith. Such replicons are well known in the art. In addition, those embodiments that include a procaryotic replicon may also include a gene whose expression confers a selective advantage, such as drug resistance, to a bacterial host transformed therewith. Typical bacterial drug resistance genes are those that confer resistance to ampicillin or tetracycline. Vectors typically also contain convenient restriction sites for insertion of translatable nucleotide sequences.

The procaryotic expression vectors also contain promoters which can be used in the microbial organism for expression of its own proteins. Those promoters most commonly used include the beta-lactamase and lactose promoter systems and the tryptophan promoter system as described in the European Patent Application No. 0125023, the relevant disclosures of which are incorporated by reference herein.

Promoter sequences compatible with bacterial hosts, such as a tac promoter, are typically provided in plasmid vectors having convenient restriction sites for insertion of a DNA molecule of the present invention. Promoter sequences compatible with bacterial hosts are typically provided in plasmid vectors containing convenient restriction sites for insertion of a DNA segment of the present invention. Exemplary procaryotic expression vectors include the plasmids pUC8, pUC9, pUC18, pBR322, and pBR329 available from Bio-Rad Laboratories (Richmond, Calif.), pPL and pKK223 available from Pharmacia (Piscataway, N.J.), and pBS, M13mp19, pNH8a, pNH16A, pNH18a, and pNH46a (Stratagene, La Jolla, Calif.). Other exemplary vectors include pCMU (Nilsson, et al., *Cell* 58: 707 (1989)).

Other appropriate vectors may also be synthesized, according to known methods; for example, vectors pCMU/$K^b$ and pCMUII are modifications of pCMUIV (Nilsson, et al., supra).

Expression vectors compatible with eucaryotic cells, preferably those compatible with mammalian cells, can also be used to form the recombinant DNA molecules for use in the present invention. Mammalian cell expression vectors are well known in the art and are available from several commercial sources. Typically, such vectors are provided containing convenient restriction sites for insertion of the desired DNA segment, and provide the signals required for gene expression in a mammalian cell. Typical of such vectors are the pREP series vectors and pEBVhis available from Invitrogen (San Diego, Calif.), the vectors PTDT1 (ATCC #31255), pCP1 (ATCC #37351) and pJ4W (ATCC #37720) available from the American Type Culture Collection (ATCC) and the like mammalian expression vectors.

Exemplary cloning and expression vector systems for use according to the within-described methods include those described in Section B and Example 4 herein. For example, the Lambda ZAP II vector and the pBluescript SK−phagemid (Stratagene, La Jolla, Calif.) may be used in the construction of the cDNA library, as well as in subsequent cloning and expression steps.

Successfully transformed or transfected cells, i.e., cells that contain a rDNA molecule of the present invention, can be identified by well known techniques. For example, cells resulting from the introduction of an rDNA of the present invention can be subjected to assays for detecting the presence of specific rDNA using a nucleic acid hybridization method such as that described by Southern, *J. Mol. Biol.*, 98:503 (1975) or Berent et al., *Biotech.*, 3:208 (1985).

In addition to directly assaying for the presence of rDNA, successful transformation or transfection can be confirmed by well known immunological methods for the presence of expressed protein. For example, cells successfully transformed or transfected with an expression vector produce proteins which then can be assayed directly by immunological methods or for the presence of the function of the expressed protein.

It will be understood that this invention, although described herein in terms of various preferred embodiments, should not be construed as limited to the host cells, expression vectors and expression vectors systems exemplified. Other expression vector systems, well known to one of ordinary skill in the art and described by Kaufman, et al., in *Current Protocols in Molecular Biology*, Ausubel et al., eds., Unit 16, New York (1990), are contemplated for preparing recombinant EPR-1 polypeptides and proteins for use in this invention.

Expression vectors compatible with eucaryotic cells, preferably those compatible with vertebrate cells, can also be used to form a recombinant DNA molecule as described above. Eucaryotic cell expression vectors are well known in the art and are available from several commercial sources. Typically, such vectors are provided with convenient restriction sites for insertion of the desired DNA molecule. Typical of such vectors are pSVL and pKSV-10 (Pharmacia), pBPV-1pML2 d (International Biotechnologies, Inc.), pXT1 and pSG5 (Stratagene, La Jolla, Calif.) and pTDT1 (ATCC, #31255). A preferred drug resistance marker for use in vectors compatible with eucaryotic cells is the neomycin phosphotransferase (neo) gene. (Southern et al., *J. Mol. Appl. Genet.*, 1:327–341 (1982)).

Mammalian expression vector systems are also contemplated for the expression of recombinant polypeptides and proteins for use in this invention. For controlling expression in mammalian cells, viral-derived promoters are most commonly used. For example, frequently used promoters include polyoma, adenovirus type 2, and Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 base pair sequence extending from the Hind III restriction site toward the Bgl I site located in the viral origin of replication. Also contemplated is using the promoter sequences normally associated with the desired sequence for expression. Origins of replication may be provided either by construction of the vector to include an exogenous origin, such as may be derived from SV40 or other viral sources such as polyoma and adenovirus or may be provided by the host cell chromosomal replication mechanism. The latter is sufficient for integration of the expression vector in the host cell chromosome.

Retroviral expression vectors capable of generating the recombinant DNA of the present invention are also contemplated. The construction and use of retroviral vectors for generating desired DNA molecules have been described by Sorge, et al., *Mol. Cell. Biol.*, 4: 1730–37 (1984).

A number of methods are available to operatively link DNA to vectors via complementary cohesive termini. For instance, complementary homopolymer tracts can be added to the DNA molecule to be inserted and to the vector DNA. The vector and DNA molecule are then allowed to hybridize by hydrogen bonding between the complementary homopolymer tails to form recombinant duplex DNA molecules.

Alternatively, synthetic linkers containing one or more restriction sites can be used to join the DNA molecule to vectors. When the DNA molecule is generated by endonuclease restriction digestion, as described earlier, it is treated with bacteriophage T4 DNA polymerase of *E. coli* DNA polymerase I which removes protruding 3' single-stranded termini and fills in recessed 3' ends. Blunt-ended DNA molecules are thereby generated.

Blunt-ended DNA molecules are incubated with a large molar excess of linker molecules in the presence of an enzyme that is able to catalyze the ligation of blunt-ended DNA molecules, such as bacteriophage T4 DNA ligase. Thus, the products of the reaction are DNA molecules bonded at their ends to linker sequences having restriction sites therein. The restriction sites of these DNA molecules are then cleaved with the appropriate restriction enzyme and the molecules ligated to an expression vector having termini compatible with those of the cleaved DNA molecule. Synthetic linkers containing a variety of restriction endonuclease sites are commercially available from a number of sources including International Biotechnologies, Inc. (New Haven, Conn.).

F. Transformation/Transfection of Hosts

The present invention also relates to host cells transformed or transfected with a recombinant DNA molecule of the present invention. The host cell can be either procaryotic or eucaryotic. Preferred procaryotic host cells are strains of *E. coli*, e.g., the *E. coli* strain DH5 available from Bethesda Research Laboratories, Inc., Bethesda, Md. Preferred eucaryotic host cells include yeast and mammalian cells, preferably vertebrate cells such as those from mouse, rat, monkey or human fibroblastic cell line. Preferred eucaryotic host cells also include Chinese hamster ovary (CHO) cells, such as those available from the ATCC as CCL61, and NIH Swiss mouse embryo cells NIH/3T3 available from the ATCC as CRL 1658.

Transformation or transfection of appropriate cell hosts with a recombinant DNA molecule of the present invention is accomplished by well known methods that typically depend on the type of vector used. With regard to transformation of procaryotic host cells, see, for example, Maniatis et al., *Molecular Cloning, A Laboratory Manual*, Cold Spring Harbor Laboratory, Cold Spring Harbor, N.Y. (1982). With regard to transfection of vertebrate cells with retroviral vectors containing RNA encoding the instant polypeptides and a reverse transcriptase, see, e.g., Sorge et al., *Mol. Cell. Biol.*, 4: 1730–37 (1984).

Successfully transformed or transfected cells, i.e., those containing a recombinant DNA molecule of the present invention, can be identified by well known techniques. For example, transformed or transfected cells can be cloned to produce monoclonal colonies. Cells from those colonies can be harvested, lysed and their DNA content examined for the presence of the desired DNA molecule using a method such as that described by Southern, *J. Mol. Biol.*, 98: 503 (1975).

In addition to directly assaying for the presence of the desired DNA molecule, successful transformation or transfection can be confirmed by well known immunological methods when the DNA directs expression of the polypeptides of the present invention. Samples of cells suspected of being transformed or transfected are harvested and assayed for antigenicity by antibodies that specifically bind to the instant polypeptides.

In addition to the transformed or transfected host cells themselves, also contemplated by the present invention are cultures of those cells. Nutrient media useful for culturing transformed or transfected host cells are well known in the art and can be obtained from several commercial sources. In embodiments wherein the host cell is mammalian a "serum-free" medium is preferably used.

Methods for recovering an expressed protein from a culture are well known in the art. For instance, gel filtration, gel chromatography, ultrafiltration, electrophoresis, ion exchange, affinity chromatography and related techniques can be used to isolate the expressed proteins found in the culture. In addition, immunochemical methods, such as immunoaffinity, immunoadsorption, and the like, can be performed using well known methods, as exemplified by the methods described herein.

G. Hybridomas and Antibody Compositions

1. Hybridomas

Hybridomas of the present invention are those which are characterized as having the capacity to produce an antibody, including a monoclonal antibody, of the present invention.

Methods for producing hybridomas producing (secreting) antibody molecules having a desired immunospecificity, i.e., having the ability to immunoreact with a particular protein, an identifiable epitope on a particular protein and/or a polypeptide, are generally well known in the art. For example, useful methods are described by Niman et al., *Proc. Natl. Acad. Sci. USA*, 80: 4949–4953 (1983), and by Galfre et al., *Meth. Enzymol.*, 73: 3–46 (1981). Other methods are described in U.S. Pat. Nos. 5,180,806, 5,114,842, 5,204,445, and RE 32,011, the disclosures of which are incorporated by reference herein.

A hybridoma cell is typically formed by fusing an antibody-producing cell and a myeloma or other self-perpetuating cell line. Such a procedure was described by Kohler and Milstein, *Nature* 256: 495–497 (1975). A particularly preferred hybridoma is designated 12H1 (ATCC Accession No. HB 10637). Other preferred hybridomas include those designated as 2C11, 2D4, 2E1, 3H7, 3G8, 3G10, and 6F1.

Typically, hybridomas of the present invention are produced by using, in the above techniques as an immunogen, a substantially pure EPR-1 protein, EPR-1 homolog, or EPR-1 polypeptide of the present invention. Methods of generating antibodies via preparation of hybridomas are further described in Subsection 3 below.

2. Inocula

In another embodiment, a protein or polypeptide of this invention, an antigenically related variant thereof, or a protein or polypeptide at least 75% homologous to at least a portion of the EPR-1 protein identified herein as SEQ ID NO 2 is used in a pharmaceutically acceptable aqueous diluent composition to form an inoculum that, when administered in an effective amount, is capable of inducing antibodies that immunoreact with an EPR-1 protein or polypeptide.

The word "inoculum" in its various grammatical forms is used herein to describe a composition containing an EPR-1 protein or polypeptide of this invention as an active ingredient used for the preparation of antibodies against an EPR-1 protein or polypeptide.

When a polypeptide is used to induce antibodies it is to be understood that the polypeptide can be used alone, or linked to a carrier as a conjugate, or as a polypeptide polymer, but for ease of expression, the various embodiments of the polypeptides of this invention are collectively referred to herein by the term "polypeptide", and its various grammatical forms.

For a polypeptide that contains fewer than about 35 amino acid residues, it is preferable to use the peptide bound to a carrier for the purpose of inducing the production of antibodies as already noted.

As previously noted, one or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used. Exemplary additional linking procedures include the use of Michael addition reaction products, di-aldehydes such as glutaraldehyde, Klipstein et al., *J. Infect. Dis.*, 147, 318–326 (1983) and the like, or the use of carbodiimide technology as in the use of a water-soluble carbodiimide to form amide links to the carrier. For a review of protein conjugation or coupling through activated functional groups, see Aurameas, et al., *Scand. J. Immunol.*, Vol. 8, Supp-l. 7, 7–23 (1978).

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, and cholera toxoid, as well as polyamino acids such as poly (D-lysine: D-glutamic acid), and the like.

The choice of carrier is more dependent upon the ultimate use of the inoculum and is based upon various criteria. For example, a carrier that does not generate an untoward reaction in the particular animal to be inoculated should be selected.

The present inoculum contains an effective, immunogenic amount of an EPR-1 protein or polypeptide of this invention; as noted above, a smaller polypeptide may be used as a conjugate (i.e., linked to a carrier). The effective amount of polypeptide or protein per unit dose depends, among other things, on the species of animal inoculated, the body weight of the animal, and the chosen inoculation regimen as is well known in the art. Inocula typically contain polypeptide or protein concentrations of about 10 micrograms to about 500 milligrams per inoculation (dose), preferably about 50 micrograms to about 50 milligrams per dose.

The term "dose" or "unit dose" as it pertains to the inocula of the present invention refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared by dispersing a polypeptide, polypeptide-conjugate, or protein in a physiologically tolerable (acceptable) diluent or vehicle such as water, saline or phosphate-buffered saline to form an aqueous composition. For example, inocula containing EPR-1 protein are typically prepared from substantially pure EPR-1 protein by dispersion in the same physiologically tolerable diluents. Such diluents are well known in the art and are discussed, for example, in *Remington's Pharmaceutical Sciences*, 16th Ed., Mack Publishing Company, Easton, Pa. (1980) at pages 1465–1467.

Inocula may also include an adjuvant as a component of the diluent. Adjuvants such as complete Freund's adjuvant (CFA), incomplete Freund's adjuvant (IFA) and alum are materials well known in the art, and are available commercially from several sources.

3. Antibodies and Compositions

Also contemplated within the present invention is an antibody composition that immunoreacts with an instant protein or polypeptide. An antibody composition immunoreacts with the protein or polypeptide either associated with cellular surfaces or free from cellular structures. Thus, an antibody composition binds to one or more epitopes presented by the protein or polypeptide on the exterior surface of cells or to the epitopes of cell-free polypeptides or proteins.

A preferred antibody composition of the invention immunoreacts with an EPR-1 protein molecule presented on the cell surface or free of cellular components as when the EPR-1 molecule is isolated upon lysis of cells carrying the molecule. Particularly preferred antibody compositions in this regard are the monoclonal antibodies (mAbs) designated 7G12, 9D4, and 12H1. Such mAbs are obtained as described herein and in Altieri et al. *J. Biol. Chem.*, 264(5): 2969 (1989) and Altieri et al. *J. Immun.* 145: 246 (1990). Polyclonal antibodies are also contemplated. Briefly, a preferred antibody composition is generated by immunizing mice with human factor V, factor VIII or a polypeptide of this invention. The antibodies generated are screened for binding affinity for a polypeptide of the instant invention, such as EPR-1. Isolated EPR-1 or EPR-1 on washed lymphocytes free of factor V or factor VIII can be used for screening the antibodies.

Many of the instantly-disclosed mAbs immunoreact with both factor V and with EPR-1. However, when a polypeptide homologous but not identical to factor V is used to obtain the instant mAbs, the mAbs preferably immunoreact with the target polypeptide but not with factor V. Some of the disclosed mAbs may also be capable of immunoreacting with factor VIII proteins.

The antibodies of the present invention can bind to receptors for coagulation factor Xa—e.g., EPR-1. First-generation anti-EPR-1 antibodies and their homologs can be used to competitively inhibit factor Xa from binding to sites on cellular surfaces. Thus, the protease activity of factor Xa in the region of the cell surfaces can be curtailed. As a result, the present invention also contemplates methods for inhibiting the binding of factor Xa to EPR-1. The second-generation anti-EPR-1 antibodies disclosed herein, which inhibit lymphoproliferation but do not inhibit factor Xa binding, are also useful as disclosed herein.

A preferred antibody composition as contemplated herein is typically produced by immunizing a mammal with an inoculum containing human EPR-1 or a polypeptide of the present invention, thereby inducing in the mammal antibody molecules having the appropriate immunospecificity for the immunogenic polypeptide. The antibody molecules are then collected from the mammal, screened and purified to the extent desired using well known techniques such as, for example, immunoaffinity purification using the immunogen immobilized on a solid support. The antibody composition so produced can be used, inter alia, in the diagnostic methods and systems of the present invention to detect expression of the instant polypeptides on the surface of cells, e.g., leukocytes of patients with chronic lymphocytic leukemia (CLL).

A monoclonal antibody composition (mAb) is also contemplated by the present invention, as noted before. The phrase "monoclonal antibody composition" in its various grammatical forms refers to a population of antibody molecules that contain only one species of antibody combining site capable of immunoreacting with a particular antigen. The instant mAb composition thus typically displays a single binding affinity for any antigen with which it immunoreacts. However, a given monoclonal antibody composition may contain antibody molecules having two different antibody combining sites, each immunospecific for a different antigenic determinant, i.e., a bispecific monoclonal antibody.

An instant mAb is typically composed of antibodies produced by clones of a single cell (i.e., a hybridoma) that secretes (produces) one kind of antibody molecule. Preferred hybridomas and methods of preparing same are described herein and in subsection 1 above.

The present invention contemplates a method of forming a monoclonal antibody molecule that immunoreacts with an EPR-1 protein or polypeptide of the present invention, and optionally a factor V or VIII protein obtained from a mammal. The method comprises the steps of:

(a) Immunizing an animal with an EPR-1 protein or polypeptide of this invention or a protein homologous thereto, such as a factor V or VIII protein. Use of at least a portion of EPR-1 as the immunogen is preferred. The immunogen may be a protein taken directly from a subject animal species. However, the antigen can also be linked to a carrier protein such as keyhole limpet hemocyanin, particularly when the antigen is small, such as a polypeptide consisting essentially of a sequential subset of the amino acid residue sequence identified herein as SEQ ID NO 2. The immunization is typically performed by administering the sample to an immunologically competent mammal in an immunologically effective amount, i.e., an amount sufficient to produce an immune response. Preferably, the mammal is a rodent such as a rabbit, rat or mouse. The mammal is then maintained for a time period sufficient for the mammal to produce cells secreting antibody molecules that immunoreact with the immunogen.

(b) A suspension of antibody-producing cells removed from the immunized mammal is then prepared. This is typically accomplished by removing the spleen of the mammal and mechanically separating the individual spleen cells in a physiologically tolerable medium using methods well known in the art.

(c) The suspended antibody-producing cells are treated with a transforming agent capable of producing a transformed ("immortalized") cell line. Transforming agents and their use to produce immortalized cell lines are well known in the art and include DNA viruses such as Epstein-Barr virus (EBV), simian virus 40 (SV40), polyoma virus and the like, RNA viruses such as Moloney murine leukemia virus (MoMuLV), Rous sarcoma virus and the like, myeloma cells such as P3X63-Ag8.653, Sp2/O—Ag14 and the like.

In preferred embodiments, treatment with the transforming agent results in the production of an "immortalized" hybridoma by fusing the suspended spleen cells with mouse myeloma cells from a suitable cell line, e.g., SP-2, by the use of a suitable fusion promoter. The preferred ratio is about 5 spleen cells per myeloma cell in a suspension containing about $10^8$ splenocytes. A preferred fusion promoter is polyethylene glycol having an average molecule weight from about 1000 to about 4000 (commercially available as PEG 1000, etc.); however, other fusion promoters known in the art may be employed.

The cell line used should preferably be of the so-called "drug resistant" type, so that unfused myeloma cells will not survive in a selective medium, while hybrids will survive. The most common class is 8-azaguanine resistant cell lines, which lack the enzyme hypoxanthine-guanine phosphoribosyl transferase and hence will not be supported by HAT (hypoxanthine, aminopterin, and thymidine) medium. It is also generally preferred that the myeloma cell line used be of the so-called "non-secreting" type which does not itself produce any antibody. In certain cases, however, secreting myeloma lines may be preferred.

(d) The transformed cells are then cloned, preferably to monoclonality. The cloning is preferably performed in a tissue culture medium that does not sustain (support) non-transformed cells. When the transformed cells are hybridomas, this is typically performed by diluting and culturing in separate containers the mixture of unfused spleen cells, unfused myeloma cells, and fused cells (hybridomas) in a selective medium which will not sustain the unfused myeloma cells. The cells are cultured in this medium for a time sufficient to allow death of the unfused cells (about one week). The dilution can be a limiting dilution, in which the volume of diluent is statistically calculated to isolate a certain number of cells (e.g., 0.3–0.5) in each separate container (e.g., each well of a microtiter plate). The medium is one (e.g., HAT medium) that does not sustain the drug-resistant (e.g., 8-azaguanine resistant) unfused myeloma cell line.

(e) The tissue culture medium of the cloned transformants is analyzed (immunologically assayed) to detect the presence of antibody molecules that preferentially react with the instant EPR-1-related proteins or polypeptides or cells bearing the EPR-1 receptor molecule. This is accomplished using well known immunological techniques.

(f) A desired transformant is then selected and grown in an appropriate tissue culture medium for a suitable length of time, followed by recovery (harvesting) of the desired antibody from the culture supernatant by well known techniques. A suitable medium and length of culturing time are also well known or are readily determined.

To produce a much greater concentration of slightly less pure monoclonal antibody, the desired hybridoma can be transferred by injection into mice, preferably syngenic or semisyngenic mice. The hybridoma causes formation of antibody-producing tumors after a suitable incubation time, which results in a high concentration of the desired antibody (about 5–20 mg/ml) in the bloodstream and peritoneal exudate (ascites) of the host mouse.

Media and animals useful for the preparation of these compositions are both well known in the art and commercially available and include synthetic culture media, inbred mice and the like. An exemplary synthetic medium is Dulbecco's minimal essential medium (DMEM; Dulbecco et al., *Virol.* 8: 396 (1959)) supplemented with 4.5 gm/l glucose, 20 mM glutamine, and 20% fetal calf serum. A preferred inbred mouse strain is Balb/c.

Methods for producing the instant hybridomas which generate (secrete) the antibody molecules of the present invention are well known in the art and are described further herein. Particularly applicable descriptions of relevant hybridoma technology are presented by Niman et al., *Proc. Natl. Acad. Sci. USA*, 80: 4949–4953 (1983), and by Galfre et al., *Meth. Enzymol.*, 73: 3–46 (1981), which descriptions are incorporated herein by reference.

A monoclonal antibody can also be produced by methods well known to those skilled in the art of producing chimeric antibodies. Those methods include isolating, manipulating, and expressing the nucleic acid that codes for all or part of an immunoglobulin variable region including both the portion of the variable region comprising the variable region of immunoglobulin light chain and the portion of the variable region comprising the variable region of immunoglobulin heavy chain. Methods for isolating, manipulating, and expressing the variable region coding nucleic acid in procaryotic and eucaryotic hosts are disclosed in the following, the disclosures of which are incorporated by reference herein: Robinson et al., PCT Publication No. WO 89/0099; Winter et al., European Patent Publication No. 0239400; Reading, U.S. Pat. No. 4,714,681; Cabilly et al., European Patent Publication No. 0125023; Sorge et al., *Mol. Cell Biol.*, 4: 1730–1737 (1984); Beher et al., *Science*, 240: 1041–1043 (1988); Skerra et al., *Science*, 240: 1030–1041 (1988); and Orlandi et al., *Proc. Natl. Acad. Sci. U.S.A.*, 86: 3833–3837 (1989). Typically the nucleic acid codes for all or part of an immunoglobulin variable region that binds a preselected antigen (ligand). Sources of such nucleic acids are well known to one skilled in the art and, for example, can be obtained from a hybridoma producing a monoclonal antibody that binds the preselected antigen, or the preselected antigen can be used to screen an expression library coding for a plurality of immunoglobulin variable regions, thus isolating the nucleic acid.

A further preferred method for forming the instant antibody compositions involves the generation of libraries of Fab molecules using the method of Huse et al., *Science*, 246:

1275 (1989). In this method, mRNA molecules for heavy and light antibody chains are isolated from the immunized animal. The mRNAs are amplified using polymerase chain reaction (PCR) techniques. The nucleic acids are then randomly cloned into lambda phage to generate a library of recombined phage particles. The phage are used to infect an expression host such as E. coli. The E. coli colonies and corresponding phage recombinants can then be screened for those producing the desired Fab fragments. Preferred lambda phage vectors are λgt11 and λzap 2.

An antibody molecule-containing composition according to the present invention can take the form of a solution or suspension. The preparation of a composition that contains antibody molecules as active ingredients is well understood in the art. Typically, such compositions are prepared as liquid solutions or suspensions, however, solid forms suitable for solution in, or suspension in, liquid can also be prepared. The preparation can also be emulsified. The active therapeutic ingredient is often mixed with excipients which do not interfere with the assay and are compatible with the active ingredient. Suitable excipients are, for example, water, saline, dextrose, glycerol, ethanol, and the like, and combinations thereof. In addition, if desired, the composition may contain minor amounts of auxiliary substances such as wetting or emulsifying agents, pH buffering agents and the like, which enhance the effectiveness of the active ingredient.

An antibody molecule composition may further be formulated into a neutralized acceptable salt form. Acceptable salts include the acid addition salts (formed with the free amino groups of the antibody molecule) that are formed with inorganic acids such as, for example, hydrochloric or phosphoric acids, or such organic acids as acetic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

H. Diagnostic Assay Methods

The present invention contemplates a method for detecting an EPR-1 molecule, an EPR-1 homolog, or a polypeptide portion thereof. The assay may also be used to detect cell surface receptors homologous to EPR-1, as well as EPR-1 itself. The assay may be made specific for EPR-1 by a proper selection of antibody specificity. Also, an assay of the invention may be used to identify polypeptide receptors homologous to portions of EPR-1 as well as "free" receptors—i.e., polypeptides or proteins unassociated with any particular cell structure, polypeptides homologous to EPR-1, or polypeptide portions thereof. Typically, the assay methods involve detecting EPR-1 exposed on cell surfaces, such as on CLL cells, although assays for detecting EPR-1 proteins and polypeptides in unbound form—i.e., not bound to cell membranes—are also contemplated.

The relative binding affinity of a reagent molecule for its target species is conveniently determined as described herein using the method of flow microfluorometry (FMF). Thus, cells expressing the target antigen, e.g., EPR-1, are indicated whenever the fluorescence intensity associated with the cells due to binding of the instant fluorescent-labelled antibodies to cell surface antigens exceeds a predefined threshold level. The labelled antibodies are typically fluorescein isothiocyanate-conjugated (FITC), although other well known fluorescent labels may be used.

The method for detecting an antigenic protein or polypeptide of the present invention preferably comprises formation of an immunoreaction product between the protein or polypeptide and an anti-polypeptide antibody molecule, as disclosed herein. The antigen to be detected may be present in a vascular fluid sample or in a body tissue sample. The immunoreaction product is detected by methods well-known to those skilled in the art. Numerous clinical diagnostic chemistry procedures may be utilized to form the detectible immunocomplexes.

Alternatively, a protein or polypeptide ligand (non-antibody composition) for an instant EPR-1 receptor or polypeptide may be used in the assay method. An exemplary ligand in this aspect of the invention is a labelled factor Xa enzyme. Thus, while exemplary assay methods are described herein, the invention is not so limited.

A preferred assay method of the present invention involves determining the presence of EPR-1 cell surface receptors or soluble EPR-1 in a sample, and thereby ascertaining the level of EPR-1 expression in an individual or sample. Various heterogeneous and homogeneous assay protocols may be employed, either competitive or non-competitive for detecting the presence and preferably amount of cell surface receptors (e.g., EPR-1) in a body sample, preferably cell-containing sample. The assay protocols disclosed herein are capable of distinguishing an EPR-1 molecule or polypeptide portion thereof from factors V and VIII. A particularly preferred receptor for assay is EPR-1, identified herein as SEQ ID NO 2, expressed on CLL cells.

One useful method comprises admixing a body sample, preferably one obtained from a human donor or patient, containing cells and/or fluid to be analyzed with one of the within-described antibody compositions that are capable of immunoreacting with EPR-1 proteins or polypeptides. The cell sample may also be washed free of coagulation factors V and VIII prior to the admixing step. The immunoreaction admixture thus formed is maintained under appropriate assay conditions—e.g., biological assay conditions—for a time period sufficient for any cells expressing the antigen, or for any soluble antigen, to immunoreact with antibodies in the antibody composition to form an antibody-receptor immunocomplex. The immunoreaction product (immunocomplex) is then separated from any unreacted antibodies present in the admixture. The presence, and if desired, the amount of immunoreaction product formed is then determined. The amount of product formed may then be correlated with the amount of receptors expressed by the cells, or with the amount of soluble antigen expressed.

Determination of the presence or amount of immunoreaction product formed depends upon the method selected for identifying the product. For instance, a labelled antibody may be used to form a labelled immunocomplex with a receptor molecule of the present invention (e.g., EPR-1). The labelled immunocomplex may be quantitated by methods appropriate for detecting the respective label—e.g., fluorescent labels, radioactive labels, biotin labels and the like—as discussed hereinbelow. Alternatively, an unlabelled antibody may be used to form an unlabelled immunocomplex, which is subsequently detected by immunoreacting a labelled antibody recognizing the unlabelled antibody with the unlabelled immunocomplex. The immunocomplex thereby becomes labelled and may be detected as described above.

Biological conditions used in the instant assays are those that maintain the biological activity of the antibody, the EPR-1 cell surface molecule, and proteins or polypeptide molecules of this invention. Those conditions include a temperature range of about 4° C. to about 45° C., preferably about 37° C., at a pH value range of about 5 to about 9, preferably about 7, and an ionic strength varying from that of distilled water to that of about one molar sodium chloride, preferably about that of physiological saline. Methods for optimizing such conditions are well known in the art.

In a preferred embodiment, a body sample to be analyzed is withdrawn from a donor or patient and apportioned into aliquots. At least one aliquot is used for the determination of antigen expression using an antibody composition of the present invention. If desired, a second aliquot may be used for determining reactivity of a control antibody with the sample. The analyses may be performed concurrently but are usually performed sequentially.

In a further aspect of the invention, data obtained in the instant assays are recorded via a tangible medium, e.g., computer storage or hard copy versions. The data can be automatically input and stored by standard analog/digital (A/D) instrumentation that is commercially available. Also, the data can be recalled and reported or displayed as desired for best presenting the instant correlations of data. Accordingly, instrumentation and software suitable for use with the present methods are contemplated as within the scope of the present invention.

The antibody compositions and methods of the invention afford a method of monitoring treatment of patients afflicted with chronic lymphocytic leukemia (CLL), and other diseases in which expression of EPR-1 receptors is correlated with the disease state. For instance, it is found that the frequency of cells expressing an EPR-1 marker is inversely related to the response to treatment of patients suffering from CLL. Additionally, patients afflicted with hairy cell leukemia (HCL) of the EPR-1$^+$ type express markers detected by an instant antibody composition, thereby permitting monitoring of treatment.

Accordingly, a method of monitoring a patient's response to treatment is contemplated in which a marker for the disease is detectable and/or detected. The method comprises admixing a body sample containing cells to be assayed for EPR-1 marker with an antibody composition of the present invention, according to an assay method as described above. The admixture is maintained for a time period sufficient to form an immunoreaction product under predefined reaction conditions. The amount of immunoreaction product formed is correlated to an initial disease state. These steps are repeated at a later time during the treatment regimen, thereby permitting determination of the patient's response to treatment, with a decrease in the number of EPR-1 molecules expressed on cell surfaces indicating an improvement in the disease state.

I. Diagnostic Systems

Diagnostic systems for performing the described assays are also within the scope of the present invention. A diagnostic system of the present invention is preferably in kit form and includes, in an amount sufficient for at least one assay, a composition containing antibody molecules of the present invention (or fragments thereof) as a separately packaged reagent. The antibody molecules may be labelled, or a labeling reagent may be separately packaged and included within the kit, wherein the label is capable of indicating whether or not an immunoreaction product is present. Printed instructions providing guidance in the use of the packaged reagent(s) may also be included, in various preferred embodiments. The term "instructions" or "instructions for use" typically includes a tangible expression describing the reagent concentration or at least one assay method parameter, such as the relative amounts of reagent and sample to be admixed, maintenance time periods for reagent/sample admixtures, temperature, buffer conditions, and the like.

In one embodiment, a diagnostic system is contemplated for assaying for the presence of EPR-1 receptors expressed on cells in a cell-containing sample. In another embodiment, a diagnostic system is contemplated for use in assaying for the presence of EPR-1 proteins and/or polypeptides, whether or not said proteins/polypeptides are expressed on cell surfaces.

A preferred kit is typically provided as an enclosure (package) comprising a container for anti-EPR-1 antibodies capable of immunoreacting with EPR-1-related receptor molecules on cells in a cell sample. Typically, the kit also contains a labelled antibody probe that immunoreacts with the immunocomplex formed when an anti-EPR-1 antibody and an EPR-1 receptor, protein, or polypeptide immunoreact.

In another variation, a preferred kit is provided as an enclosure (package) that comprises a container including anti-EPR-1 antibodies capable of immunoreacting with EPR-1 receptor molecules, whether or not the receptor molecules are attached to, or free of, cellular material in the test sample. Typically, the kit also contains a labelled antibody probe that immunoreacts with the immunocomplex of the anti-EPR-1 antibody and the EPR-1 receptor.

The label may be any of those commonly available, including, without limitation, fluorescein, phycoerythrin, rhodamine, $^{125}$I and the like. Other exemplary labels include $^{111}$In, $^{99}$Tc, $^{67}$Ga, and $^{132}$ and nonradioactive labels such as biotin and enzyme-linked antibodies. Any label or indicating means that may be linked to or incorporated in an antibody molecule is contemplated as part of an antibody or monoclonal antibody composition of the present invention. A contemplated label may also be used separately, and those atoms or molecules may be used alone or in conjunction with additional reagents. Many useful labels of this nature are known in clinical diagnostic chemistry.

The linking of labels to polypeptides and proteins is also well known. For instance, antibody molecules produced by a hybridoma may be labelled by metabolic incorporation of radioisotope-containing amino acids provided as a component in the culture medium. See, for example, Galfre et al., *Meth. Enzymol.*, 73: 3–46 (1981). The techniques of protein conjugation or coupling through activated functional groups are particularly applicable. See, for example, Aurameas, et al., *Scand. J. Immunol.*, Vol. 8, Suppl. 7: 7–23 (1978), Rodwell et al., *Biotech.*, 3: 889–894 (1984), and U.S. Pat. No. 4,493,795 (the latter of which is incorporated by reference herein).

An instant diagnostic system may also include a specific binding agent. A "specific binding agent" is a chemical species capable of selectively binding a reagent species of the present invention but is not itself an antibody molecule of the present invention. Exemplary specific binding agents are antibody molecules, complement proteins or fragments thereof, protein A and the like that react with an antibody molecule of this invention when the antibody is present as part of the immunocomplex described above.

In preferred embodiments the specific binding agent is labelled. However, when the diagnostic system includes a specific binding agent that is not labelled, the agent is typically used as an amplifying means or reagent. In these embodiments, a labelled specific binding agent is capable of specifically binding the amplifying means when the amplifying means is bound to a complex containing one of the instant reagents.

For example, a diagnostic kit of the present invention may be used in an "ELISA" format to detect the presence or quantity of an EPR-1 protein or polypeptide in a body sample or body fluid sample such as serum, plasma or urine or a detergent lysate of cells, e.g., a 10 mM CHAPS lysate. "ELISA" refers to an enzyme-linked immunosorbent assay that employs an antibody or antigen bound to a solid phase and an enzyme-antigen or enzyme-antibody conjugate to detect and quantify the amount of antibody or antigen present in a sample. A description of the ELISA technique is found in Chapter 22 of the 4th Edition of Basic and *Clinical Immunology* by D. P. Sites et al., published by Lange Medical Publications of Los Altos, Calif. in 1982 and in U.S. Pat. Nos. 3,654,090; 3,850,752; and 4,016,043, which patent disclosures are incorporated herein by reference.

In preferred embodiments, the antibody or antigen reagent component may be affixed to a solid matrix to form a solid support that is separately packaged in the subject diagnostic systems. The reagent is typically affixed to the solid matrix by adsorption from an aqueous medium, although other modes of affixation well known to those skilled in the art may be used, such as specific binding methods. For example, an instant anti-EPR-1 antibody may be affixed to a surface and used to assay a solution containing EPR-1 molecules or cells expressing EPR-1 receptors. Alternatively, EPR-1, EPR-1 homologs, polypeptide fragments of EPR-1 or EPR-1 homologs, and whole or partially lysed cells expressing EPR-1 may be affixed to the surface and used to screen a solution for antibody compositions that immunoreact with the affixed species.

Useful solid matrix materials in this regard include the derivatized cross-linked dextran available under the trademark SEPHADEX from Pharmacia Fine Chemicals (Piscataway, N.J.), agarose in its derivatized and/or cross-linked form, polystyrene beads about 1 micron to about 5 millimeters in diameter (available from Abbott Laboratories of North Chicago, Ill.), polyvinyl chloride, polystyrene, cross-linked polyacrylamide, nitrocellulose- or nylon-based webs such as sheets, strips or paddles, tubes, plates, the wells of a microtiter plate such as those made from polystyrene or polyvinylchloride, and the like.

The reagent species, labelled specific binding agent or amplifying reagent of any diagnostic system described herein may be provided in solution, as a liquid dispersion or as a substantially dry powder, e.g., in lyophilized form. Where the indicating means is an enzyme, the enzyme's substrate may also be provided in a separate package of a kit or system. Usually, the reagents are packaged under an inert atmosphere. A solid support such as the before-described microtiter plate and one or more buffers may also be included as separately packaged elements in this diagnostic assay system.

The diagnostic system is usually contained in a conventional package. Such packages include glass and plastic (e.g., polyethylene, polypropylene and polycarbonate) bottles, vials, plastic and plastic-foil laminated envelopes and the like.

J. Therapeutic Methods

In view of the ability of anti-EPR-1 antibodies to bind EPR-1 and inhibit lymphoproliferation as demonstrated herein, anti-EPR-1 antibodies of this invention can be used therapeutically as EPR-1 antagonists to prevent the binding of factor Xa and similar molecules to EPR-1, and thus to disrupt or prevent the induction of lymphocyte proliferation. Inhibition of lymphocyte proliferation is desirable in a variety of indications, particularly when an individual is susceptible to a lymphoproliferative disorder such as CLL or HCL.

The method comprises contacting, in vivo or in vitro, a sample believed to contain one or more precursors to a lymphoproliferation complex (e.g., EPR-1) with a therapeutic composition of this invention containing an amount of anti-EPR-1 antibody sufficient to inhibit the binding of factor Xa, a factor Xa homolog, or another molecule with mitogenic/lymphoproliferative effects to EPR-1. In one embodiment, the contacting in vivo is accomplished by administering a therapeutically effective amount of a physiologically tolerable composition containing anti-EPR-1 antibodies of this invention to a patient, thereby inhibiting lymphocyte proliferation in the patient.

Thus, in one embodiment, the present invention describes a method for inhibiting lymphocyte proliferation in a mammal—preferably, and for example, a human—comprising administering to the human a therapeutically effective amount of an anti-EPR-1 antibody of this invention. In a preferred embodiment, the anti-EPR-1 antibody is monoclonal. In one embodiment, the anti-EPR-1 antibody is selected from the group consisting of 2E1, 2C11, 2D4, 3H7, 3G8, 3G10, and 6F1; in another embodiment, the EPR-1 antibody is 2E1.

A representative patient for practicing the present methods is any human at risk for a lymphoproliferative disease, such as Chronic Lymphocytic Leukemia (CLL) or Hairy Cell Leukemia (HCL).

A therapeutically effective amount of an anti-EPR-1 antibody is a predetermined amount calculated to achieve the desired effect, i.e., to bind EPR-1 present in the patient, and/or to with factor Xa for binding to EPR-1, whether expressed on a membrane or in soluble form, thus decreasing the likelihood of lymphocyte proliferation in the patient. (As noted previously, the within-disclosed first-generation anti-EPR-1 mAbs inhibit factor Xa binding, whereas the disclosed second-generation anti-EPR-1 mAbs do not.) In the case of in vivo therapies, an effective amount can be measured by improvements in one or more symptoms associated with CLL or HCL.

Thus, the dosage ranges for the administration of an anti-EPR-1 antibody of the invention are those large enough to produce the desired effect in which the symptoms of lymphocyte proliferation are ameliorated or the likelihood of proliferation is decreased. The dosage should not be so large as to cause adverse side effects, although none are presently known. Generally, the dosage will vary with the age, condition, and sex of the patient, as well as with the extent and severity of the disease in the patient, and can be determined by one of skill in the art. The dosage can be adjusted by the individual physician in the event of any complication.

A therapeutically effective amount of an anti-EPR-1 antibody of this invention is typically an amount such that when it is administered in a physiologically tolerable composition, it is sufficient to achieve a plasma or local concentration of from about 1 picomolar (pM) to 1,000 nanomolar (nM), preferably about 100 pM to about 50 nM, and most preferably about 1 to 30 nM.

The anti-EPR-1 antibodies of the invention can be administered parenterally by injection or by gradual infusion over time. The anti-EPR-1 antibodies of the invention can be administered intravenously, intraperitoneally, intramuscularly, parenterally, subcutaneously, intracavity, transdermally, or dermally, and they may also be delivered by peristalic means. In general, intravenous, intraperitoneal, or subcutaneous administration is preferred.

The therapeutic compositions containing an anti-EPR-1 antibody of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

K. Therapeutic Compositions

Therapeutic compositions of the present invention contain a physiologically tolerable carrier together with at least one species of anti-EPR-1 antibody of this invention as described herein, dispersed therein as an active ingredient. In a preferred embodiment, the therapeutic composition is not immunogenic when administered to a human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration upon a mammal or human without the production of undesirable physiological effects such as nausea, dizziness, gastric upset and the like.

The preparation of a pharmacological composition that contains active ingredients dispersed therein is well understood in the art. Typically such compositions are prepared as sterile compositions either as liquid solutions or suspensions, aqueous or non-aqueous, however, suspensions in liquid prior to use can also be prepared.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

A therapeutic composition contains a anti-EPR-1 antibody of the present invention, typically an amount of at least 0.1 weight percent of anti-EPR-1 antibody per weight of total therapeutic composition. A weight percent is a ratio by weight of anti-EPR-1 antibody to total composition. Thus, for example, 0.1 weight percent is 0.1 grams of anti-EPR-1 antibody per 100 grams of total composition.

A therapeutically effective amount of an anti-EPR-1 antibody-containing composition, or beneficial compound therein, is a predetermined amount calculated to achieve the desired effect, i.e., to effectively benefit the individual to whom the composition is administered, depending upon the benefit to be conferred. Thus, an effective amount can be measured by improvements in one or more symptoms associated with the condition of the lymphoproliferative disease occurring in the patient.

Thus, the dosage ranges for the administration of the anti-EPR-1 antibody of the invention are those large enough to produce the desired effect in which the condition to be treated is ameliorated. The dosage should not be so large as to cause adverse side effects. Generally, the dosage will vary with the age, condition, and sex of the patient, and the extent of the disease in the patient, and can be determined by one of skill in the art. The dosage can be adjusted by the individual physician in the event of any complication.

The compositions are administered in a manner compatible with the dosage formulation, and in a therapeutically effective amount. A therapeutic amount of an anti-EPR-1 antibody composition of this invention is an amount sufficient to produce the desired result, and can vary widely depending upon the disease condition and the potency of the therapeutic compound. The quantity to be administered depends on the subject to be treated, the capacity of the subject's system to utilize the active ingredient, and the degree of therapeutic effect desired. Precise amounts of active ingredient required to be administered depend on the judgment of the practitioner and are peculiar to each individual. However, suitable dosage ranges for systemic application are disclosed herein and depend on the conditions of administration. Suitable regimes for administration are also variable, but are typified by an initial administration followed by repeated doses at one or more hour intervals by a subsequent administration.

It is further contemplated that counter-receptor ligands for EPR-1, whether it is in soluble or cell-surface associated form, may be useful according to the within-disclosed diagnostic and therapeutic methods. For example, synthetic peptides or polypeptides which prevent the binding of factor Xa or molecules with substantially similar lymphoproliferative properties (i.e., other EPR-1 ligands) to the EPR-1 receptor are useful diagnostic and therapeutic compounds. Useful peptides or polypeptides which prevent the binding of factor xa to EPR-1 may include first-generation antibodies such as 13E5, 12H1, and the like, molecules that are substantially homologous to said first-generation antibodies, and molecules which mimic the activity of the first-generation anti-EPR-1 antibodies.

Alternatively, such peptides and polypeptides may mimic second-generation anti-EPR-1 antibodies such as 2E1 by occupying the 2E1 epitope, or via inducing other conformational changes to EPR-1 which interfere with the binding of factor Xa (or other EPR-1 ligands) to EPR-1 receptor molecules or otherwise disrupt the initiation of lymphocyte proliferation. Peptides and polypeptides useful as disclosed herein also include EPR-1 ligand molecules that are substantially homologous to factor Xa in terms of mimicking its binding to EPR-1, without stimulating lymphoproliferation.

In addition, it is contemplated that EPR-1 ligands directly or jointly participating in lymphocyte mitogenic signalling will be useful in diagnostic and therapeutic methods according to the present invention, particularly where stimulation of immune response is desired. EPR-1 ligands useful in this context include factor Xa and its homologs and various first-generation monoclonal antibodies, such as mabs 13E5 or 12H1. It is further contemplated that co-stimulatory molecules may also be useful in this regard. For example, as co-stimulatory signals such as those coordinated by the CD28:B7/B7-2 receptor-counterreceptor pair play a crucial role in maintaining antigen-specific mechanisms of the immune response in vivo, it is anticipated that these molecules and others with similar co-stimulatory effects will be useful in the modulation of lymphocyte proliferation as disclosed herein. Co-stimulatory molecules according to the present invention include mAbs 12H1 or 13E5 administered in conjunction with an anti-CD3 mAb such as OKT3, or with otherwise non-mitogenic concentrations of PMA. (See, e.g., Example 12 below.)

The terms "therapeutically effective" or "effective", as used herein, may be used interchangeably and refer to an amount of a therapeutic composition of the present invention—e.g., one containing an anti-EPR-1 monoclonal antibody. For example, a therapeutically effective amount of an anti-EPR-1 antibody-containing composition, or beneficial compound therein, is a predetermined amount calculated to achieve the desired effect, i.e., to effectively benefit the individual to whom the composition is administered, depending upon the benefit to be conferred. Thus, an effective amount can be measured by improvements in one or more symptoms associated with the condition of the lymphoproliferative disease occurring in the patient.

A therapeutically effective amount may also be an amount sufficient to measurably inhibit lymphocyte proliferation in a patient or subject, by at least about 10 percent, preferably by at least about 25 percent, more preferably by at least about 50 percent, and most preferably by at least about 75–100 percent. The mAbs and compounds of the present invention are typically administered as a pharmaceutical composition in the form of a solution or suspension. However, therapeutic compositions of the present invention may also be formulated for therapeutic administration as a tablet, pill, capsule, aerosol, sustained release formulation or powder.

The compositions are administered in a manner compatible with the dosage formulation, and in a therapeutically effective amount. The quantity to be administered depends on the subject to be treated, and capacity of the subject to utilize the active ingredient. Precise amounts of active ingredient required to be administered depend on the judgment of the practitioner and are peculiar to each individual. However, suitable dosage ranges are of the order of one to several milligrams of active ingredient per individual per day and depend on the route of administration. Suitable regimens for initial administration and booster shots are also variable, but are typified by an initial administration followed by repeated doses at one or more hour intervals, by a subsequent injection or other administration.

Alternatively, continuous intravenous infusion sufficient to maintain therapeutically effective concentrations in the blood are contemplated. Therapeutically effective blood concentrations of antibody molecules of the present invention are in the range of about 0.01 $\mu$M to about 100 $\mu$M, preferably about 0.1 $\mu$M to about 10 $\mu$M, and more preferably about 0.1 $\mu$M to about 1.0 $\mu$M.

EXAMPLES

The following examples are intended to illustrate, but not limit, the present invention.

Example 1

Isolation and Purification of EPR-1

A. Cells and Cell Culture

PMN (polymorphonuclear leucocytes) were isolated by dextran sedimentation from acid-citrate dextrose anticoagulated blood. PBMC (peripheral blood mononuclear cells) were separated after platelet-rich plasma was removed by low speed differential centrifugation over FICOLL-HYPAQUE (nonionic synthetic polymer of sucrose, and sodium diatrizoate). (Sigma Chemical Co., St. Louis, Mo.) (density=1.077 g/ml) at 400×g for 18 minutes at 22° C. PBMC were extensively washed in 5 mM EDTA-PBS, pH 7.2, and incubated twice in autologous serum containing 5 mM EDTA for 30 minutes at 37° C. to prevent platelet-monocyte rosetting. Monocytes were isolated from PBMC by adherence to plastic petri dishes precoated with autologous serum for 1 hour at 37° C. Cells were suspended at 1 to $1.5 \times 10^7$/ml in detectable endotoxin-free RPMI 1640 medium (Irvine Scientific, Santa Ana, Calif.) and 10% heat inactivated FCS (fetal calf serum; Gemini Bioproducts Inc., Calabasas, Calif.), 2 mM L-glutamine (Irvine), 25 mM HEPES (Calbiochem Boehring Diagnostic, La Jolla, Calif.), 100 $\mu$g/ml gentamicin (Geramycin, Schering Corp., Kenilworth, N.J.).

The monocytic cell line THP-1 (ATCC) was maintained in continuous culture in the above media further supplemented with 10 $\mu$M 2-ME (Eastman Kodak, Rochester, N.Y.). The transformed or transfected human leukemic-lymphoma T cell lines HuT 78, MOLT 4, CCRF-CEM, CCRF-HSB-2, and the human B lymphoma cell lines Raji and Daudi (ATCC) were maintained in culture per standard protocols, as recommended. Human leukemialymphoma T cell lines Jurkat, MLT, PEER, and MOLT 13 are all available from the American Type Culture Collection (ATCC, Bethesda, Md.).

For mixed lymphocyte response, $20 \times 10^6$ freshly isolated PBMC were cultivated in T-25 vented flasks (Costar Corp., Cambridge, Mass.) in the presence of $20 \times 10^6$ irradiated (10,000 rad) Raji or Daudi cells. Cultures were maintained in RPMI 1640, 10% FCS, 25 mM HEPES, 10 $\mu$M 2-ME (mixed lymphocyte culture (MLC) medium) in a 5% $CO_2$ humidified incubator for 7 days at 37° C. Responder cells were harvested, isolated by centrifugation on FICOLL-HYPAQUE at 400×g for 18 minutes at 22° C., washed in complete MLC medium, then cultured in 24-well plates (Costar Corp., Cambridge, Mass.) at $2 \times 10^5$/well in the presence of $2 \times 10^6$ irradiated Daudi or Raji cells.

PBMCs for the studies described herein were typically obtained from whole blood from normal human volunteers. After isolation on FICOLL-HYPAQUE gradients (Sigma Chemical Co., St. Louis, Mo.), PMBCs were washed twice in Dulbecco's PBS. PBMCs were suspended in a solution of 10% DMSO and 90% heat-inactivated FCS (Armour Pharmaceutical Co., Kankakee, Ill.) and could then be stored in liquid nitrogen until use. (Cell-surface antigen and proliferative responses of PBMCs after storage in liquid nitrogen are similar to properties of fresh lymphocytes.)

For long term culture of alloreactive cells stimulated by irradiated Daudi or Raji, responder T cells were transferred every 6 days according to the protocol described above and recultured in MLC medium containing 10% T cell growth factor (Cellular Product Inc., Buffalo, N.Y.). In some studies, suspensions of freshly isolated PBMC at $1 \times 10^6$/ml were treated with 1 µg/ml Con A (Calbiochem) or 1 µg/ml PHA (Phytohemagglutinin; Calbiochem) for 7 days in 5% $CO_2$ at 37° C. Aliquots of cells from these cultures were harvested after various time intervals, washed, and analyzed by FMF (flow microfluorometry).

B. Isolation and Purification of EPR-1 EPR-1 was isolated and affinity-purified from MOLT13 cell extracts using the first generation anti-EPR-1 mAb 12H1 (Altieri, et al., Id. (1990)) according to the following procedure. (Preparation and identification of mAb 12H1 is further described in Example 2.A. hereinafter.)

MOLT13 cells ($10^9$) were solubilized in a lysis buffer containing 0.05M NaCl, 0.05M Tris HCl, 0.5% CHAPS (Calbiochem, San Diego, Calif.), 1 mM $CaCl_2$, 1 mM PMSF, 1 mM benzamidine, 10 µM D-phenylalanyl-L-prolyl-L-arginine chloromethyl ketone (Boehringer Mannheim, Indianapolis, Ind.), 25 µg/ml leupeptin (Boehringer), and 25 µg/ml soybean trypsin inhibitor (Sigma Chemical Co., St. Louis, Mo.), pH 8/4 for 30 minutes at 4° C. The cell lysate was preadsorbed with iml PANSORBIN (Pharmacia Fine Chemicals, Piscataway, N.J.), cleared by ultracentrifugation at 40,000 rpm for 1 hour at 4° C., and incubated with anti-EPR-1 mAb 12H1 (1:100 dilution of ascites fluid) for 14 hours at 4° C., followed by 50 µg/ml aliquots SEPHAROSE (crosslinked agarose matrix) conjugated goat anti-mouse IgM (Calbiochem) for an additional 4 hours at 4° C. Eluted proteins were separated by electrophoresis on a single-well 7.5% SDS polyacrylamide slab gel under non-reducing conditions and visualized by Coomassie blue staining.

As shown in FIG. 2A, EPR-1 isolated, eluted and electrophoresed on a 7.5% SDS polyacrylamide gel under non-reducing conditions, according to the aforementioned procedure, had a relative molecular weight within the 62–74 kDa range, with an apparent $M_r$ of about 62 kDa. Sufficient amounts of EPR-1 were isolated via this procedure for use according to the within-disclosed methods and procedures.

Example 2

Generation of Monoclonal Antibodies (mAb)

Various classes of antibodies were generated according to the following methods. The within-disclosed antibodies are further described and characterized in subsequent Examples.

A. Preparation of First-Generation Anti-EPR-1 Monoclonal Antibodies

Many of the first-generation monoclonal antibodies (mAbs) used to identify and isolate EPR-1 were originally generated using purified factor V as the immunogen. Experimental procedures for purification and characterization of human factor V were conducted as described in Altieri, et al., J. Biol. Chem. 264: 2969 (1989).

Briefly, BALB/c mice were immunized intraperitoneally with 50 µg of factor V in CFA (complete Freund's adjuvant; Calbiochem, San Diego, Calif.) and hybridomas were generated as described. Screening strategy for antibody selection comprised analysis by FMF of the reactivity of hybridoma culture fluids with THP-1 cells. Six hybridomas reacting with >98% of THP-1 cells were selected for antibody production in solid phase RIA and immunoblotting using immobilized factor V, and were finally established by two to four times sequential subclonings by limiting dilution.

A rabbit polyclonal antiserum raised by multiple immunizations with purified factor V was also screened by FMF and characterized according to the strategy described above. In addition, a second panel of mAb elicited by immunization with factor V, which were reactive with factor V by Western blot but were nonreactive with THP-1 cells by FMF, was selected and established.

Purified Ig fractions of mAb 7G12 (IgG2a), 9D4 (IgGl), and 12H1 (IgM) (ATCC Accession No. HB 10637) were prepared by chromatography on AFFIGEL (complied agarose gel) MAPS II or hydroxylapatite columns (Bio-Rad, Richmond, Calif.). Purified Ig fractions of anti-V rabbit polyclonal antiserum B78.9 were prepared by ammonium sulfate fractionation and chromatography on DEAE SEPHADEX (hydroxypropylated crosslinked dextran matrix). Immunopurified B78.9 antibodies were isolated from purified factor V immobilized on AFFIGEL 15 (BioRad, Richmond, Calif.) according to the manufacturer's directions.

B. Preparation of Second-Generation Anti-EPR-1 Monoclonal Antibodies

In order to isolate cDNA clones encoding EPR-1, a novel mAb panel was raised against the EPR-1$^+$ cell line MOLT13. Murine hybridomas were generated against MOLT13 lymphocytes by sequential immunization according to published protocols (Altieri, et al., J. Biol. Chem. 264: 2969–2972 (1989)). Briefly, murine hybridomas were generated against intact EPR-1$^+$ MOLT13 cells by sequential intraperitoneal immunizations with $10^6$ intact viable cells, without adjuvants, according to published protocols (Altieri, et al.,J. Immunol. 145: 246 (1990)). Hybridoma culture fluids were initially screened for their reactivity with MOLT13 cells by flow cytometry and subsequently screened in Western blots for their reactivity with isolated EPR-1, affinity-purified from MOLT13 cell extracts using the first generation anti-EPR-1 mAb 12H1 (Altieri, et al., Id. (1990)), according to the procedures described in Example 1.B. above.

Immuno-purified EPR-1 was electroblotted to IMMO-BILON membranes (Millipore Corp., Bedford, Mass.) and incubated with the hybridomas that reacted with MOLT13 cells by flow cytometry in a slot blotter apparatus. Binding of the primary mAb was revealed by addition of 5 µg/ml 125I-F(ab')$_2$ goat anti-mouse IgG (Tago Inc., Burlingame, Calif.) and autoradiography.

Seven mAbs bound strongly to MOLT13 cells, recognized immunopurified EPR-1 in Western blots, and immunoprecipitated EPR-1 from $^{125}$I-surface labeled PBMC extracts. The seven mAbs are identified herein as 2C11, 2D4, 2E1, 3H7, 3G8, 3G10, and 6F1. All seven have been characterized as belonging to the IgG$_{2a}$ isotype.

These second-generation mAbs, unlike first-generation mabs (e.g., 9D4, 12H1), do not inhibit factor Xa binding to EPR-1. The first-generation monoclonal antibodies are capable of inhibiting factor Xa binding to EPR-1. Moreover, deletion mapping experiments verified that the two classes of antibodies (first- and second-generation) do not cross-compete.

One of these mAbs (2E1) was selected for further investigations and was used in functional expression cloning of the EPR-1 cDNA as described herein (see Example 4 hereinbelow). Purified IgG fractions from the hybridomas are preferably purified by affinity chromatography using the MAPS II system (Monoclonal Antibody Purification System, BioRad, Richmond, Va.).

As shown in FIG. 2A, serum-free suspensions of EPR-1+ MOLT13 lymphocytes ($4 \times 10^8$) were lysed in a lysis buffer containing 0.05 M Tris HCl, 0.15 M NaCl, 0.3% CHAPS, 1 mM $CaCl_2$ plus protease inhibitors, pH 7.4. Cell extracts were cleared of nuclei and other insoluble material by centrifugation at 6,000×g for 30 min at 4° C., and further incubated with 1:100 ascites dilution anti-EPR-1 mAb 12H1 (IgM) for 14 hours at 4° C. in constant agitation. The immune complexes were precipitated by addition of 50 μg/ml aliquots SEPHAROSE-conjugated goat anti-mouse IgM (Calbiochem, La Jolla, Calif.) for 4 hours at 4° C., washed six times in lysis buffer, eluted, and electrophoresed on a 7.5% SDS polyacrylamide gel electrophoresis under non-reducing conditions. Eluted proteins were stained with Coomassie blue R250.

As illustrated in FIG. 2B, reactivity of anti-MOLT13 by hybridomas with isolated EPR-1 is shown. Murine hybridomas were generated against MOLT13 lymphocytes by sequential immunization according to published protocols (Altieri, et al., *J. Biol. Chem.* 264: 2969–2972 (1989); also see Example 1 above). Immunopurified EPR-1 shown in FIG. 2A was electroblotted onto IMMOBILON membranes (Millipore), blocked in BLOTTO buffer overnight at 4° C., and incubated with the various anti-MOLT13 hybridomas in a slot blotter apparatus for 2 hours at 22° C. After washes, binding of the primary mAb was revealed by the addition of 5 μg/ml aliquots of $^{125}$I-goat anti-mouse IgG for 2 hours at 22° C., followed by autoradiography of the dried transfer. Each lane corresponds to the reactivity of an individual anti-MOLT13 hybridoma with isolated EPR-1. As shown, seven hybridomas produced immunoglobulins reactive with EPR-1, including hybridomas 2E1, 2D4, 2C11, 3H7, 3G8, 3G10, and 6F1.

FIG. 2C illustrates immunoprecipitation of EPR-1 from $^{125}$I-surface labeled lymphocyte extracts. One of the anti-MOLT13 hybridomas (mAb 2E1) reacting with isolated EPR-1 in 2B was used in immunoprecipitation experiments of surface iodinated lymphocyte extracts as described previously (Altieri, et al., Id. (1989); Altieri, et al., Id. (1990)). Lane 1, anti-EPR-1 mAb 2E1; lane 2, control mAb 6B4. Relative molecular weight markers (MW) are indicated on the left side of each of FIGS. 2A, 2B, and 2C.

Results of the studies illustrated in FIGS. 2A–C indicated that, as opposed to the broad $M_r$ ~74 kDa band previously resolved from THP-1 cells (Altieri, et al., Id. (1989), EPR-1 isolated from PBMC extracts appeared as a sharper band of $M_r$ ~62 kDa. In agreement with prior observations (Altieri, et al., Id. (1989)), mAb 2E1 immunoprecipitated EPR-1 as a broad $M_r$ ~74 kDa band from $^{125}$I-surface labeled THP-1 cells, indistinguishable for molecular weight and structural organization from the band immunoprecipitated by the first generation anti-EPR-1 mAbs 12H1 or 13E5 under the same experimental conditions (compare FIGS. 2A–C). The data confirmed the recognition of mAb 2E1 for EPR-1 and suggested that variations in EPR-1 $M_r$ between PBMC and THP-1 cells might reflect cell-specific differences in receptor glycosylation (see below). At variance with the first anti-EPR-1 mAb panel (Altieri, et al., Id. (1989)), mAb 2E1 only slightly inhibited prothrombin activation on THP-1 cells (not shown), thus implicating a different epitope recognition.

1. Affinity Chromatography

Briefly, 27 mg of a purified IgG fraction of an anti-EPR-1 mAb (e.g., 2.08 mg/ml of mAb 2E1) was coupled to AFFIGEL (BioRad) in 0.1M MES (Sigma Chemical Co., St. Louis, Mo.), 0.5% TRITON X-100 (t-octylphenoxypolythoxyethanol) (Sigma), and 0.5% NP-40 (Sigma), pH 6.5, for 14 hours at 4° C. in constant agitation. The Affi-Gel coupled mAb was centrifuged at 1,000 rpm for 10 minutes at 4° C., and sequentially washed with 1M NaCl, 0.5% TRITON X-100 /NP-40, 0.01% $NaN_3$; then with 0.1M glycine, 0.5% TRITON X-100 /NP-40, 0.01% $NaN_3$, pH 4.5; and finally in 0.1M glycine, 0.5% TRITON X-100 /NP-40, 0.01% $NaN_3$, pH 2.7. MOLT13 cells ($1 \times 10^9$) were lysed in a lysis buffer containing 0.5% M NaCl, 0.05% M Tris HCl, 0.5% CHAPS (Calbiochem Corp., La Jolla, Calif.), 1 mM $CaCl_2$, 1 mM phenylmethylsulfonylfluoride (PMSF), 1 mM benzamidine, 10 μM D-phenylalanyl-L-prolyl-L-arginine chloromethyl ketone (PPACK, Boehringer Mannheim, La Jolla, Calif.), 10 μg/ml leupeptin (Boehringer Mannheim), 10 μg/ml soybean trypsin inhibitor (Sigma, St. Louis, Mo.), pH 8.4, for 30 minutes at 4° C. in constant agitation.

The cell lysate was incubated with 1 ml PANSORBIN (Pharmacia Chemical Co., Piscataway, N.J.) for 30 minutes at 4° C. and cleared of nuclei and other detergent-insoluble material by ultracentrifugation at 40,000 rpm for 1 hour at 4° C. AFFIGEL coupled EPR-1 mAb (2E1) was incubated with MOLT13 cell extracts for 14 hours at 4° C. with constant agitation, and washed in the same lysis buffer described above. After washes in Tris-buffered saline (TBS), pH 7.0 (fractions 1–15, 0.5 ml each), mAb 2E1-bound material was further washed in 1M NaCl (fractions 16–20), followed by 0.1M glycine, pH 4.5 (fractions 21–30), 0.1M NaCl (fractions 31–34), and finally eluted in 0.1M glycine, pH 2.7 (fractions 35–55). All the buffers used for washes and elutions in affinity chromatography experiments contained 0.5% CHAPS.

Fractions were immediately neutralized with 300 μl 1M Tris HCl, pH 9.6, lyophilized overnight, washed in 100% acetone, and resuspended in TBS/0.5% CHAPS, pH 7.2. Aliquots of the eluted material were electrophoresed on a 10% SDS gel under reducing or nonreducing conditions and further processed for immunoblotting with mAb 2E1, as described below. Amino-terminal sequencing of the mAb affinity purified material was carried out on an Applied Biosystems gas phase sequenator with on-line HPLC.

2. Immunoblotting and Immunoprecipitation

Aliquots of the mAb 2E1-affinity purified material or of detergent-solubilized extracts from various cell lines were separated by electrophoresis on a 7.5% or 10% SDS gel, and electroblotted to Immobilon membranes (Millipore) at 450 mAmps for 2 hours at 22° C. The transfer membranes were blocked in TBS plus 5% nonfat dried milk, pH 7.4, for 14 hours at 4° C. and further incubated with 20 μg/ml aliquots mAb 2E1 or other primary mAb for 2 hours at 22° C. Alternatively, undiluted culture supernatant of mAb 2E1 or of the other second generation anti-EPR-1 mAbs were used.

After three washes in TBS, pH 7.4, the transfer membranes were further incubated with 5 μg/ml aliquots of $^{125}$I-labeled goat anti-mouse F(ab')$_2$ fragments (Tago Inc., Burlingame, Calif.) for an additional 2 hours at 22° C. After washes, radioactive bands were visualized by autoradiography of the dried transfer using a KODAK X-OMART radiographic film AR-X-ray film and intensifying screens (Cronex, E.I. duPont de Nemours, Wilmington, Del.).

In immunoprecipitation experiments, aliquots of HEL or MOLT13 cells ($5 \times 10^7$) were surface labeled with 2.5 mCi $^{125}$I-Na (Amersham Corp., Arlington Heights, Ill.) by the IODO-GEN method, washed extensively in PBS, pH 7.4, lysed in 0.5% CHAPS lysis buffer and cleared by ultracentrifugation at 40,000×g for 1 hour at 4° C. Aliquots of the $^{125}$I-labeled cell lysate were processed for immunoprecipitation with control mAb 6B4 or anti-EPR-1 mAb 2E1 as described previously in detail (Altieri, et al., *J. Immunol.* 145: 246 (1990); Altieri, et al., *J. Biol. Chem.* 264: 2969 (1989)). For metabolic labeling, suspensions of MOLT13 cells (4×10$^7$) were cultivated in DMEM methionine-free media (Whittaker) in the presence of 1 mCi $^{35}$S-methionine (Amersham) for 2 hours at 37° C. in an 8% $CO_2$ incubator. Cells were extensively washed in complete RPMI 1640 medium, lysed in 0.5% CHAPS lysis buffer, cleared by ultracentrifugation, and processed for immunoprecipitation as described in Altieri, et al., Id., (1989) and Altieri, et al., Id., (1990).

Immunopurified EPR-1 was electroblotted onto IMMOBILON membranes (Millipore), blocked in BLOTTO buffer overnight at 4° C., and incubated with the various anti-MOLT13 hybridomas in a slot blotter apparatus for 2 hours at 22° C. After washes, binding of the primary mAb was revealed by the addition of 5 μg/ml aliquots of $^{125}$I-goat anti-mouse IgG for 2 hours at 22° C., followed by autoradiography of the dried transfer. Each lane corresponded to the reactivity of an individual anti-MOLT13 hybridoma with isolated EPR-1 (see FIGS. 2A–2C).

Seven mAbs strongly bound to MOLT13 cells by flow cytometry, reacted with immunopurified EPR-1 in Western blots (FIG. 2A and 2B), and immunoprecipitated EPR-1 from $^{125}$I-surface-labelled lymphocyte extracts (FIG. 2C). These seven mAbs include 2E1, 2D4, 2C11, 3H7, 3G8, 3G10, and 6F1.

Immunoscreening of a human λgt11 cDNA library with one of these mAbs (2E1) yielded a single positive clone (λ104), that hybridized in Northern blots with a message of 1.9 Kb in RNA extracted from various hemopoietic EPR-1$^+$ cell lines.

One of the anti-MOLT13 hybridomas (mAb 2E1) which produced antibodies reactive with isolated EPR-1 was used in immunoprecipitation experiments of surface iodinated lymphocyte extracts according to previously-described protocols (Altieri, et al., Id. (1989); Altieri, et al., Id. (1990)). Lane 1, anti-EPR-1 mAb 2E1; lane 2, control mAb 6B4. Relative molecular weight markers (MW) are indicated on the left side of each of FIGS. 2A, 2B, and 2C.

C. mAbs to EPR-1 Fusion Protein

An 800 bp PstI subclone encoding two-thirds of the EPR-1 extracellular domain, the putative transmembrane domain, and the cytoplasmic tail was inserted in frame in the prokaryotic expression vector pRSET A (Invitrogen, San Diego, Calif.), expressed in *E. coli* as a bacterial fusion protein ($M_r$ ~31 kDa), and purified from bacterial lysate using a metal ion binding column, according to the manufacturer's specifications.

The EPR-1 fusion protein was used to generate a sequence-specific antibody in rabbits by sequential immunization in complete/incomplete Freund's adjuvant. The anti-fusion protein antibody immunoblots EPR-1 ($M_r$ ~62 kDa) from EPR-1 CHO transfectants, but not from WT-CHO, which is structurally indistinguishable from the molecule immunoblotted by anti-EPR-1 mAb 9D4 from normal lymphocyte extracts (data not shown).

D. Non-Anti-EPR-1 mAbs

Anti-CD16 mAbs used according to within-described methods included LEU 11B (Becton Dickinson, Mountain View, Calif.), B73.1 and 3G8. (The latter were the kind gift of Dr. G. Trinchieri, the Wistar Institute, Philadelphia Pa.) Anti-CD56 mAb NKH-1 (Leu 19) was purchased from Coulter Immunology, Hialeah, Fla. Anti-CD11b and anti-CD18 mAbs were OKM1 and 60.3, respectively. mAbs to CD57 (HNK-1), CD3 (OKT3), CD4 (OKT4), CD8 (OKT8), CD2 (OKT11), HLA class I (W6/32) were acquired from the ATCC (Rockville, Md.). Anti-α/β T cell receptor (TCR) mAb WT31 was purchased from Becton Dickinson (Mountain View, Calif.), and anti-γ/δTCR mAb δ1 was kindly provided by Dr. M. B. Brenner (Harvard Medical School, Boston, Mass.).

Example 3

Binding Reactions

The interaction of various mAb with different cell types was evaluated by flow microfluorometry (FMF). Briefly, 1×10$^6$ cells were incubated in V-bottomed microtiter plates (Costar Corp. Cambridge, Mass.) with saturating concentrations of each mAb for 30 minutes at 4° C. After washes in MLC media, 1/20 dilution aliquots of fluorescein-conjugated goat F(ab')$_2$ anti-mouse IgG+IgM (Tago Inc., Burlingame, Calif.) were added for an additional 30 minutes at 4° C. Cells were washed and immediately analyzed on a Becton Dickinson IV/40 FACS (Becton Dickinson, Mountain View, Calif.). Simultaneous two-color FMF analyses were performed as described previously (Altieri, et al., *J. Biol. Chem.* 264: 2969 (1989)) using mAb 7G12 or 9D4 previously conjugated with biotin (N-hydroxysuccinimido-biotin, Sigma, St. Louis, Mo.) and revealed by 1/20 dilutions of phycoerythrin-conjugated streptavidin reagent (Tago Inc., Burlingame, Calif.).

To confirm the accuracy of the two-color FMF analysis performed on the various cell populations, two additional sets of studies were also carried out. First, to avoid possible cross-reaction of the second FITC-conjugated anti-mouse reagent with the biotinylated mAb, these studies were repeated by using biotin-conjugated aliquots of the rabbit polyclonal antibody B78.9 in association with the various anti-T cell or anti-NK (natural killer) cell-related markers mAb.

In a further series of studies, directly FITC-conjugated mAb 7G12 or 9D4 (Chromaprobe, Inc., Redwood City, Calif.) were also used in combination with biotin-conjugated mAb) OKT3, OKT4, OKT8. For cell sorting studies, HuT 78 cells (1.5×10$^7$/ml) were incubated with the anti-V polyclonal antiserum B78.9 followed by fluorescein-conjugated goat anti-rabbit IgG (Tago Inc., Burlingame, Calif.). B78.9$^+$ HuT 78 cells (HuT 78*, 34% of the unfractionated population) were isolated on a Becton Dickinson Facstar under negative pressure with a sweep rate of 2000 cells/sec., washed in complete MLC medium, and cloned by limiting dilution in 96-well round-bottomed plates (Costar Corp., Cambridge, Mass.) at 0.3, 1, and 3 cells/well in HuT 78 conditioned medium supplemented with 20% FCS. After 3 weeks, proliferating cells of single cell clonal origin on the basis of Poisson distribution were subcloned, established, and further phenotypically characterized by FMF.

The procedures for the isolation, characterization, and $^{125}$I-labelling of factor Xa were as described previously by Altieri, et al., *J. Biol. Chem.* 264: 2969 (1989). The interaction of $^{125}$I-Xa with HuT 78* cells was analyzed by incubating increasing concentrations of $^{125}$I-Xa (0.45 to 36 nM) with cell suspension at 1.5 to 2×10$^7$/ml in the presence of 2.5 mM $CaCl_2$ for 20 minutes at room temperature. At the end of the incubation, the reaction was terminated by centrifugation of aliquots of the cell suspension at 12,000×g for 2 minutes through a mixture of silicone oil to separate free from cell-associated radioactivity. Non-specific binding was quantified in the presence of 50-fold molar excess of unlabelled factor Xa added at the start of the incubation reaction, and was subtracted from the total to yield net specific binding. In some studies, aliquots of HuT 78* cells were preincubated with 50 µg/ml of mAb 9D4 for 30 minutes at room temperature before the addition of serial concentrations of $^{125}$I-Xa.

When suspensions of HuT 78* were equilibrated with increasing concentrations of $^{125}$I-Xa in the presence of 2.5 mM $CaCl_2$, these cells bound the offered ligand in a specific and concentration-dependent reaction, approaching steady saturation at 30–36 nM of added $^{125}$I-Xa (data not shown). Quantitatively similar to the results previously obtained with THP-1 cells (Altieri, et al., *J. Biol. Chem.* 264: 2969 (1989)), this reaction was regulated by an apparent $K_d$ in the order of 10 to 20 nM, and was saturated when 194,000±26,000 molecules of $^{125}$I-Xa were specifically associated with the surface of HuT 78* cells (not shown). Finally, preincubation of HuT 78* cells with saturating amounts of mAb 9D4 produced complete abrogation of $^{125}$I-Xa specific binding to these cells (not shown).

Example 4

Isolation of the EPR-1 Molecule

The isolation to homogeneity of the EPR-1 molecule required the identification and/or establishment of cell types that constitutively express high levels of this surface antigen. These studies were conducted primarily on peripheral blood polymorphonuclear leukocytes (PMN) and on a specifically selected T cell clonal derivative from the parental T cell line MOLT13 #3 (Altieri, et al., *J. Immunol.* 145: 246–253 (1990)).

The results of the following studies are discussed herein, in Section B of the Detailed Description, and in Example 2.B. hereinabove.

A. Cells and Cell Cultures

The T leukemia cell line MOLT13, monocytic THP-1, B lymphoma Daudi, and T leukemia MLT (all available from the ATCC, Rockville, Md.) were grown in RPMI 1640 medium (M. S. Whittaker, Walkersville, Md.) containing 10% fetal calf serum (FCS, Whittaker), 1 mM L-glutamine (Whittaker), and $10^{-5}$M β-mercaptoethanol (Eastman Kodak, Rochester, N.Y.). (Although any EPR-1$^+$ MOLT13 cell line is presumed to be useful as disclosed herein, a preferred cell line identified as MOLT13 #3 has been deposited and has been given ATCC Accession No. CRL 10638.) The subline MOLT13 #3 was established by two sequential cycles of fluorescence sorting of the parental line MOLT 13 using the anti-EPR-1 mAb 12H1. Only MOLT 13 cells expressing the highest levels of reactivity with mAb 12H1 by fluorescence analysis were isolated, cloned by limiting dilutions at 1 or 3 cells/well, grown to confluence, and finally re-screened again by flow cytometry for reactivity with mAb 12H1 as well as with a panel of mAbs directed against various T cell-related markers. The subline MOLT13 #3, established as described above, expressed 7–10 fold higher levels of EPR-1 as compared with the parental line.

B. Monoclonal Antibodies

The establishment and characterization of anti-EPR-1 mAbs 12H1 (IgM), 13E5 (IgG 2a) and 9D4 (IgG1) has been reported previously (Altieri, et al., Id. (1989) and (1990)). Anti-tissue factor mAb 6B4 was used as a control antibody in various experiments described herein; mAb 6B4 is described in U.S. Pat. No. 5,110,730 to Edgington, et al., the relevant disclosures of which are incorporated by reference herein. (Monoclonal antibody 6B4 was deposited pursuant to Budapest Treaty requirements with the ATCC on Mar. 27, 1987, in conjunction with the application maturing into U.S. Pat. No. 5,110,730, and was assigned accession number HB9381.)

To generate a novel panel of anti-EPR-1 hybridomas, mice were sequentially immunized with aliquots of $10^6$ MOLT13 lymphocytes/injection without adjuvant (viability>97%), according to published protocols (Altieri, et al., Id. (1989)), and as described in Example 2 hereinabove.

C. Immunoprecipitation $^{125}$I-surface labeled detergent solubilized extracts of peripheral blood mononuclear cells (PBMC) or monocytic THP-1 cells were immunoprecipitated with the first generation anti-EPR-1 mAb 13E5, or with the new mAb 2E1 described herein, using methods described previously (Altieri, et al., Id. (1989) and (1990)). Immunoprecipitates were washed six times in lysis buffer, separated by electrophoresis on a 10% SDS-polyacrylamide gel under non-reducing conditions, and radioactive bands were visualized by autoradiography of the dried gel. Results are illustrated in FIG. 2 and are further discussed in Example 2.B. above.

D. Molecular Cloning of EPR-1 cDNA

A human, oligo dT-primed λgt11 cDNA library constructed from the T cell line MLT was used in immunoscreening experiments with mAb 2E1. (λgt11 libraries are commercially available from suppliers such as Clontech (Palo Alto, Calif.); Stratagene (La Jolla, Calif.), and Invitrogen (San Diego, Calif.).) One million plaques induced with 10 mM isopropyl-β-D-thiogalactopyranoside (IPTG, Calbiochem, La Jolla, Calif.) were transferred to duplicate nitrocellulose filters (Millipore Corp., Bedford, Mass.), washed in TBS containing 0.02% Tween 20 (Sigma Chemical Co., St. Louis, Mo.), pH 7.4, blocked in TBS plus 5% nonfat dried milk, pH 7.4, and incubated with 50 µg/ml anti-EPR-1 mAb 2E1 for 2 hours at 22° C. After washes, filters were incubated with 5 µg/ml $^{125}$I-F(ab')$_2$ goat anti-mouse IgG, washed, and exposed for autoradiography. A positive clone reactive with mAb 2E1, identified as clone λ104, was isolated, plaque-purified by three sequential rounds of immunoscreening, subcloned in pBluescript (pBSKS$^-$, Stratagene, La Jolla, Calif.), and characterized by restriction and DNA sequence analysis.

$^{32}$P-random-primed (Boehringer-Mannheim)-labelled λ104 was used to screen the following oligo dT-primed human cDNA libraries: λgt11 MLT, λgt11 human umbilical vein endothelial cell, pcDNAII Daudi, and λgt10 erythroleukemia. Hybridizations were carried out in 5×SSC, 5×Denhardt's solution, 1% SDS, 0.1% sodium pyrophosphate, 100 µg/ml denatured salmon sperm DNA (Promega, Madison, Wis.) for 12 hours at 65° C. Filters were washed twice in 2×SSC, 1% SDS for 30 minutes at 65° C., and once in 0.2×SSC at 22° C., before exposure for autoradiography.

Twenty-eight independent clones were isolated from the four different libraries, plaque-purified, subcloned in pBSKS$^-$ (except for pcDNAII clones) and characterized by restriction analysis. DNA sequencing of all the isolated clones was carried out on both strands of Exonuclease III (Promega, Madison, Wis.)—generated nested deletions using Sequenase (USB, Cleveland, Ohio). For transfection experiments, a full-length EPR-1 cDNA clone (HEL λ407) was inserted in the mammalian cell expression vector pRC/CMV (Invitrogen Corp., San Diego, Calif.) at the vector's EcoRI site, oriented, and transfected (10–15 µg plasmid DNA) in subconfluent cultures of Chinese Hamster Ovary (CHO) cells by electroporation. Forty-eight hours after transfection, CHO cells were diluted 15-fold and cultivated in DMEM (M. S. Whittaker, Walkersville, Md.) selection media containing 10% FCS, 1 mM L-glutamine, non-essential amino acids (Irvine Scientific, Calabasas, Calif.) and 0.7 mg/ml Geneticin (GIBCO, Grand Island, N.Y.). Wild type (WT) CHO cells or EPR-1 CHO transfectants were analyzed for their reactivity with anti-EPR-1 mAbs 12H1 or 2E1 by FMF (Altieri, et al., *J. Biol. Chem.* 264: 2969–2972 (1989); Altieri, et al., *J. Immunol.* 145: 246–253 (1990)), or in $^{125}$I-factor Xa binding studies and prothrombin activation (see below). The results show that this cell line expressed EPR-1 protein, at levels five times greater than in MOLT13 EPR-1$^+$ cells. (See Section B, Detailed Description.)

E. Northern Blots

Total RNA was extracted from EPR-1$^+$ cell lines THP-1 (monocytic), Daudi (B lymphoma), or MLT (T lymphoma) by the guanidinium-isothiocyanate method. mRNA was isolated by chromatography on oligo-dT cellulose columns (Invitrogen Corp., San Diego, Calif.).

RNA samples (10 µg total RNA, 0.5 µg mRNA) were electrophoresed on agarose formaldehyde gels, transferred to GENESCREEN (charged nylon hybridization transfer membranes) membranes (dupont de Nemours, Wilmington, Del.), UV cross-linked (Stratagene, La Jolla, Calif.), and hybridized with EPR-1 cDNA clones as described above, except that 5% SDS was used during the washes of the membranes.

F. Binding Reactions and Prothrombin Activation

The experimental procedures for the isolation, characterization and $^{125}$I-labeling of factor Xa have been described previously (Altieri, et al., Id. (1989)). Serum-free suspensions of WT CHO cells or EPR-1 CHO transfectants at $5 \times 10^6$/ml were incubated with increasing concentrations of $^{125}$I-factor Xa (0.45–36 nM) for 15 minutes at 22° C. in the presence of 2.5 mM CaCl$_2$, before separation of free from cell-associated radioactivity by centrifugation through mixture of silicone oil (Dow Corning, New Bedford, Mass.) at 15,000×g for 5 minutes at 22° C. Non-specific binding was assessed in the presence of a 50-fold molar excess of unlabeled factor Xa and was subtracted from the total to calculate net specific binding. In separate experiments, WT CHO cells or EPR-1 CHO transfectants at $1 \times 10^5$/ml were mixed with various factor Xa concentrations (9–36 nM), 10 µg/ml prothrombin, and 2.5 mM CaCl$_2$ for 5 minutes at 22° C. before quantitation of prothrombin activation by a sensitive clotting assay, as described previously (Altieri, et al., Id. (1989)). In mAb inhibition experiments, WT CHO or EPR-1 CHO transfectants were preincubated with 25 µg/ml control mAb 6B4 or anti-EPR-1 mAb 9D4 (Altieri, et al., Id. (1990)) for 15 minutes at 22° C. before measurement of $^{125}$I-factor Xa specific binding or prothrombin activation, as described above.

Example 5

EPR-1 Expression Correlates With Response to CLL Therapy

The reactivity of anti-EPR-1 mAbs with peripheral blood cells isolated from patients with hematopoietic malignancies was explored with flow microfluorimetry (FMF). It was found that in 27 out of 30 CLL patients (90%), the number of EPR-1$^+$ cells was increased 5–6 fold thereby including most of the circulating population, as compared with normal controls (EPR-1$^+$ cells in normal donors: 16.5±3.2%, n-12 versus EPR-1$^+$ cells in CLL: 89.1±2.5%, n-28). The number of EPR-1 molecules expressed on CLL cells also showed a mean increase of 2.5 fold as compared with normal controls (mean fluorescence of EPR-1$^+$ normal cells: 85.6±16.1 versus EPR-1$^+$ CLL: 215.6±50.3). Roughly 98% of PMC cell were positive to this marker. Two-color flow cytometry studies confirmed that in CLL patients both CD5 and EPR-1 were simultaneously co-expressed in the same cell population. Finally, sequential analysis of a group of CLL patients carried out over a 4-month period (starting at day 0) showed that positive biologic response to the therapy was frequently associated with drastic reduction (67–90% reduction) in the number of EPR-1$^+$ cells detected. Representative patient data are presented in Table 1, below, and illustrate this trend.

EPR-1 therefore represents a novel cellular marker in CLL and its surface expression inversely correlates with the patient's biologic response to the therapy. The data further emphasize the possible participation of protease-mediated mechanisms in the development and/or establishment of selected hematopoietic malignancies.

TABLE 1

EPR-1 Expression in Leukemia Cells[1]

| Patient # | Day | % 12H1 | % B78.9 |
|---|---|---|---|
| 1 | 0 | 91.5 | 74.4 |
|  | 35 | 95.3 | 11.4 |
|  | 70 | 9.2 | 49.6 |
| 2 | 0 | 46.8 | 52.8 |
|  | 41 | 98.7 | 98.6 |
|  | 75 | 5.2 | 32.8 |
| 3 | 0 | 98.3 | 92.6 |
|  | 36 | 66.7 | 83.7 |
| 4 | 0 | 25.4 | 32 |
|  | 28 | 46.3 | 51.8 |
|  | 56 | 2.9 | 1.4 |
|  | 84 | 63 | 41.2 |
| 5 | 0 | 99.7 | 98.9 |
|  | 55 | 21 | 43.8 |
| 6 | 0 | 94 | 31.2 |
|  | 35 | 9.6 | 88.9 |
| 7 | 0 | 97 | 96.8 |
|  | 34 | 75.8 | 87 |
| 8 | 0 | 96.7 | 88.4 |
|  | 34 | 92.6 | 77.2 |
|  | 69 | 82.2 | 12.2 |

[1]12H1 and B78.9 are monoclonal and polyclonal antibodies, respectively, as described above. The data presented are percentages of cells examined which expressed suprathreshold amounts of EPR-1.

Example 6

Participation of EPR-1 in Proliferative Events and its Role as a Marker

A. Overexpression of EPR-1 in CLL

Deregulated expression of growth factor receptors is known to contribute to certain neoplasias (Ulrich, et al., *Nature* 309: 418–425 (1984); Sherr, et al., *Cell* 41: 665–676 (1985); Downward, et al., *Nature* 307: 521–527 (1984)), but whether it also participates in human leukemogenesis remains uncertain. (See, e.g., Sawyers, et al., *Cell* 64: 337–350 (1991); Heard, et al., *Cell* 51: 663–673 (1987); Meeker, et al., *Blood* 76: 285–289 (1990).) It is now disclosed herein that 90% of patients with Chronic Lymphocytic Leukemia (CLL, n=30) express a cell surface antigen denominated Effector cell Protease Receptor-1 (EPR-1) (Altieri, et al., *J. Biol. Chem.* 264: 2969–2972 (1989); Altieri, et al., *J. Immunol.* 145: 246–253 (1990); Worfolk, et al., *Blood* 80: 1989–1997 (1992)), at a 5- to 50-fold higher density than that of normal controls.

As discussed above, molecular cloning of the cDNA for EPR-1 revealed the sequence of a novel transmembrane molecule, characterized by a unique cysteine-rich extracellular module and by a cytoplasmic domain with numerous potential serine/threonine phosphorylation sites. Ligand binding to EPR-1 induces lymphocyte mitogenesis, and selected monoclonal antibodies to EPR-1 completely abolish T cell receptor-mediated normal lymphocyte proliferation. Thus, EPR-1 is likely a novel cellular marker of potential pathophysiologic relevance in CLL, and a member of a previously unrecognized class of mitogenic receptors implicated in growth-associated signalling in normal and leukemic lymphocytes.

Assembly of proteolytic mechanisms on hemopoietic cells is contributed by EPR-1 through its functional recognition of the blood protease factor Xa (Altieri, et al., Id. (1989); Altieri, et al., Id. (1990); Worfolk, et al., Id. (1992)). As previously defined by monoclonal antibody (mAb) reactivity, EPR-1 is a lymphocyte activation-dependent antigen, characterized by an 8- to 10-fold increased surface expression during polyclonal or antigen-specific normal lymphocyte proliferation in vitro (Altieri, et al., Id. (1989); Altieri, et al., Id. (1990)). EPR-1 expression in hemopoietic malignancies was investigated by flow cytometry. As shown in Table 1, anti-EPR-1 mAb 12H1 homogeneously reacted with 51–99% of peripheral lymphocytes isolated from 27 out of 30 CLL patients (90%). As judged by fluorescence intensity, EPR-1 surface density/cell was increased by 5- to 50-fold in CLL samples, as compared with that of normal controls (Table 1). In contrast, no increase in EPR-1$^+$ cells or EPR-1 density/cell was detected by mAb 12H1 in lymphocytes isolated from patients with Hairy Cell Leukemia (HCL), under the same experimental conditions (not shown, n=15).

B. Factor Xa/EPR-1 Interaction

The role of EPR-1 in lymphocyte mitogenesis was investigated in in vitro proliferation experiments. First, it was demonstrated that ligand binding to EPR-1 induces lymphocyte proliferation (see FIG. 4A). Suspensions of EPR-1$^+$ MOLT13 lymphocytes were growth-arrested by a 48-hour incubation under serum-starving conditions (0.5% FCS). Triplicate cultures of quiescent MOLT13 cells were cultivated with increasing concentrations (0.01 to 1 μg/ml) of the natural EPR-1 ligand factor Xa (closed circles), control protein myoglobin (closed squares), or 10% FCS (closed triangles) for 3 days at 37° C. in RPMI 1640 media (Whittaker) plus 0.5% FCS. After a 12 hour pulse with 1 μCi/well $^3$HTdR, wells were harvested and radioactivity incorporated under the various conditions was quantitated in a scintillation β counter. Data±S.E.M. are representative of at least two independent experiments and clearly indicate that occupancy of EPR-1 with its natural ligand, factor Xa, induces proliferation of growth-arrested MOLT13 lymphocytes in a dose-dependent fashion As further shown in FIG. 5A, while no specific interaction of $^{125}$I-factor Xa with wild type CHO cells could be demonstrated, EPR-1 CHO transfectants bound $^{125}$I-factor Xa in a specific and saturable reaction, regulated by an apparent $K_d$ of about 10–15 nM, with maximal association of 80 ng factor Xa/10$^6$ cells.

Figure 16:
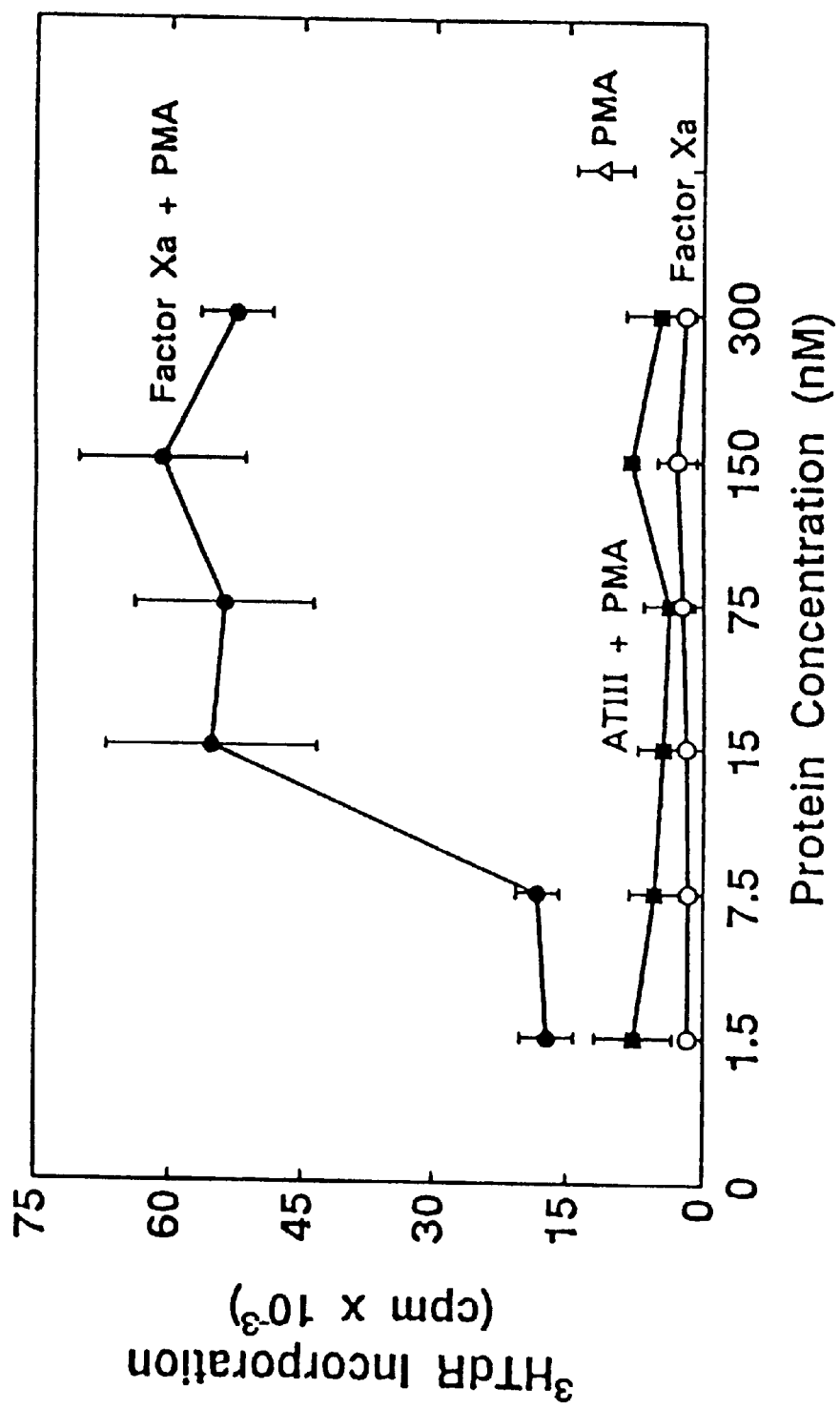
FIG. 16 illustrates the stimulation of PBMC proliferation by factor Xa. $^3$HTdR incorporation (in cpm×10$^{-3}$) is shown on the vertical axis, while protein concentration (in nM) is plotted on the horizontal axis. Data for cultures incubated with factor Xa and PMA (closed circles), ATIII (antithrombin III) and PMA (closed squares), factor Xa alone (open circles) and PMA alone (open triangle) are expressed as mean±S.E.M. of four independent experiments.

FIG. 16 shows that the effect of factor Xa binding to the EPR-1 receptor is the induction of proliferation of PBMCs. In effect, factor Xa acts as a primary mitogenic factor (increasing responder cell concentration) or as a co-mitogen (low responder cell concentration). The role of factor Xa is discussed further in Example 12 hereinbelow.

As shown in FIG. 16, factor Xa binding stimulates PBMC proliferation. $^3$HTdR incorporation (in cpm×10$^{-3}$) is shown on the vertical axis, while protein concentration (in nM) is plotted on the horizontal axis. PBMC at 3×10$^5$/well were incubated with the indicated increasing concentrations of factor Xa in the presence or in the absence of 1 ng/ml PMA (phorbol ester, Sigma, St. Louis, Mo.). Control cultures were incubated with antithrombin III (ATIII) plus PMA under the same experimental conditions. Cell proliferation was quantitated after a three day culture at 37° C. by $^3$HTdR incorporation. Background cpm in the absence of agonists was 3,463±293 cpm (n=4). Data for cultures incubated with factor Xa and PMA (closed circles), ATIII and PMA (closed squares), factor Xa alone (open circles) and PMA alone (open triangle) are expressed as mean±S.E.M. of four independent experiments.

Figure 4A:
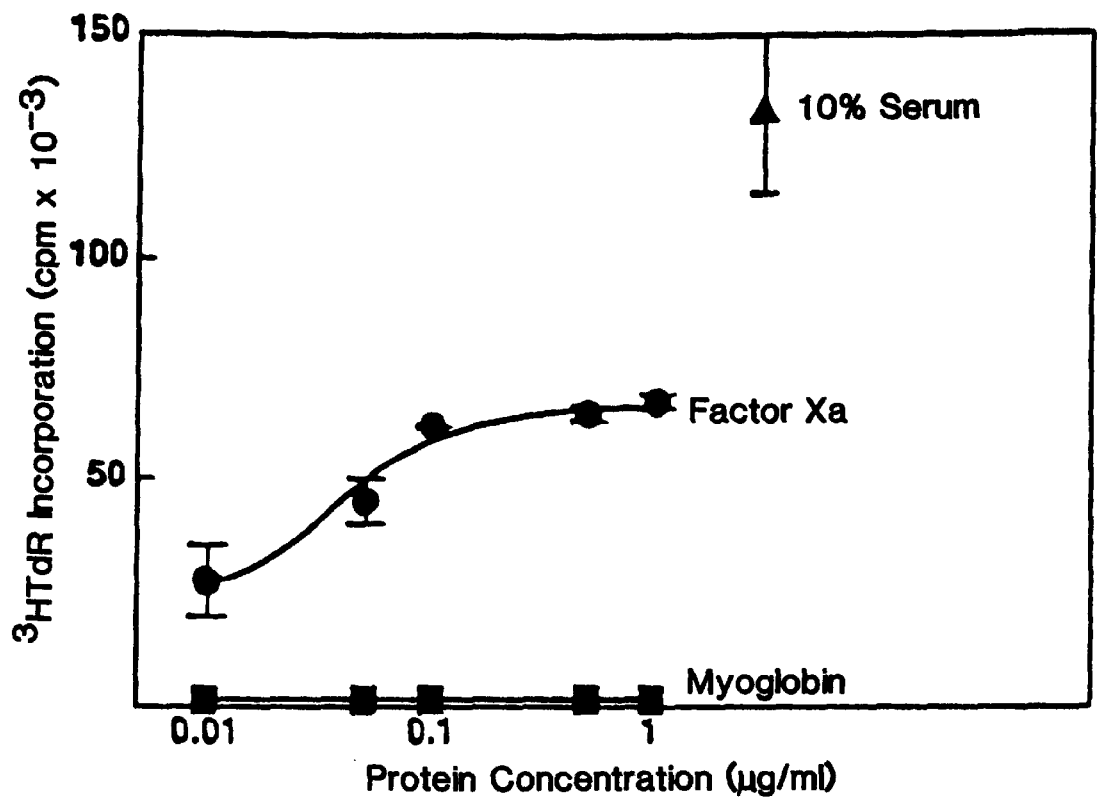
FIG. 4A shows ligand binding to EPR-1 induces lymphocyte proliferation. Lymphocyte proliferation, measured via $^3$HTdR incorporation (cpm$\times 10^{-3}$), is plotted on the vertical axis, whereas protein concentration (in μg/ml) is shown on the horizontal axis. Suspensions of EPR-1$^+$ MOLT13 lymphocytes were growth-arrested by a 48-hour incubation under serum-starving conditions (0.5% Fetal Calf Serum (FCS)). Triplicate cultures of quiescent MOLT13 cells were cultivated with increasing concentrations (0.01 to 1 μg/ml) of the natural EPR-1 ligand factor Xa (closed circles), control protein myoglobin (closed squares), or 10% FCS (closed triangles) for 3 days at 37° C. in RPMI 1640 media (Whittaker) plus 0.5% FCS. After a 12 hour pulse with 1 μCi/well $^3$HTdR, wells were harvested and radioactivity incorporated under the various conditions was quantitated in a scintillation β counter. Data±S.E.M. are representative of at least two independent experiments.
Figure 4B:
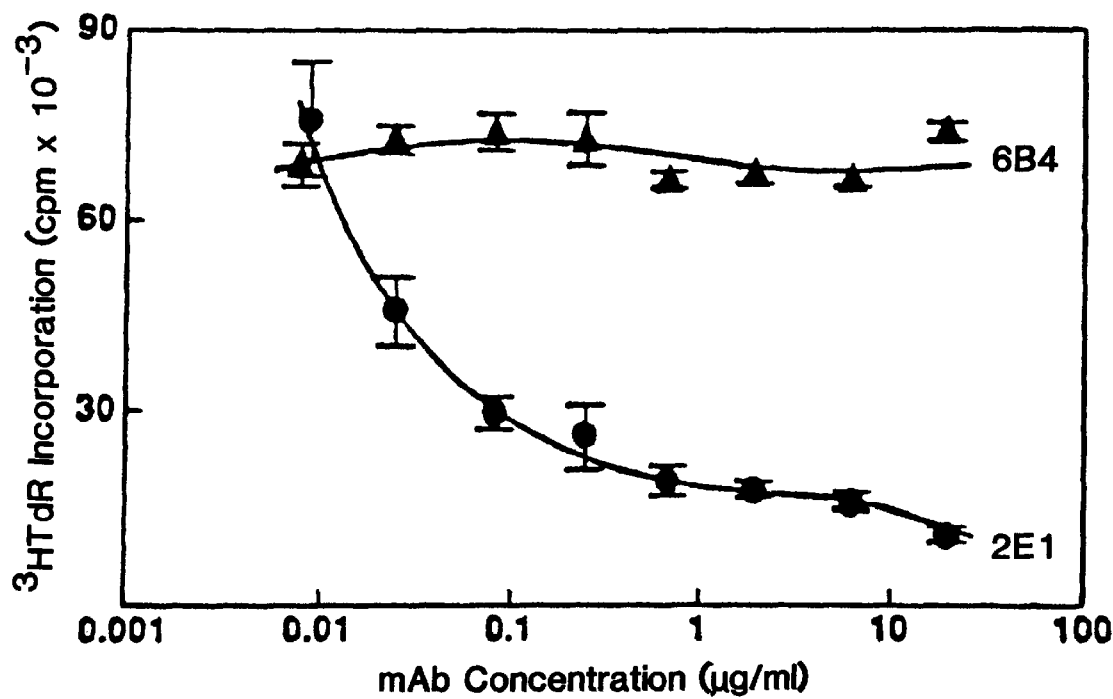
FIG. 4B shows that anti-EPR-1 mAb 2E1 inhibits antigen-specific T cell proliferation. Lymphocyte proliferation, as demonstrated by measurement of $^3$HTdR incorporation (cpm$\times 10^{-3}$), is plotted on the vertical axis, whereas mAb concentration (in μg/ml) is shown on the horizontal axis. Triplicate cultures of peripheral blood mononuclear cells (PBMC) in RPMI 1640 media plus 10% FCS were set up in 96 well microtiter plates ($3 \times 10^5$/well), and preincubated with the indicated increasing concentrations of anti-EPR-1 mAb 2E1 (closed circles) or control mAb 6B4 (closed triangles) for 30 min at 37° C. Cells were stimulated with 1 μg/ml mitogenic anti-CD3 mAb OKT3 and cultivated for 3 days at 37° C. Lymphocyte proliferation was quantitated after a 12 hour pulse with 1 μCi/well $^3$HTdR as described in A. $^3$HTdR incorporation in unstimulated cultures without mAb OKT3 was 353±65 cpm (n=3). Data are expressed as mean±S.E.M. of three independent experiments.

C. Anti-Proliferative Antibodies Interfere with Factor Xa Binding to EPR-1 Receptor Molecule Conversely, as illustrated in FIG. 4B, anti-EPR-1 mAb 2E1 inhibits antigen-specific T cell proliferation. Triplicate cultures of peripheral blood mononuclear cells (PBMC) in RPMI 1640 media plus 10% FCS were set up in 96 well microtiter plates (3×10$^5$/well), and preincubated with the indicated increasing concentrations of anti-EPR-1 mAb 2E1 (closed circles) or control mAb 6B4 (closed triangles) for 30 min at 37° C. Cells were stimulated with 1 μg/ml mitogenic anti-CD3 mAb OKT3 and cultivated for 3 days at 37° C. Lymphocyte proliferation was quantitated after a 12 hour pulse with 1 μCi/well $^3$HTdR as described in A. $^3$HTdR incorporation in unstimulated cultures without mAb OKT3 was 353±65 cpm (n=3). Data are expressed as mean±S.E.M. of three independent experiments.

Occupancy of EPR-1 with its natural ligand, factor Xa (Altieri, et al., Id. (1989); Altieri, et al., Id. (1990); Worfolk, et al., Id. (1992)), has now been shown herein to induce proliferation of growth-arrested MOLT13 lymphocytes in a dose-dependent fashion (FIG. 4A). Secondly, it has now been shown that increasing doses of anti-EPR-1 mAb 2E1 completely inhibited clonotypic lymphocyte proliferation induced by anti-CD3 mAb OKT3 (FIG. 4B). (See also Weber, et al., J. Immunol. 135: 2337–2342 (1985); Geppert, et al., J. Immunol. 138: 1660–1666 (1987).)

Membrane assembly of proteases like thrombin, urokinase, or factor Xa itself is known to initiate DNA synthesis and mitogenesis of normal and transformed cells. (See Vu, et al., Cell 64: 1057–1068 (1991); Kirchheimer, et al., PNAS USA 86: 5424–5428 (1989); and Gasic, et al., PNAS USA 89: 2317–2320 (1992).) As shown here for factor Xa, this mechanism involves a novel receptor recognition, potentially involved in both hemopoietic (Gasic, et al., Id. (1992)) and non-hemopoietic cell mitogenic signalling.

Furthermore, the profound inhibition of clonotypic lymphocyte proliferation produced by mAb 2E1 suggests the participation of as yet unidentified EPR-1 ligand(s) in this mitogenic response, and/or a regulatory role of EPR-1 in intracellular signal transduction through CD3. (See, e.g, Weber, et al., Id.: (1985); Geppert, et al., Id. (1987); Chan, et al., Curr. Opin. Immunol. 4: 246–251 (1992); and Janeway, Ann. Rev. Immunol. 10: 645–674 (1992).) In this context, it is intriguing that the serine-rich EPR-1 cytoplasmic domain was found homologous, at least in part, to Draf-1, a proto-oncogene also implicated in cell division and malignant transformation (Nishida, et al., Id. (1988); Fukui, et al., Mol. Cell. Biol. 7: 1776–1781 (1987)).

Although suggestive for its role in lymphocyte proliferation, further studies are required to delineate the potential pathogenic role and prognostic significance of increased EPR-1 expression in CLL and/or in other malignancies.

Example 7

Tetanus Toxoid Response in HuSCID Mice

In order to evaluate the effect of anti-EPR-1 monoclonal antibody on the secondary human immune response, an anti-EPR-1 antibody was incubated with human peripheral blood lymphocytes (PBLs) in vitro prior to administration of said PBLs to hu-PBL-SCID mice. In one experimental protocol, no further injections of antibody were provided in vivo; in a second protocol, additional antibody was administered on a weekly basis to specified groups, as described further hereinbelow.

As previously noted, the SCID mice used in all the within-described experiments are an ideal and appropriate model for the evaluation of the impact and effect of monoclonal antibodies of the present invention on the human immune system.

A. Administration of Anti-EPR-1 Monoclonal Antibody In Vitro Only

Peripheral blood lymphocytes (PBLs) were obtained from an EBV$^+$ human donor who had not received a tetanus toxoid (TT) boost within the year prior to the collection of PBLs. Non-leaky SCID mice at least 6 weeks old were selected for use in the within-described experiments and were randomly divided into seven groups (groups 1–7) of five mice each.

Anti-EPR-1 monoclonal antibody 2E1 was selected as the experimental antibody. An isotype-matched antibody of irrelevant specificity (antibody 9D4) was selected for use as a control antibody (Cab). Tetanus toxoid (TT) was used as the antigen. Experimental protocols for each of the seven groups were as follows:

| Group 1 (5 mice) | |
|---|---|
| Day 0 - | 50 × 10$^6$ PBL (incubated for 4 hours at 4 × 10$^6$ PBL/ml in RPMI-10% FCS) in Earles-1% BSA (1000 µl) administered I.P. (intraperitoneally) |

| Group 2 (5 mice) | |
|---|---|
| Day 0 - | 50 × 10$^6$ PBL (incubated for 4 hours at 4 × 10$^6$ PBL/ml in RPMI-10% FCS with 10 µg/ml of mAb 2E1) and 100 µg of 2E1 in Earles-1% BSA (1000 µl) administered I.P. |

| Group 3 (5 mice) | |
|---|---|
| Day 0 - | 50 × 10$^6$ PBL (incubated for 4 hours at 4 × 10$^6$ PBL/ml in RPMI-10% FCS with 10 µg/ml of Cab) and 100 µg of Cab in Earles-1% BSA (1000 µl) administered I.P. |

| Group 4 (5 mice) | |
|---|---|
| Day 0 - | 50 × 10$^6$ PBL (incubated for 4 hours at 4 × 10$^6$ PBL/ml in RPMI-10% FCS with 15 µg/ml of TT) and 50 µg of TT in Earles-1% BSA (1000 µl) administered I.P. |

| Group 5 (5 mice) | |
|---|---|
| Day 0 - | 50 × 10$^6$ PBL (incubated for 4 hours at 4 × 10$^6$ PBL/ml in RPMI-10% FCS with 15 µg/ml of TT and 10 µg/ml of 2E1), 50 µg of TT, and 100 µg of 2E1 in Earles-1% BSA (1000 µl) administered I.P. |

| Group 6 (5 mice) | |
|---|---|
| Day 0 - | 50 × 10$^6$ PBL (incubated for 4 hours at 4 × 10$^6$ PBL/ml in RPMI-10% FCS with 15 µg/ml of TT), in Earles-1% BSA (1000 µl) administered I.P. |

| Group 7 (5 mice) | |
|---|---|
| Day 0 - | 50 × 10$^6$ PBL (incubated for 4 hours at 4 × 10$^6$ PBL/ml in RPMI-10% FCS with 15 µg/ml of TT and 10 µg/ml of 2E1), in Earles-1% BSA (1000 µl) administered I.P. |

B. Administration of Anti-EPR-1 Monoclonal Antibody In Vitro and In Vivo

Peripheral blood lymphocytes (PBLs) were obtained from an EBV$^+$ human donor who had not received a tetanus toxoid (TT) boost within the year prior to the collection of PBLs. Non-leaky SCID mice at least 6 weeks old were selected for use in the within-described experiments and were randomly divided into seven groups (groups A–G) of five mice each.

Anti-EPR-1 monoclonal antibody 2E1 was selected as the experimental antibody. An isotype-matched antibody of irrelevant specificity (antibody 9D4) was selected for use as a control antibody (Cab). Tetanus toxoid (TT) wa s used as the antigen. Experimental protocols for each of the seven groups were as follows:

| Group A (5 mice) | |
|---|---|
| Day 0 - | 50 × 10$^6$ PBL (incubated for 4 hours at 4 × 10$^6$ PBL/ml in RPMI-10% FCS) in Earles-1% BSA (1000 µl) administered I.P.$^a$ |
| Day 7 - | Earles-1% BSA (100 µl) I.P. |
| Day 14 - | Earles-1% BSA (100 µl) I.P. |
| Day 21 - | Earles-1% BSA (100 µl) I.P. |
| Day 28 - | Earles-1% BSA (100 µl) I.P. |
| Day 35 - | Earles-1% BSA (100 µl) I.P. |

| Group B (5 mice) | |
|---|---|
| Day 0 - | 50 × 10$^6$ PBL (incubated for 4 hours at 4 × 10$^6$ PBL/ml in RPMI-10% FCS with 10 µg/ml of mAb 2E1) and 100 µg of 2E1 in Earles-1% BSA (1000 µl) administered I.P. |
| Day 7 - | 100 µg of 2E1 in Earles-1% BSA (100 µl) I.P. |
| Day 14 - | 100 µg of 2E1 in Earles-1% BSA (100 µl) I.P. |
| Day 21 - | 100 µg of 2E1 in Earles-1% BSA (100 µl) I.P. |
| Day 28 - | 100 µg of 2E1 in Earles-1% BSA (100 µl) I.P. |
| Day 35 - | 100 µg of 2E1 in Earles-1% BSA (100 µl) I.P. |

| Group C (5 mice) | |
|---|---|
| Day 0 - | 50 × 10$^6$ PBL (incubated for 4 hours at 4 × 10$^6$ PBL/ml in RPMI-10% FCS with 10 µg/ml of Cab) and 100 µg of Cab in Earles-1% BSA (1000 µl) administered I.P. |
| Day 7 - | 100 µg of Cab in Earles-1% BSA (100 µl) I.P. |
| Day 14 - | 100 µg of Cab in Earles-1% BSA (100 µl) I.P. |
| Day 21 - | 100 µg of Cab in Earles-1% BSA (100 µl) I.P. |
| Day 28 - | 100 µg of Cab in Earles-1% BSA (100 µl) I.P. |
| Day 35 - | 100 µg of Cab in Earles-1% BSA (100 µl) I.P. |

| Group D (5 mice) | |
|---|---|
| Day 0 - | 50 × 10$^6$ PBL (incubated for 4 hours at 4 × 10$^6$ PBL/ml in RPMI-10% FCS with 15 µg/ml of TT) and 50 µg of TT in Earles-1% BSA (1000 µl) administered I.P. |
| Day 7 - | Earles-1% BSA (100 µl) I.P. |
| Day 14 - | Earles-1% BSA (100 µl) I.P. |
| Day 21 - | 50 µg of TT in Earles-1% BSA (100 µl) I.P. |
| Day 28 - | Earles-1% BSA (100 µl) I.P. |
| Day 35 - | Earles-1% BSA (100 µl) I.P. |

| Group E (5 mice) | |
|---|---|
| Day 0 - | 50 × 10$^6$ PBL (incubated for 4 hours at 4 × 10$^6$ PBL/ml in RPMI-10% FCS with 15 µg/ml of |

|       | |
|-------|--|
|       | TT and 10 μg/ml of 2E1), 50 μg of TT, and 100 μg of 2E1 in Earles-1% BSA (1000 μl) administered I.P. |
| Day 7 - | 100 μg of 2E1 in Earles-1% BSA (100 μl) I.P. |
| Day 14 - | 100 μg of 2E1 in Earles-1% BSA (100 μl) I.P. |
| Day 21 - | 50 μg of TT and 100 μg of 2E1 in Earles-1% BSA (100 μl) I.P. |
| Day 28 - | 100 μg of 2E1 in Earles-1% BSA (100 μl) I.P. |
| Day 35 - | 100 μg of 2E1 in Earles-1% BSA (100 μl) I.P. |
|       | Group F (5 mice) |
| Day 0 - | 50 × 10$^6$ PBL (incubated for 4 hours at 4 × 6 PBL/ml in RPMI-10% FCS with 15 μg/ml of TT), in Earles-1% BSA (1000 μl) administered I.P. |
|       | Group G (5 mice) |
| Day 0 - | 50 × 10$^6$ PBL (incubated for 4 hours at 4 × 10$^6$ PBL/ml in RPMI-10% FCS with 15 μg/ml of TT and 10 μg/ml of 2E1), in Earles-1% BSA (1000 μl) administered I.P. |

[a]I.P. = intraperitoneally

Mice were bled on days 2, 14, 21, 28, 35, 42, and 60, in both protocols. Human IgG serum levels were determined by particle fluorescence concentration immunoassay on a Pandex automated apparatus, while human IgG anti-TT levels were determined using standard ELISA assay methods. High resolution electrophoresis was also performed on the collected sera. Sick mice were sacrificed and autopsies performed (data not shown).

Figure 6:
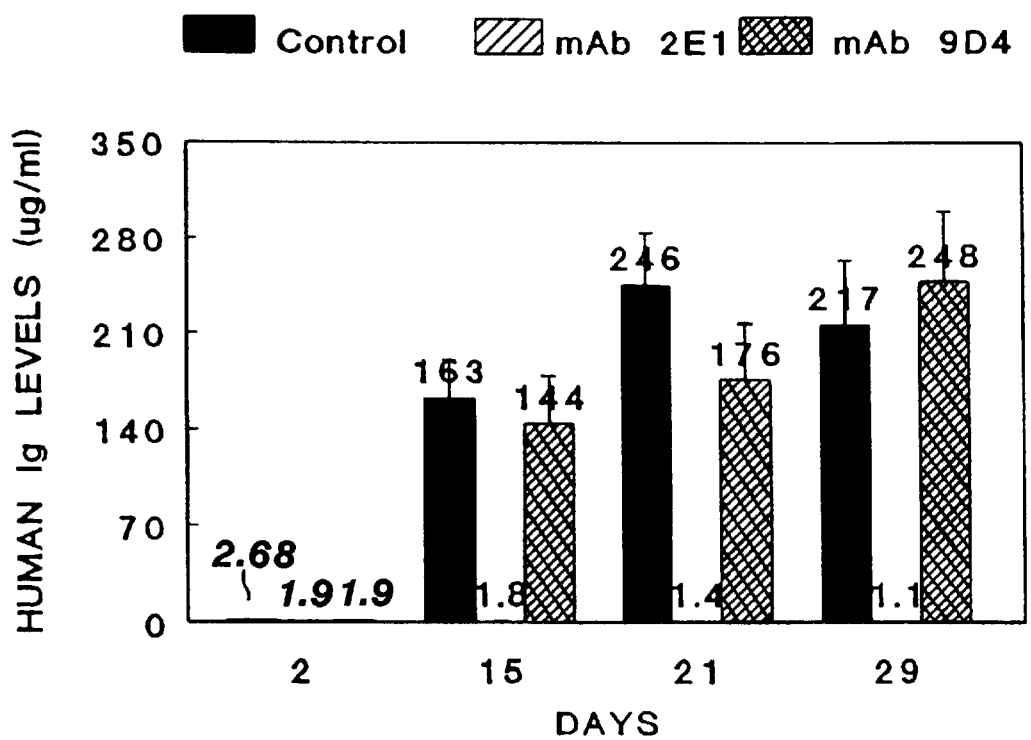
FIG. 6 illustrates the results of in vitro studies using tetanus toxoid. Human immunoglobulin (Ig) levels in µg/ml are expressed on the vertical axis, while the number of days is indicated on the horizontal axis. The tetanus toxoid response in huSCID mice and the effect of mAb 2E1 thereon in vitro is indicated as follows: controls (dark bars) and those given 9D4 (cross-hatched bars) are clearly shown to give a strong response, whereas the human Ig levels are negligible in the huSCID mice given 2E1 (gray or striped bars).

Results of the tetanus toxoid studies described in section A herein are illustrated in FIG. 6 and may be summarized as follows. Human immunoglobulin (Ig) levels in μg/ml are expressed on the vertical axis, while the number of days is indicated on the horizontal axis. The tetanus toxoid response in huSCID mice and the effect of mAb 2E1 thereon in vitro is indicated as follows: controls (dark bars) and those given 9D4 (cross-hatched bars) are clearly shown to give a strong response, whereas the human Ig levels are negligible in the huSCID mice given 2E1 (gray or striped bars).

The corresponding values are as follows:

| DAY | CONTROL | 2E1 | 9D4 |
|-----|---------|-----|-----|
| 2   | 2.68    | 1.9 | 1.9 |
| 15  | 163     | 1.8 | 144 |
| 21  | 246     | 1.4 | 176 |
| 29  | 217     | 1.1 | 248 |

Clearly, response to tetanus toxoid response in huSCID mice receiving mAb 2E1 was practically nonexistent, evidencing a complete immunosuppressive effect.

Figure 7:
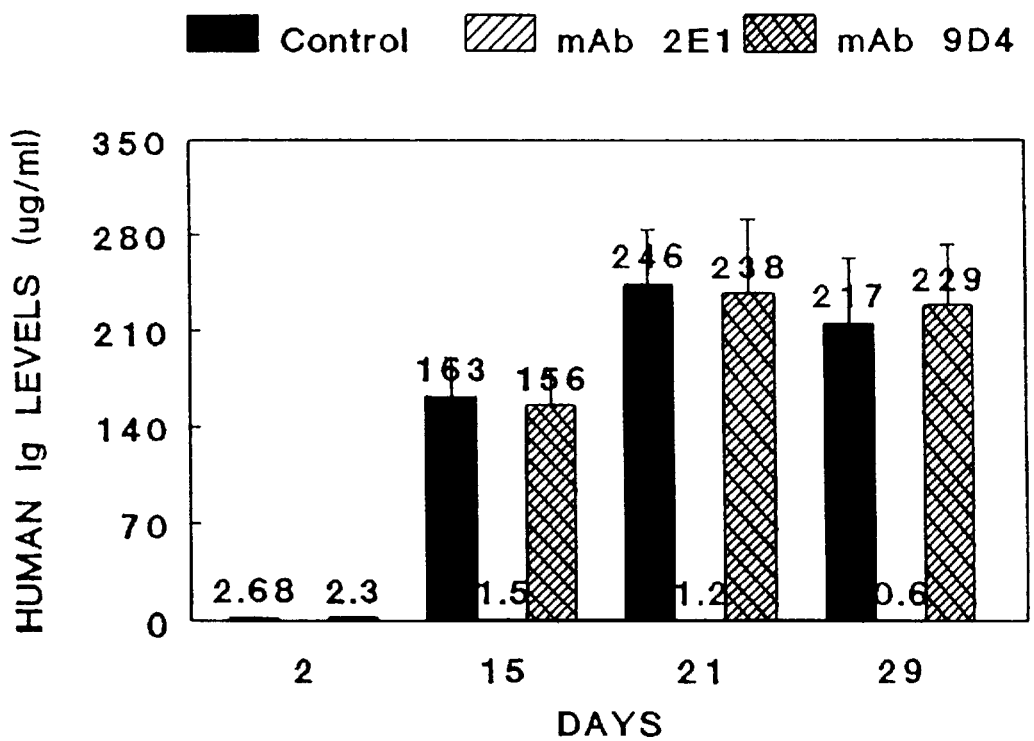
FIG. 7 illustrates the results of in vivo tetanus toxoid studies. Human immunoglobulin (Ig) levels in µg/ml are expressed on the vertical axis, while the number of days is indicated on the horizontal axis. The tetanus toxoid response in huSCID mice and the effect of mAb 2E1 thereon in vivo is indicated as follows: controls (dark bars) and those given 9D4 (cross-hatched bars) are clearly shown to give a strong response, whereas the human Ig levels are negligible in the huSCID mice given 2E1 (gray or striped bars).

Results of the tetanus toxoid studies described in section B herein are illustrated in FIG. 7 and may be summarized as follows. Human immunoglobulin (Ig) levels in μg/ml are expressed on the vertical axis, while the number of days is indicated on the horizontal axis. The tetanus toxoid response in huSCID mice and the effect of mAb 2E1 thereon in vivo is indicated as follows: controls (dark bars) and those given 9D4 (cross-hatched bars) are clearly shown to give a strong response, whereas the human Ig levels are negligible in the huSCID mice given 2E1 (gray or striped bars).

The corresponding values are as follows:

| DAY | CONTROL | 2E1 | 9D4 |
|-----|---------|-----|-----|
| 2   | 2.68    | 0   | 2.3 |
| 15  | 163     | 1.5 | 156 |
| 21  | 246     | 1.2 | 238 |
| 29  | 217     | 0.6 | 229 |

As in FIG. 6 above, the response to tetanus toxoid response in huSCID mice receiving mAb 2E1 was again practically nonexistent, evidencing a complete immunosuppressive effect.

Example 8

Inhibition of Proliferation by Anti-EPR-1 mAbs

A. Assay Protocols

Proliferation, thymidine incorporation, and lymphokine assays were essentially conducted according to the procedures described in Gimmi, et al., PNAS USA 88: 6575–6579 (1991), Rothman, et al., J. Immunol. 147: 2493–2499 (1991), or Lue, et al., J. Immunol. 147: 1134–1138 (1991), which are essentially as follows.

1. Proliferation Assay

PBMCs (3×10$^6$ cells/ml) or T cells (1.5×10$^6$ cells/ml) were cultivated in complete media consisting of RPMI 1640 containing heat-inactivated FCS (RPMI-10% FCS), 2 mM glutamine, 1 mM sodium pyruvate, and antibiotics (e.g., penicillin (100 units/ml), streptomycin sulfate (100 μg/ml), and gentamycin sulfate (5 μg/ml)). Cells were cultured at a concentration of 3×10$^6$ cells per 200 μl of medium in triplicate samples in a 96-well flat-bottomed microtiter plate at 37° C. for 3–7 days in 5% CO$_2$. Cells were cultured in medium and with the appropriate stimuli added.

OKT3 (0.5 μg/well) was coated onto flat bottom, 96-well microtiter plates by diluting OKT3 IgG in sodium carbonate buffer (0.05M, pH 9.6) and adding 100 μl/well. Plates were incubated for 18 hours at 4° C.; each plate was washed twice with PBS and then with complete medium.

PBL were cultured with PHA (4 μg/ml) or soluble OKT3 mAb (1 μg/ml) for 3–5 days. T cells were cultured for 3 days with OKT3 IgG previously coated onto microtiter plates. For mixed lymphocyte reactions, PBL (2×10$^7$ cells/ml) were incubated with untreated allogenic PBL (1.5×10$^6$ cells/ml) in complete RPMI 1640 medium for 5 days in flat bottom, 96-well microtiter plates in 200 μl total volume in a humidified atmosphere of 5% CO$_2$ in air.

To measure [$^3$H]TdR incorporation, 1 μCi of [$^3$H]TdR (2 Ci/mmol., Amersham International, Indianapolis, Ind.) was added to cultures in triplicate 12 hours before cells were harvested onto filter paper (PHD Cell Harvester, Cambridge, Mass.).

Antibody was added at 10 μg/ml to the 96-well flat-bottomed microtiter plates and incubated at 37° C. for 1 hour.

2. Thymidine Incorporation Assay

Thymidine incorporation was used as an index of mitogenic activity. During the last 12 hours of the 72-hour culture, the cells were incubated with 1 μCi (1 microCurie or 37 kBq) of [methyl-$^3$H] thymidine (ICN Flow, Costa Mesa, Calif.). The cells were harvested onto filters and the radioactivity on the dried filters was measured in a scintillation counter.

3. Lymphokine Assay

Culture supernatants were collected 24 hours after the initiation of the culture and IL-1 or IL-2 concentrations were assayed in duplicate using an ELISA kit according to the manufacturer's instructions (Quantikine; R&D Systems, Minneapolis, Minn.).

B. Use of Response-Activating Antigens

Figure 8A:
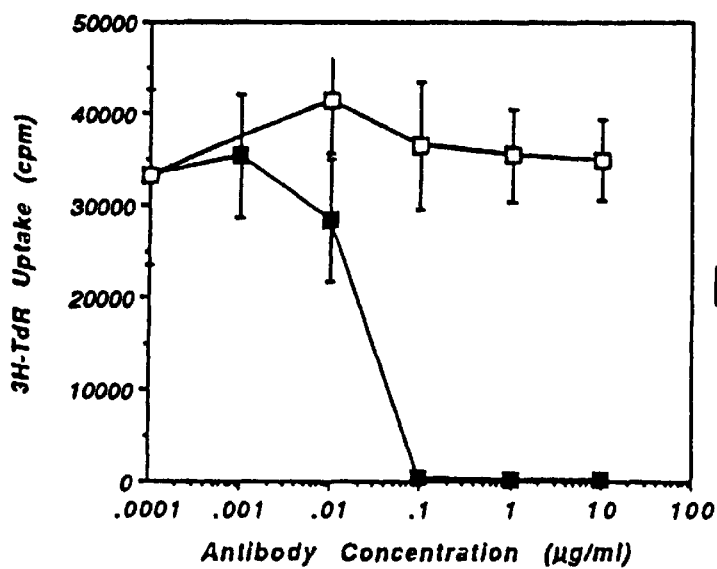
FIGS. 8A–C illustrate the inhibition of T cell proliferation by anti-EPR-1 monoclonal antibody 2E1. In all three figures, 3H-TdR uptake (in cpm, vertical axis) is plotted against antibody concentration (in µg/ml, horizontal axis).
Figure 8B:
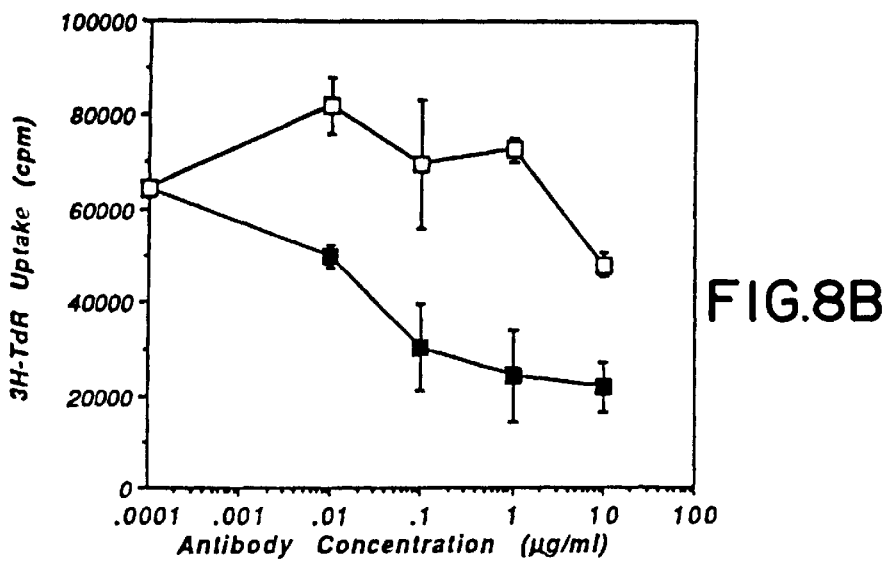
Figure 8C:
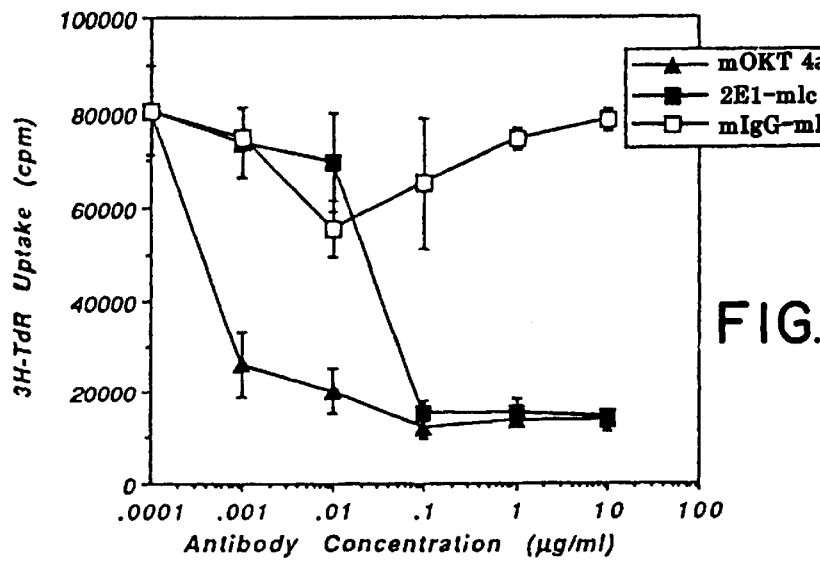

FIGS. 8A–C illustrate the inhibition of T cell proliferation by anti-EPR-1 monoclonal antibody 2E1. In all three figures, $^3$H-TdR uptake (in cpm, vertical axis) is plotted against antibody concentration (in μg/ml, horizontal axis). In FIG. 2A, 1 μg/ml soluble OKT3 is utilized to activate T-cell response. Increasing amounts of anti-EPR-1 antibody 2E1 (closed squares) and mIgG (murine IgG; open squares) were added to the stimulated cells, as indicated on the horizontal axis (Ab concentration, in μg/ml), and $^3$-HTdR uptake (in cpm) was determined.

In FIG. 8B, 0.5 μg/ml immobilized OKT3 was utilized to activate T-cell response. Increasing amounts of 2E1 (closed squares) and of mIgG (open squares) were added to the stimulated cells, as indicated on the horizontal axis, and $^3$H-TdR uptake (in cpm) was determined.

In FIG. 8C, a mixed lymphocyte culture (mlc) was used. (MLCs are generally alloreactive, as non-compatible cells in such cultures activate each other.) Varying concentrations of mOKT4a (closed triangles), 2E1 (closed squares) and mIgG (open squares) were added, as indicated on the horizontal axis, and $^3$H-TdR uptake was determined.

As clearly indicated in FIGS. 8A–8C, administration of anti-EPR-1 mAb 2E1 significantly inhibited the proliferation of PBLs, regardless of the stimulating factor, producing significant inhibitory effects at concentrations as low as 0.1 μg/ml.

C. Use of Polyclonal Lectins

Polyclonal lectins phytohemagglutinin (PHA) and concanavalin A (ConA) were used as stimulants of T-cell proliferation. PHA (4 μg/ml) or ConA (1 μg/ml) was administered to PBMCs, according to the protocol described in Section A above. The indicated amounts of control (6B4) or anti-EPR-1 (2E1) antibody were administered, and $^3$H-TdR incorporation was determined, as described.

Figure 9A:
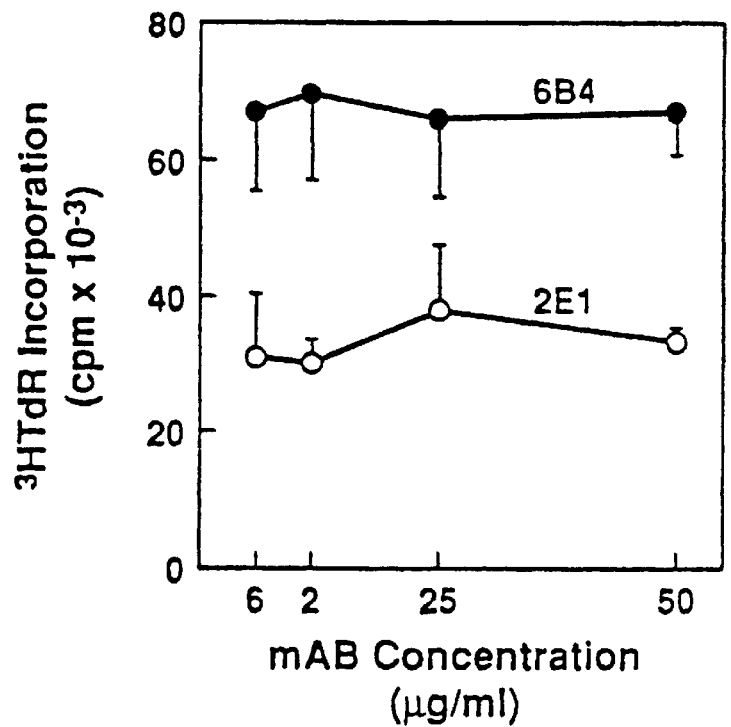
FIG. 9A illustrates the effect of administration of mAb 2E1 on polyclonal T cell proliferation in cells stimulated with PHA. Control antibody 6B4 (closed circles) and anti-EPR-1 antibody 2E1 (open circles) were administered in amounts varying from about 6 to about 50 µg/ml. Antibody concentration (in µg/ml) is plotted on the horizontal axis, with $^3$H-TdR incorporation (in cpm×10$^{-3}$) shown on the vertical axis.

FIG. 9A illustrates the effect of administration of mAb 2E1 in PHA-stimulated cells. Control antibody 6B4 (closed circles) and anti-EPR-1 antibody 2E1 (open circles) were administered in amounts varying from about 6 to about 50 μg/ml. Antibody concentration (in μg/ml) is plotted on the horizontal axis, with $^3$H-TdR incorporation (in cpm×10$^{-3}$) shown on the vertical axis.

Figure 9B:
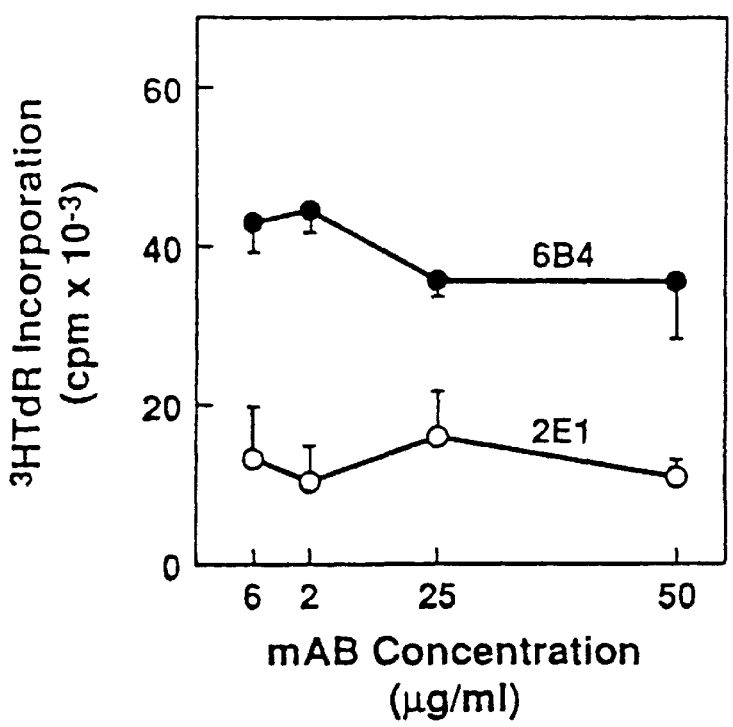
FIG. 9B illustrates the effect of administration of mAb 2E1 in polyclonal T cell proliferation in cells stimulated with ConA. Control antibody 6B4 (closed circles) and anti-EPR-1 antibody 2E1 (open circles) were administered in amounts varying from about 6 to about 50 µg/ml. Antibody concentration (in µg/ml) is plotted on the horizontal axis, with $^3$H-TdR incorporation (in cpm×10$^{-3}$) shown on the vertical axis.

FIG. 9B illustrates the effect of administration of mAb 2E1 in ConA-stimulated cells. Control antibody 6B4 (closed circles) and anti-EPR-1 antibody 2E1 (open circles) were administered in amounts varying from about 6 to about 50 μg/ml. Antibody concentration (in μg/ml) is plotted on the horizontal axis, with $^3$H-TdR incorporation (in cpm×10$^{-3}$) shown on the vertical axis.

Results in both experiments indicate that administration of relatively small amounts of 2E1 limits the progress of lymphocyte proliferation.

D. Non-Lethality of mAbs

PBLs were prepared as described above (see Example 1). Anti-EPR-1 mAb 2E1 or irrelevant control mAb 12E7 were administered, where noted, at a concentration of 10 μg/ml unless indicated otherwise. Anti-CD3 mAb OKT3 (IgG2a) (ATCC, Bethesda, Md.) was used in "soluble" form and was added to the cultures at a concentration of 1 μg/ml. Proliferation and thymidine incorporation assays were conducted according to the procedures described in Gimmi, et al., *PNAS USA* 88: 6575–6579 (1991), which are essentially as follows.

Lymphocytes were incubated in RPMI 1640 containing FCS (RPMI-10% FCS), 2 mM glutamine, 1 mM sodium pyruvate, penicillin (100 units/ml), streptomycin sulfate (100 μg/ml), and gentamycin sulfate (5 μg/ml). Cells were cultured at a concentration of 5×10$^4$ cells per 200l of medium in triplicate samples in a 96-well flat-bottomed microtiter plate at 37° C. for 3 days in 5% CO$_2$. Cells were cultured in medium and with the appropriate stimuli added. Cells were stimulated with PMA (Calbiochem, San Diego, Calif.) at 1 ng/ml. Antibody was added at 10 μg/ml to the 96-well flat-bottomed microtiter plates and incubated at room temperature for 1 hour.

Thymidine incorporation was used as an index of mitogenic activity. During the last 12 hours of the 72-hour culture, the cells were incubated with 1 μCi (1 microCurie or 37 kBq) of [methyl-$^3$H] thymidine (ICN Flow, Costa Mesa, Calif.). The cells were harvested onto filters and the radioactivity on the dried filters was measured in a scintillation counter.

Figure 10:
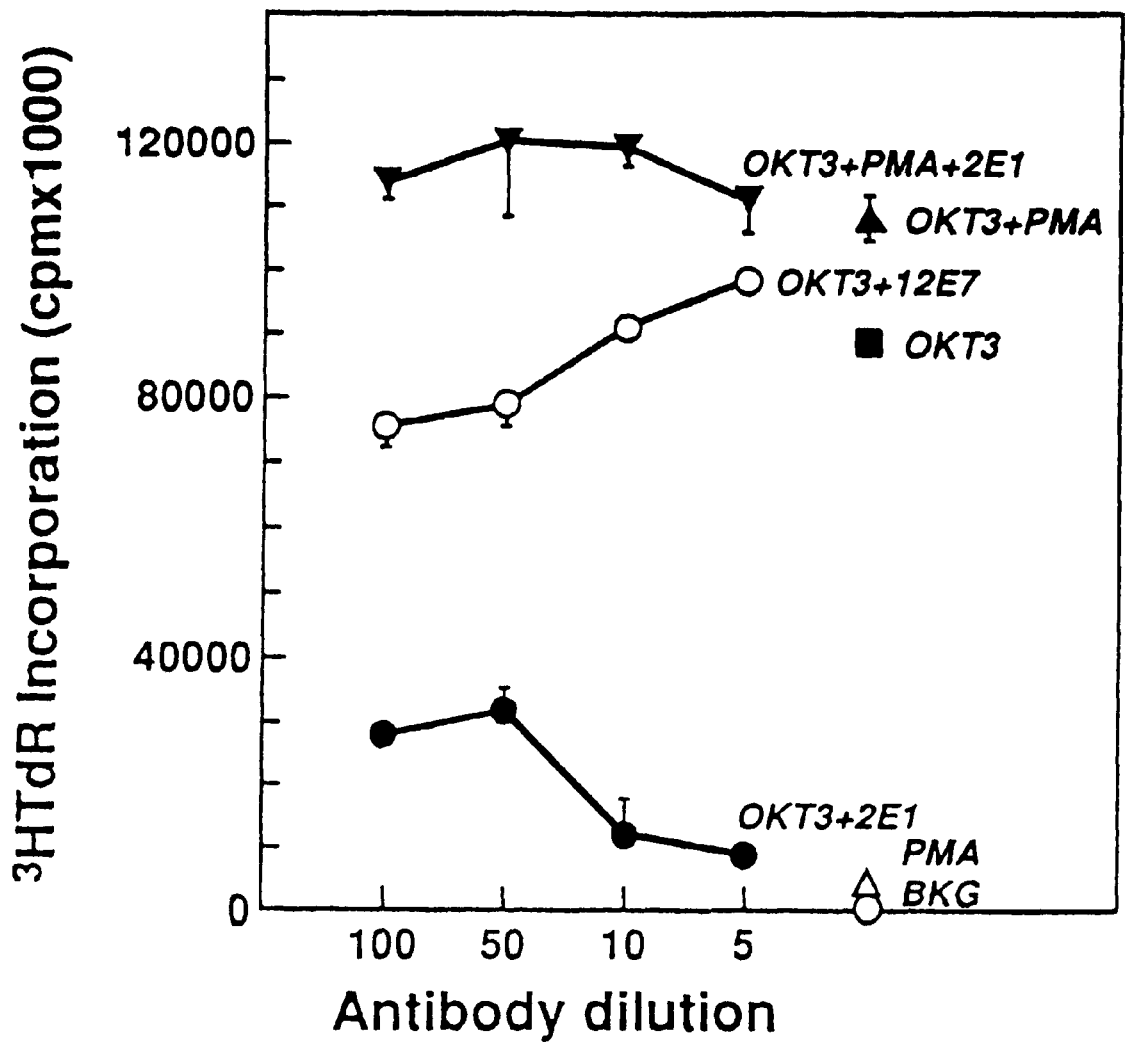
FIG. 10 demonstrates that the anti-EPR-1 monoclonal antibody is non-lethal to the cells to which it is administered. Conversely, the inhibitory property of the antibody is reversible, as illustrated. Antibody dilution (horizontal axis) and $^3$H-TdR incorporation (vertical axis) are determined pursuant to the recited protocol. Cells were stimulated with OKT3+PMA+2E1 (closed, inverted triangles); OKT3+PMA (closed triangles); OKT3 alone (closed square); OKT3+2E1 (closed circles); or PMA alone (open triangle) are indicated, as is background (BKG, open circle).

FIG. 10 demonstrates that the anti-EPR-1 monoclonal antibody is non-lethal to the cells to which it is administered. Conversely, the inhibitory property of the antibody is reversible, as illustrated. Antibody dilution (horizontal axis) and $^3$H-TdR incorporation (vertical axis) are determined pursuant to the recited protocol. Cells were stimulated with OKT3+PMA+2E1 (closed, inverted triangles); OKT3+PMA (closed triangles); OKT3 alone (closed square); OKT3+2E1 (closed circles); or PMA alone (open triangle) are indicated, as is background (BKG, open circle). As illustrated, as 2E1 was gradually withdrawn, the cells resumed their proliferative activities, with no apparent loss of viability.

Example 9

Effect of Anti-EPR-1 mAbs on Cytokine Release

PBLs were prepared as described above (see Example 1). Anti-EPR-1 mAb 2El or mouse IgG was administered, where noted, at a concentration of 10 μg/ml unless indicated otherwise. Anti-CD3 mAb OKT3 (IgG2a) (ATCC, Bethesda, Md.) was added to the cultures at a concentration of 1 μg/ml. Proliferation, thymidine incorporation, and lymphokine assays were essentially conducted according to the procedures described in Example 8 above.

Figure 11A:
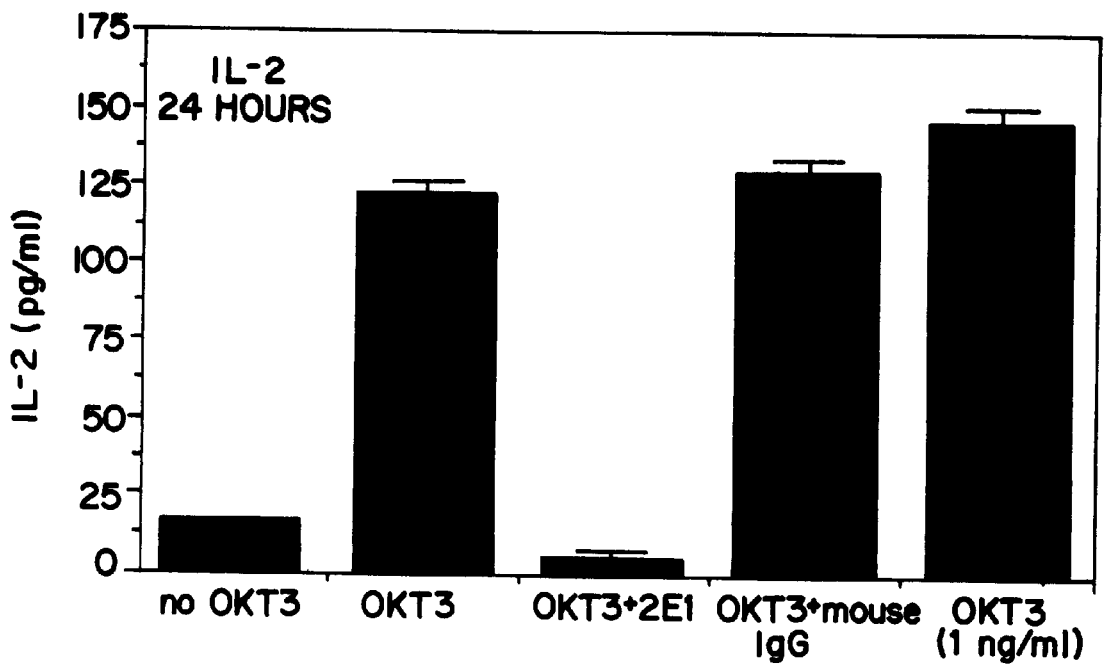
Figure 11B:
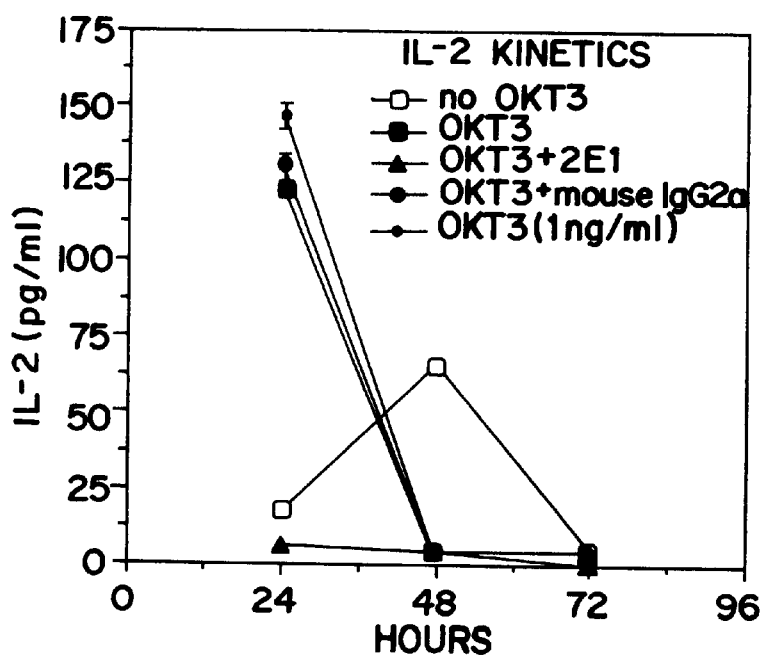
Figure 12A:
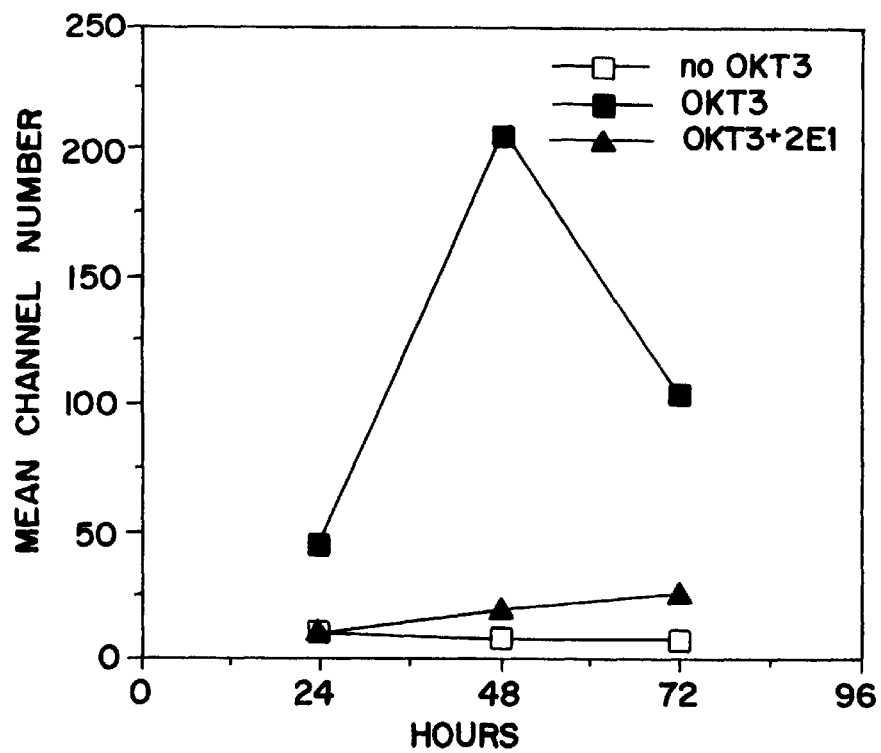
FIGS. 12A and B show that IL-2 receptor (p55) expression is also diminished in OKT3-stimulated wells receiving 2E1.
Figure 12B:
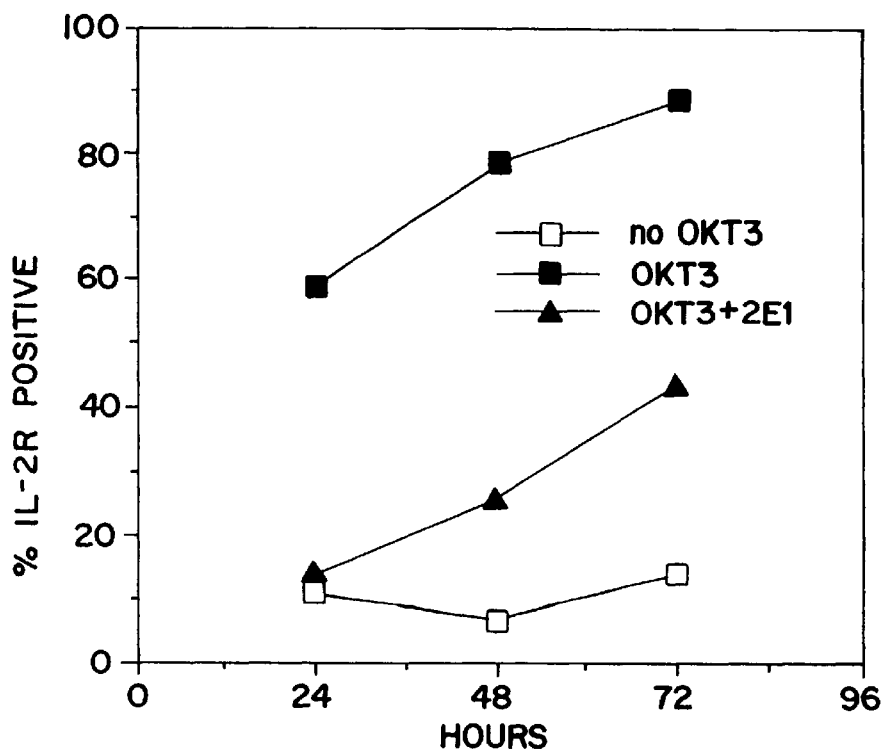
In FIG. 12B, % IL-2 R (IL-2 receptor) positive cells (vertical axis) are plotted against time in hours, as in FIG. 12A. In both FIGS. 12A and B, data points are indicated for cells receiving no OKT3 (open squares); OKT3 (closed squares); and OKT3+2E1 (closed triangles). (At all data points, the amount of OKT3 administered was 1 µg/ml, except where indicated otherwise.)

FIGS. 11A, 11B, and 12 show that 2E1 inhibits IL-2 receptor expression and IL-2 generation. IL-2 concentrations were assayed as described above 24, 48, and 72 hours after OKT3 stimulation. After 24 hours, small amounts of IL-2 were detected in the supernatant following 2E1 administration, as shown, while substantial amounts of IL-2 were present in all other OKT3-stimulated wells. In FIGS. 11A and B, IL-2 generation is minimal after 24 hours in wells receiving 2E1. No IL-2 was detected in wells receiving 2E1 at 48 or 72 hours post-stimulation (FIG. 11B FIG. 12 shows that IL-2 receptor (p55) expression is also diminished in OKT3-stimulated wells receiving 2E1. The moderate increase in IL-2 receptor expression in OKT3+2E1 wells is most likely due to cells being "pre-committed" to receptor expression prior to the administration of 2E1.

Figure 13A:
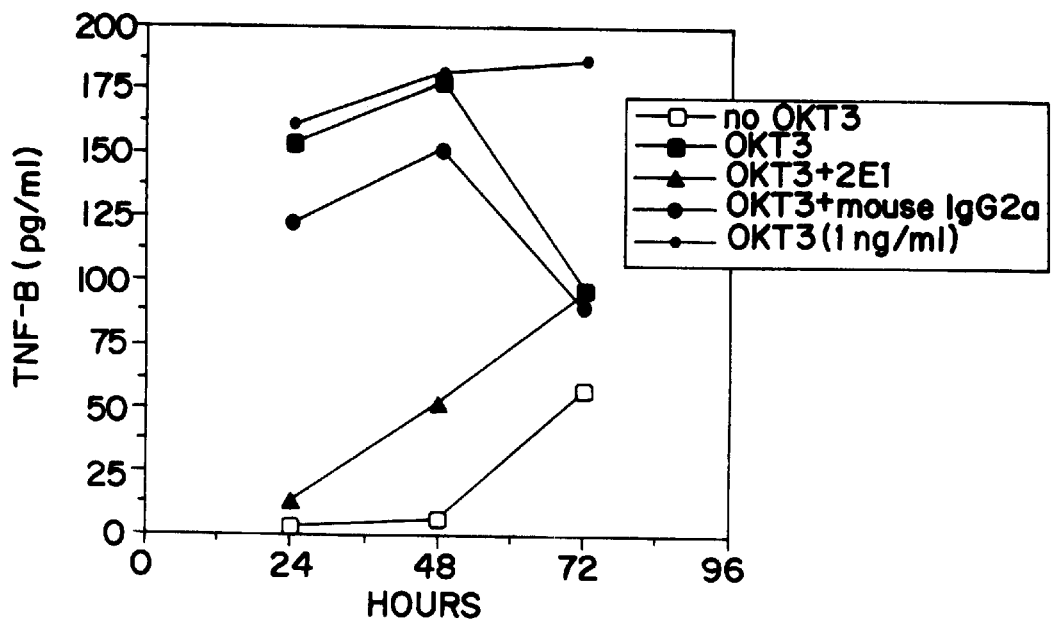
FIGS. 13A and B illustrate that 2E1 inhibits the synthesis of TNF-β in OKT3-stimulated cells.
Figure 13B:
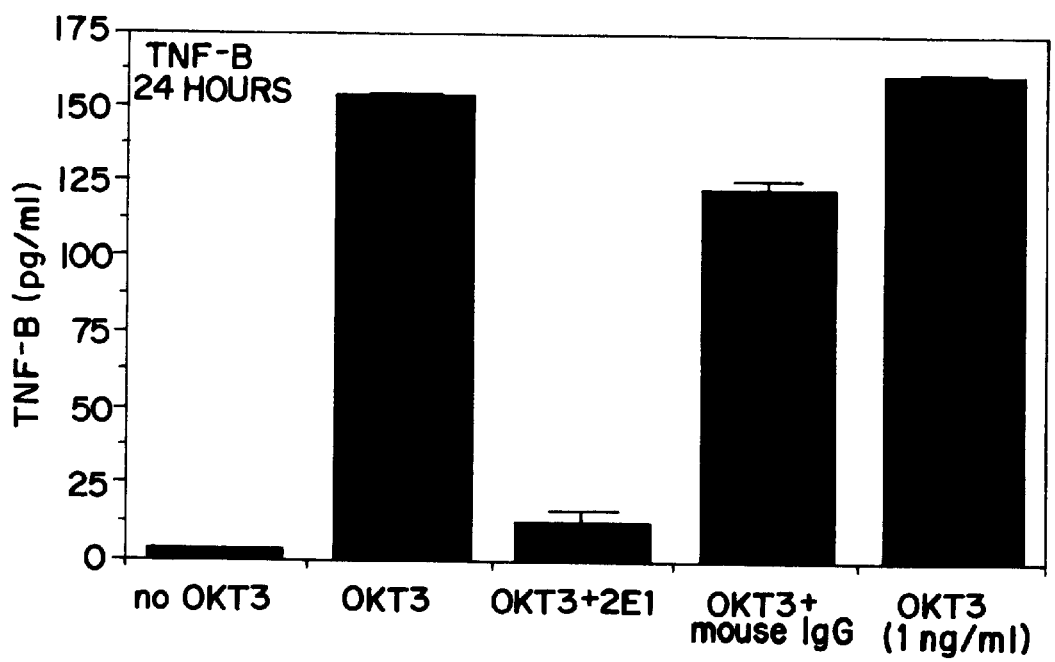
In FIG. 13B, TNF-β levels determined 24 hours after stimulation is shown. On the vertical axis, TNF-β (pg/ml) is illustrated; on the vertical axis, bars representing no OKT3, OKT3, OKT3+2E1, OKT3+mouse IgG2a, and OKT3 (1 ng/ml) are indicated. As before, 1 µg/ml of OKT3 was administered as a stimulant, except where indicated otherwise.

FIGS. 13A and B illustrate that 2E1 inhibits the synthesis of TNFβ in OKT3-stimulated cells. 2E1 inhibits OKT3-induced TNFβ secretion at 24 hours (A and B), although TNFβ secretion in the presence of 2E1 eventually reaches the level of that secreted in OKT3 stimulated cells receiving mouse IgG2a and those not receiving 2E1 (B).

Figure 14A:
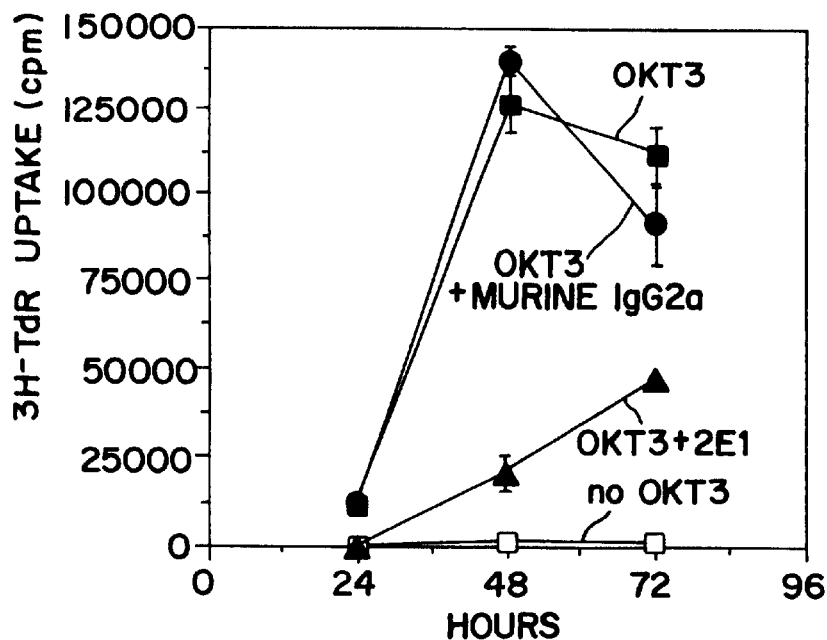
FIGS. 14A and B show a comparison between proliferation (A) and IL-1B synthesis (B) in OKT3 stimulated and unstimulated cells, with and without the administration of 2E1 or murine IgG2a (control antibody).

FIGS. 14A and B show a comparison between proliferation (A) and IL-1B synthesis (B) in OKT3 stimulated and unstimulated cells, with and without the administration of 2E1 or murine IgG2a (control antibody). In FIG. 14A, proliferation, as measured by $^3$H-TdR uptake (in cpm), is plotted against time in hours. Results of the administration of OKT3 (closed squares); OKT3+murine IgG2a (closed circles); OKT3+2E1 (closed triangles); and no OKT3 (open squares) are indicated. Except where indicated otherwise, 1 µg/ml of OKT3 was administered as a stimulant.

Figure 14B:
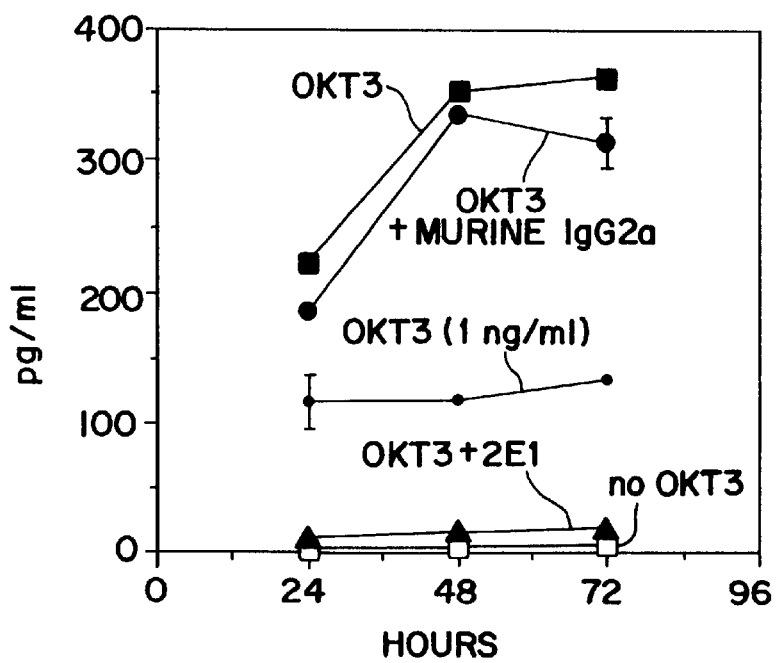
In FIG. 14B, IL-1B production (in pg/ml) is plotted against time in hours. Results of the administration of OKT3 (1 µg/ml, large closed squares); OKT3+murine IgG2a (closed circles); OKT3+2E1 (closed triangles); no OKT3 (open squares); and 1 ng/ml OKT3 (small closed squares) are indicated. Except where indicated otherwise, 1 µg/ml of OKT3 was administered as a stimulant.

In FIG. 14B, IL-1B production (in pg/ml) is plotted against time in hours. Results of the administration of OKT3 (1 µg/ml, large closed squares); OKT3+murine IgG2a (closed circles); OKT3+2E1 (closed triangles); no OKT3 (open squares); and 1 ng/ml OKT3 (small closed squares) are indicated. Except where indicated otherwise, 1 µg/ml of OKT3 was administered as a stimulant.

As shown in FIG. 14A, lymphoproliferation was dramatically curtailed in cells stimulated with OKT3 which also received anti-EPR-1 mAb 2E1. As demonstrated above, cell viability was not affected; rather, lymphoproliferative events were inhibited.

Similarly, the data shown in FIG. 14B demonstrate that administration of mAb 2E1 almost completely inhibits IL-1β production. Even cells receiving almost negligible amounts of OKT3 stimulant (i.e., those receiving 1 ng/ml OKT3) produced significantly greater amounts of IL-1β than did cells given a greater dose of stimulant, which also received 2E1.

Example 10

Effect of Anti-EPR-1 mAbs on Lymphomas

In order to evaluate the effect of anti-EPR-1 monoclonal antibody on the incidence of, and mortality associated with, human lymphoproliferative disease, an anti-EPR-1 antibody was incubated with human peripheral blood lymphocytes (PBLS) in vitro prior to administration of said PBLs to hu-PBL-SCID mice. Additional antibody was then administered on a weekly basis to specified groups, as described further hereinbelow.

Peripheral blood lymphocytes (PBLs) were obtained from two EBV+ human donors. Non-leaky SCID mice at least 6 weeks old were selected for use in the within-described experiments and were randomly divided into six groups (A1–D2) of six mice each, and two groups (E and F) of two mice each.

Anti-EPR-1 monoclonal antibody 2E1 was selected as the experimental antibody. An isotype-matched antibody of irrelevant specificity (antibody 9D4) was selected for use as a control antibody. An irrelevant, non-binding mouse antibody (ir-Ab) isotype-matched with 2E1 was also used. Experimental protocols for the various groups were as follows:

| Groups A1 and A2 (6 mice each) | |
|---|---|
| Day 0 - | 50 × 10⁶ PBL (incubated for 4 hours at 4 × 10⁶ PBL/ml in RPMI-10% FCS) in Earles (1000 µl) administered I.P. |
| Day 7 - | Earles (100 µl) I.P. |
| Day 14 - | Earles (100 µl) I.P. |
| Day 21 - | Earles (100 µl) I.P. |
| Day 28 - | Earles (100 µl) I.P. |
| Day 35 - | Earles (100 µl) I.P. |
| Groups B1 and B2 (6 mice each) | |
| Day 0 - | 50 × 10⁶ PBL (incubated for 4 hours at 4 × 10⁶ PBL/ml in RPMI-10% FCS with 10 µg/ml of mAb 2E1) and 100 µg of 2E1 in Earles (1000 µl) administered I.P. |
| Day 7 - | 100 µg of 2E1 in Earles (100 µl) I.P. |
| Day 14 - | 100 µg of 2E1 in Earles (100 µl) I.P. |
| Day 21 - | 100 µg of 2E1 in Earles (100 µl) I.P. |
| Day 28 - | 100 µg of 2E1 in Earles (100 µl) I.P. |
| Day 35 - | 100 µg of 2E1 in Earles (100 µl) I.P. |
| Groups C1 and C2 (6 mice each) | |
| Day 0 - | 50 × 10⁶ PBL (incubated for 4 hours at 4 × 10⁶ PBL/ml in RPMI-10% FCS with 10 µg/ml of 9D4) and 100 µg of 9D4 in Earles (1000 µl) administered I.P. |
| Day 7 - | 100 µg of 9D4 in Earles (100 µl) I.P |
| Day 14 - | 100 µg of 9D4 in Earles (100 µl) I.P. |
| Day 21 - | 100 µg of 9D4 in Earles (100 µl) I.P. |
| Day 28 - | 100 µg of 9D4 in Earles (100 µl) I.P. |
| Day 35 - | 100 µg of 9D4 in Earles (100 µl) I.P. |
| Groups D1 and D2 (6 mice each) | |
| Day 0 - | 50 × 10⁶ PBL (incubated for 4 hours at 4 × 10⁶ PBL/ml in RPMI-10% FCS with 15 µg/ml of ir-Ab) and 100 µg of ir-Ab in Earles (1000 µl) administered I.P. |
| Day 7 - | 100 µg of ir-Ab in Earles (100 µl) I.P. |
| Day 14 - | 100 µg of ir-Ab in Earles (100 µl) I.P. |
| Day 21 - | 100 µg of ir-Ab in Earles (100 µl) I.P. |
| Day 28 - | 100 µg of ir-Ab in Earles (100 µl) I.P. |
| Day 35 - | 100 µg of ir-Ab in Earles (100 µl) I.P. |
| Group E (2 mice) | |
| Day 0 - | 50 × 10⁶ PBL (incubated for 4 hours at 4 × 10⁶ PBL/ml in RPMI-10% FCS with 10 µg/ml of 2E1) and 100 µg of 2E1 in Earles (1000 µl) administered I.P. |
| Group F (2 mice) | |
| Day 0 - | 50 × 10⁶ PBL (incubated for 4 hours at 4 × 10⁶ PBL/ml in RPMI-10% FCS with 10 µg/ml of 9D4) and 100 µg of 9D4 in Earles (1000 µl) administered I.P. |

Mice were bled on days 2, 15, 30, 60, 90, 120, and 180. In Groups A–D, sick mice were sacrificed and autopsies performed (organs preserved in Bouin's; data not shown). The experiments were also terminated (with autopsies performed on all survivors) when the survival rate in either group is less than 20% (i.e., one mouse). Human IgG/IgM serum levels were determined using a Pandex. As an added check, human IgG anti-TT levels were determined using standard ELISA assay methods. BUN (blood urea nitrogen) assays were also performed in mice from Group A (A-1 and A-2).

In Groups E and F, mice were sacrificed and autopsied 36 hours after PBL transfer to determine whether viable human lymphocytes were present in the blood of animals treated with 2E1; if such cells were present, it would confirm that 2E1 is not cytotoxic. The total number of human peritoneal cells was determined via FACS analysis using anti-human CD45 monoclonal antibody. Peritoneal cell viability was determined using Trypan blue.

Results of the above-noted studies were as follows.

Figure 15:
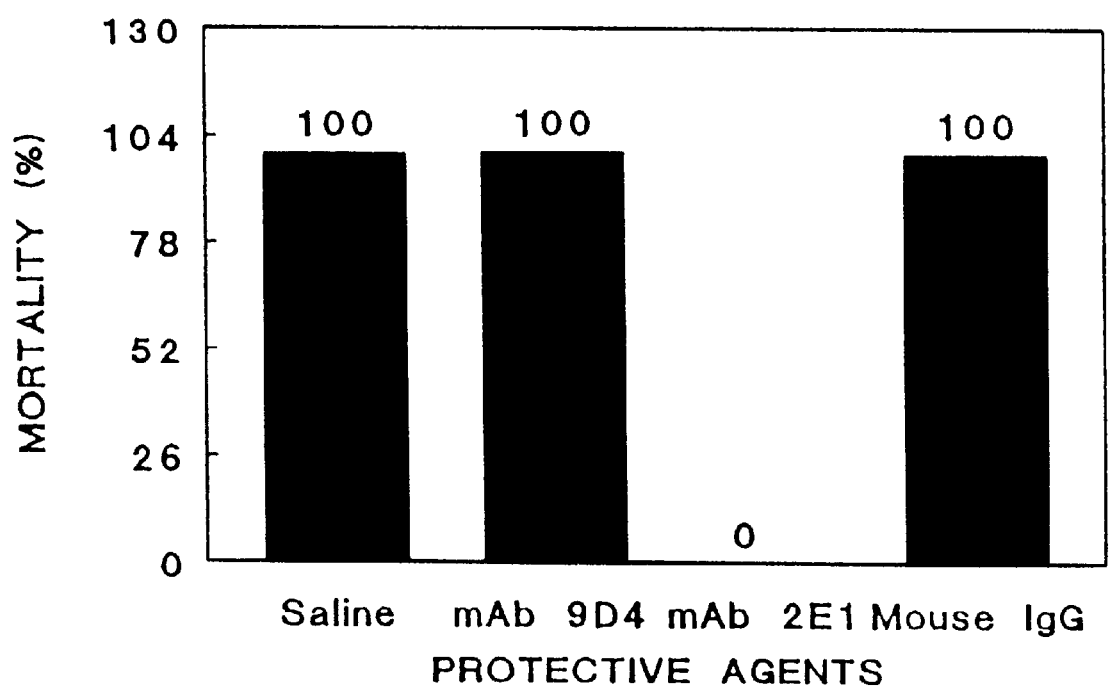
FIG. 15 illustrates the effectiveness of a variety of agents, including saline, mAb 9D4, mAb 2E1, and mouse IgG, in protecting huSCID mice from lymphoma. Mortality (in %) is plotted on the vertical axis. The bars represent mice receiving Earles alone (saline); mAb 9D4; mAb 2E1; and mouse IgG.

Group A: all mice died (histological data not shown)
Group B: all mice receiving 2E1 have survived
Group C: all mice died (histological data not shown)
Group D: all mice died (histological data not shown)
Group E: viable human lymphocytes detected
Group F: viable human lymphocytes detected Data gathered on Groups A–D are further illustrated in FIG. 15, in which mortality (%) is determined for a variety of protective agents, including saline, mAb 9D4, mAb 2E1, and mouse IgG. As shown, only those huSCID mice receiving mAb 2E1 received full protection; conversely, 100% of the mice receiving saline, mAb 9D4, or mouse IgG did not survive.

Example 11

Further Characterization of EPR-1

A. Cellular Distribution of EPR-1.

Monoclonal antibodies against V, the circulating plasma protein that binds the Xa serine protease of coagulation cascade Xa were prepared (Nesheim, M., et al., *J. Biol. Chem.*, 254: 10952 (1979)). In a previous study, it was shown that first-generation anti-EPR-1 mAbs (e.g., mAbs 7G12, 9D4, and 12H1) also reacted with a surface molecule expressed on various myeloid monocytic cell lines (Altieri, et al., *J. Biol. Chem.* 264: 2969 (1989)). Using mAb inhibition studies and receptor-ligand chemical cross-linking, it has been demonstrated that this cell-associated immunoreactive molecule functions as a high affinity ($K_d$=30 nM, n about 150,000) receptor for Xa (Altieri, et al., *J. Biol. Chem.* 264: 2969 (1989)). In this study, mAb panel I was exploited to characterize the cellular distribution and identity of the putative membrane serine protease receptor (EPR-1).

As illustrated in FIG. 1, the reactivity of panel I anti-V mAb is not an eccentric characteristic of transformed in vitro cell lines. mAb 9D4, recognizing a different epitope from the one previously identified by mAb 7G12 (Altieri, *J. Biol. Chem.* 264: 2969 (1989)), reacted with peripheral blood monocytes and dextran-isolated PMN, although with considerable heterogeneity in the latter population (FIG. 1).

When suspensions of PBMC were analyzed by FMF, mAb 7G12, 9D4, and 12H1 consistently reacted with a population of cells (5 to 20%) with forward light scatter characteristic of lymphocytes. Simultaneous two-color FMF analyses were performed to further dissect the phenotype of this lymphoid population. For these studies, suspensions of PBMC were preparatively depleted of adherent cells by either adherence to plastic or by nylon wool fractionation to yield populations enriched in PBL (peripheral blood lymphocyte). Approximately 50 percent of the lymphoid subset identified by mAbs 7G12, 9D4, or 12H1 was OKT3$^-$ and expressed the NK-associated markers CD16 and CD56, as revealed by the simultaneous binding of mAb LEU 11B, 3G8, B73.1, and NKH-1, respectively. Furthermore, when enriched populations of NK cells (<3% CD3$^+$,>85% CD16$^+$) prepared from PBMC by nylon wool fractionation, SRBC (sheep red blood cells) resetting, and negative selection with mAb OKT3, were analyzed by FMF, mAb 7G12 and 9D4 reacted with 68 and 72% of these cells.

The remaining EPR-1$^+$ PBL were phenotypically established as CD3$^+$ lymphocytes. Table 2, hereinafter, shows a representative study of two-color FMF characterization of this EPR-1$^+$ subset. Although double-positive cells coexpressing either CD4 or CD8 were identified, the latter fraction consistently exhibited a higher frequency and a far greater intensity of reaction with EPR-1 marker mAb.

Virtually all EPR-1$^+$ T cells also coexpressed CD11b and CD57(Leu 7), as revealed by mAb OKM1 and HNK-1 respectively, and approximately 70 to 80 percent were CD2$^+$ (OKT11) (Table 2). Although the EPR-1$^+$ subset was predominantly WT31$^+$, approximately 10% of EPR-1$^+$ cells (2% of unfractionated PBL, n=3) were found to be reactive with anti-γ/δTCP mAb δ1. Quantitatively comparable results were also obtained when two-color FMF analyses of PBL were carried out using biotin-conjugated aliquots of the rabbit polyclonal antibody B78.9, or the directly FITC-conjugated mAb 7G12, or 9D4, in combination with the various anti-T cell or anti-NK cell related markers mAb.

TABLE 2

Two-color FMF CHARACTERIZATION OF EPR-1$^+$ subset of T cells[a]

| mAb | Specificity | Relative Percent | |
|---|---|---|---|
| | | Percent Coexpressing PBL | Coexpressing Cells in EPR-1$^+$ Subset |
| OKT3 | CD3 | 9.6 | 73 |
| OKT4 | CD4 | 3.6 | 27 |
| OKT8 | CD8 | 7.4 | 56 |
| OKT11 | CD2 | 10.5 | 79 |
| OKM1 | CD11b | 10.8 | 82 |
| HNK-1 | CD57 | 11.5 | 88 |
| 60.3 | CD18 | 10.7 | 82 |
| WT31 | α/β TCR | 8.1 | 61 |
| δ1 | γ/δ TCR | 1.4 | 10 |
| W6/32 | Class I MHC | 12.0 | 91 |

[a]Two-color FMF analysis of adherent cell-depleted PBL was carried out as follows: Suspensions of PBL were depleted of adherent cells and separately stained with aliquots of anti-CD16 mAb Leu 110, B73.1, or 3G8, or with anti-CD56 mAb NKH-1 (Leu 19) for 30 minutes at 4° C. Cells were washed and incubated with fluorescein-conjugated goat F(ab')$_2$ anti-mouse IgG + IgM for additional 30 minutes at 4° C. After extensive washes, cells were equilibrated with 10 μg/ml of biotinylated mAb 7G12, washed, and incubated with 1/20 dilution of phycoerythrin-streptavidin conjugated reagent. Double-positive cells from a representative study are indicated for the unfractionated PBL population and relative to the EPR-1$^+$ subset (13.1%).

B. EPR-1 is Distinct from CD11b/CD18.

1. Cell Surface Labelling and Immunoprecipitation

Suspensions of PMN at 1×10$^8$/ml were surface iodinated with 5 mCi $^{125}$I-Na by the Iodogen method (Fraker, P. J., et al., *Biochem. Biophys. Res. Commun.*, 80: 849 (1978)). After extensive washes in HEPES saline buffer pH 7.35 cells were lysed in buffer containing 0.5% TRITON X-100 or 10 mM CHAPS, 0.05 M Tris HCl, 0.15 M NaCl, 1 mM benzamidine, 0.1 mM (PPACK=D-Phe-Pro-Arg chloromethylketone; Calbiochem), 25 μg/ml leupeptin, 1 mM PMSF (phenylmethyl sulfonyl fluoride; Calbiochem), pH 8.3 (lysis buffer), for 30 minutes at 4° C. The iodinated lysate was cleared of nuclei and other cellular debris by centrifugation at 14,000×g for 30 minutes at 4° C., and extensively preabsorbed with aliquots of goat anti-mouse IgG+IgM conjugated with SEPHAROSE CL4B (Calbiochem). Aliquots of the $^{125}$I-labelled PMN lysate were separately incubated with mAb 12H1 or 60.3 for 14 hours at 4° C. under agitation.

The immune complexes were precipitated by the addition of goat anti-mouse IgG+IgM conjugated with sepharose CL4B for an additional 6 hours at 4° C., extensively washed in the above lysis buffer, and finally resuspended in 2% SDS sample buffer, pH 6.8, containing 50 mM 2-dithiothreitol as a reducing agent. The samples were immediately boiled for 5 minutes, clarified by centrifugation at 14,000×g for 5 minutes and finally electrophoresed on 7.5% SDS polyacrylamide slab gels in 0.1% SDS. Gels were stained in Coomassie blue R 250, destained in 5% acetic acid, dried and exposed for autoradiography at −70° C. by using KODAK X-OMAT AR X-Ray film and intensifying screens (Cronex, E.I. duPont de Nemours, Wilmington, Del.).

2. Results

Results of these studies verified that EPR-1 is distinct from CD11b/CD18. The expression of EPR-1 on monocytes, PMN, NK cells, and a fraction of T cells that is also predominantly CD8$^+$, appears to mimic the cellular distribution of the leukocyte integrin CD11b/CD18 (Mac-1) (Sanchez Madrid, F., et al., *J. Exp. Med.*, 158: 1785 (1983)).

Therefore, additional studies were designed to establish the reciprocal structure and functional properties of CD11b/CD18 and EPR-1. For these studies, suspensions of PMN that express abundant levels of the CD11/CD18 molecules (Sanchez Madrid, F., et al., *J. Exp. Med.*, 158: 1785 (1983)) were surface labelled with $^{125}$I, detergent-solubilized, and subjected to immunoprecipitation using either the anti-CD18 mAb 60.3 or the anti-EPR-1 mAb 12H1.

From $^{125}$I-labelled PMN lysate, mAb 60.3 immunoprecipitated the polypeptides corresponding to the α subunits of the leukocyte integrins CD11a, CD11b, and CD11c in association with the common β-subunit CD18, in agreement with previous observations (Sanchez Madrid, F., et al., *J. Exp. Med.*, 158: 1785 (1983)). In contrast, under the same conditions, mAb 12H1 immunoprecipitated a major surface component having a molecular mass of about 78±4 kDa. Functionally, CD11b/CD18 and EPR-1 have different ligand recognition specificities. Although CD11b/CD18 has been recognized as an oligo-specific receptor for C3bi, fibrinogen, and factor X (Sanchez Madrid, F., et al., *J. Exp. Med.*, 158: 1785 (1983); Altieri, et al., *J. Cell Biol.*, 107: 1893 (1988); Wright, S. D., et al., *Proc. Natl. Acad. Sci. USA*, 85: 7734 (1988); Altieri, et al., *J. Biol. Chem.*, 263: 7007 (1988)), EPR-1 binds the activated serine protease Xa (Altieri, et al. *J. Biol. Chem.* 264: 2969 (1989)).

Anti-CD11b/CD18 mAb do not inhibit EPR-1 receptor function and the reverse also applies for EPR-1 mAb on CD11b/Cd18 ligand recognition. Similarly, soluble CD11b/CD18 ligands such as fibrinogen (Altieri, et al., *J. Cell Biol.*, 107: 1893 (1988); Wright, S. D., et al., *Proc. Natl. Acad. Sci. USA*, 85: 7734 (1988)), and factor X (Altieri, et al., *J. Biol. Chem.*, 263: 7007 (1988)), do not compete or inhibit EPR-1 receptor recognition of Xa.

C. Dynamic Regulated Expression of EPR-1 on PBL.

Additional studies were designed to explore the possibility of a dynamic modulation of EPR-1 expression under conditions of antigen-specific or mitogen-driven T cell activation. Freshly isolated PBMC were set up in unidirectional mixed lymphocyte culture (MLC) against irradiated allogeneic B cells, i.e., Raji (MHC class I and II driven) or Daudi (MHC class II driven). After 7 days culture, responder T cells were harvested, washed, and phenotypically characterized by FMF using mAb 7G12, 9D4, and 12H1.

In another series of studies, PBMC were separately cultivated for 7 days in the presence of 1 µg/ml of the polyclonal activators (PHA) or Con A then subjected to FMF analysis. Both allogeneic expansion of normal PBMC or lectin activation resulted in a consistent three- to four-fold increase in EPR-1$^+$ T cells, as recognized by mAb 12H1 (not shown).

To exclude the possibility that the observed expansion of 12H1$^+$ cells resulted from a selective redistribution of T cell subsets occurring upon activation, Con A-stimulated PBMC were sequentially analyzed by FMF after various time intervals of culture. Con A-mediated quantitative expansion of the EPR-1$^+$ subset occurred in cells with forward light scatter characteristic of proliferating, activated blasts. The number of these cells increased approximately four-fold between day 6 and 7 of culture and when these cells were phenotypically characterized by two-color FMF they were CD3$^+$, CD4$^-$, CD8$^+$, CD2$^+$.

Additional studies were carried out to investigate the effects of long term alloreactive stimulation on EPR-1 expression. Unidirectional MLC against irradiated Daudi cells was maintained in continuous culture with weekly transfers in the presence of 10% T-cell growth factor (TCGF). At various time intervals, aliquots of responder T cells were harvested, recovered by centrifugation over FICOLL-HYPAQUE, and finally analyzed for EPR-1 marker expression by FMF using mAb 12H1 or the polyclonal antiserum B78.9 (data not shown). The number of EPR-1$^+$ cells detected by mAb 12H1 increased approximately ninefold during antigen-mediated activation after one month of culture. Similar results were also obtained using the polyclonal antiserum B78.9, which shows a larger reactivity consistent with the greater number of EPR-1 epitopes detected by this reagent.

To distinguish between selective expansion of EPR-1$^+$ cells or de novo expression of this marker resulting from polyclonal or antigen stimulation, an additional set of studies was carried out. Suspensions of freshly isolated PBL were preparatively fractionated in EPR-1$^+$ and EPR-1$^-$ subsets by FMF sorting with mAb 12H1. These resulting populations were then separately cultivated for 10 days with 1 µg/ml Con A, 5 µg/ml PHA, or stimulated in mixed lymphocyte response with irradiated Daudi in the presence of 10% TCGF before FMF analysis of EPR-1 expression. The results of these experiments are shown in Table 3, hereinafter. Both polyclonal- or antigen-stimulation of the negatively selected EPR-1$^-$ subset was associated with de novo expression of EPR-1 as detected by binding of mAb 12H1.

TABLE 3

De novo EPR-1 expression on negatively selected EPR-1$^-$ subset activated after short term culture[a]

| | EPR-1$^-$ Subset | | EPR-1$^+$ Subset | |
|---|---|---|---|---|
| Stimulation | Positive Cells (%) | Fluorescence (U) | Positive Cells (%) | Fluorescence (U) |
| — | 0.2 | 5.5 | 77.5 | 102.1 |
| PHA | 6.8 | 78.3 | ND | ND |
| Con A | 47.2 | 218.5 | ND | ND |
| Daudi MLC | 45 | 82 | 91.8 | 83.1 |

[a]Freshly isolated PBL were fractionated in EPR-1$^-$ and EPR-1$^+$ subsets by FMF using mAb 12H1. The resulting populations were cultivated in the presence of 1 µg/ml Con A, 5 µg/ml PHA or stimulated in allogeneic MHC with Daudi cells for 10 days before FMF analysis with anti-EPR-1 mAb 12H1. U = arbitrary units.

D. EPR-1 Expressed on T Cells is a Functionally Active Protease Receptor

To further substantiate the expression of EPR-1 on discrete lymphoid populations, a number of transformed in vitro T cell lines were screened by FMF using the panel of mAb described above. Of the various T cell lines assayed only a subpopulation of HuT 78 cells was reactive with mAb 7G12 (not shown). These cells were isolated to >90% purity by fluorescence sorting using the polyclonal antiserum B78.9 to yield the subpopulation HuT 78*, which was then cloned by limiting dilution. Three clones were established, subcloned, phenotypically characterized by FMF as OKT3$^+$, OKT4$^+$, OKT8$^-$, 12H1$^+$, B78.9$^+$, and one of them was selected for further investigations.

When suspensions of HuT 78* were equilibrated with increasing concentrations of $^{125}$I-Xa in the presence of 2.5 mM CaCl$_2$, these cells bound the offered ligand in a specific and concentration-dependent reaction, approaching steady saturation at 30 to 36 nM of added $^{125}$I-Xa (Table 4). Quantitatively similar to the results previously obtained with THP-1 cells (Altieri, et al., *J. Biol. Chem.* 264: 2969 (1989)), this reaction was regulated by an apparent K$_d$ on the order of 10 to 20 nM, and was saturated when 194,000±26,000 molecules of $^{125}$I-Xa were specifically associated with the surface of each HuT 78* cell. Finally, preincubation of HuT 78* cells with saturating amounts of mAb 9D4 inhibited specific binding of $^{125}$I-Xa to these cells.

TABLE 4

| $^{125}$I-Factor Xa added (nM)[a] | $^{125}$I-Xa bound (molecules/cell X10$^{-3}$) | |
|---|---|---|
| | mAb 9D4 | No mAb |
| 1.5 | 1 | 6 |
| 5 | 8 | 26 |
| 8 | 20 | 50 |
| 18 | 33 | 140 |
| 27 | 58 | 170 |
| 36 | 76 | 200 |

[a]$^{125}$I-factor Xa binding to HuT 78* cells.

HuT 78* cells reacting with the rabbit polyclonal antiserum B78.9 were isolated to 94.2% purity by fluorescence sorting and cloned by limiting dilution. Three clones were established, phenotypically characterized and one (HuT 78*–3) selected for further investigations. Suspensions of HuT 78*–3 cells at 1×10$^7$/ml were separately incubated with control antibody or with 50 μg/ml of the anti-EPR-1 mAb 9D4 for 30 minutes at room temperature, before the addition of increasing concentrations of $^{125}$I-factor Xa (0.45 to 36 nM) and 2.5 mM CaCl$_2$ for additional 20 min at room temperature. The reaction was terminated by centrifugation through mixture of silicone oils and $^{125}$I-Xa specific binding to HuT 78* cells was calculated in the presence or absence of anti-EPR-1 mAb 9D4.

E. Discussion

The reactivity of a panel of mAbs with a cell surface protease receptor expressed on some leukocytes has now been characterized. In previous studies, it was shown that a mAb originally raised against the plasma coagulation protein V (7G12) bound in specific and saturable reaction to the monocytic-myeloid cell lines THP-1, U937, and HL-60 (Altieri, et al., *J. Biol. Chem.* 264: 2969 (1989)). Further, by analogy with the known acceptor/cofactor function of the plasma protein Va (Nesheim, M. E., et al., *J. Biol. Chem.*, 254: 10952 (1979)), the molecule recognized by mAb 7G12 on these cells appeared to be implicated in a specific receptor function for the serine protease Xa.

A panel of anti-V mAbs has now been raised. The hybridomas secreting those mAbs were selected by FMF analysis of THP-1 cells, and the mAbs were used as probes to search for expression of the V cell surface cross-reacting molecule on peripheral blood cells.

The first conclusion that can be drawn from these studies is that the molecule recognized by these mAbs, operatively defined as EPR-1, is not inappropriately expressed only by transformed cell lines in culture. Rather, it has a broad cellular distribution and a remarkable association with cells of myeloid and lymphoid lineage. Although with considerable heterogeneity among the various populations examined, these mAbs defining EPR-1 were found to be reactive with peripheral blood monocytes, PMN, and CD3$^-$CD16$^+$CD56$^+$ NK cells.

Interestingly, a small fraction of circulating T cells was also identified as EPR-1$^+$. Phenotypic characterization of this subset by FMF suggested that the expression of EPR-1 does not appear to be segregated into a unique subpopulation defined by currently known markers of T cells. Although the majority of EPR-1$^+$ T cells isolated from various donors was also CD8$^+$ or α/βTCR$^+$, cells coexpressing CD4 or γ/δTCR were identified as well. In agreement with this finding, FMF analysis of various transformed T cell lines in vitro, revealed expression of EPR-1 markers on MOLT 13 cells that were further phenotypically established as CD4$^+$ and TCR γ/δ$^+$, respectively, in agreement with previous observations (Lefranc, M. P., et al., *Nature*, 316: 464 (1985); Brenner, M. B., et al., *Nature*, 325: 689 (1987)).

Within the CD8$^+$ fraction of normal PBL, EPR-1 expression was consistently associated with coexpression of CD11b(Leu 15) and CD57(Leu 7), as identified by mAbs OKM1 and HNK-1. In earlier studies, this pattern of markers has been associated with suppressor function (Clement, L. T., et al., *J. Immunol.*, 133: 2461 (1984); Fox, E. J., et al., *J. Exp. Med.*, 166: 404 (1987); Takeuchi, T., et al., *Cell. Immunol.*, 111: 398 (1988)) and LAK activity (Dianzani, et al., *Eur. J. Immunol.*, 19: 1037 (1989)). However, at variance with the previously reported poor proliferative response of this T cell subset (Fox, E. J., et al., *J. Exp. Med.*, 166: 404 (1987)), EPR-1 expression is observed as strongly increased by both mitogen and antigen stimulation.

This finding appeared to be particularly emphasized in studies using long term cultures of alloreactive-stimulated T cells, where the anti-EPR-1 rabbit polyclonal antibody B78.9 reacted with virtually all responder cells after one month culture. Similarly, de novo EPR-1 expression was also observed after short term polyclonal or antigen stimulation of preparatively sorted EPR-1$^-$ populations. Although these data would appear to be compatible with the hypothesis that EPR-1 is a true T cell activation responsive molecule, further investigations at the single clonal cell level are necessary to conclusively address this possibility. Finally, in agreement with the expression of both CD4 or CD8, no preferential expansion of EPR-1$^+$ cells was observed by either class I or class II MHC allogeneic stimulation.

Although the cellular distribution of EPR-1 closely resembles that of the leukocyte integrin CD11b/CD18 (Sanchez Madrid, F., et al., *J. Exp. Med.*, 158: 1785 (1983)), structure/function analyses revealed by immunoprecipitation studies and $^{125}$I-labelled ligand binding assays clearly demonstrate that these are two different molecules implicated in distinct and different receptor recognition functions (Altieri, et al., *J. Biol. Chem.* 264: 2969 (1989); Sanchez Madrid, F., et al., *J. Exp. Med.* 158: 1785 (1983); Altieri, et al., *J. Cell Biol.* 107: 1893 (1988); Wright, S. D., et al., *Proc. Natl. Acad. Sci. USA* 85: 7734 (1988); Altieri, et al., *J. Biol. Chem.* 263: 7007 (1988)).

This study has not been designed to address the reciprocal relationship between cellular EPR-1 and the plasma protein V, that originally served as an immunogen to raise the anti-EPR-1 mAb used. However, it is important to note that the anti-EPR-1 mAb panel described (panel I), constitutes only a minor fraction of the anti-V hybridomas elicited by immunization with factor V. In fact, a second panel of anti-V mAb raised and established under identical protocols and selected for production of mAb immunoreactive with factor V did not exhibit cross-reactivity with THP-1 cells. Furthermore, the size (M$_r$ 62–74 kDa) and structural organization of EPR-1 resolved in immunoprecipitation studies exhibits remarkable size similarity to the light chain of the plasma protein factor Va (Nesheim, M. E., et al., *J. Biol. Chem.*, 254: 10952 (1979)). On the basis of these considerations, it is thought that EPR-1 represents a cell surface molecule homologous to the plasma coagulation protein V maintaining some conserved immunoreactive epitopes functionally associated with ligand recognition.

Whether the expression of EPR-1 on various leukocyte populations implies its involvement in specific immune effector functions is presently not known. However, the observation that NK cells and CD8$^+$ T cells express a high affinity serine protease receptor is provocative in view of the identification of a family of closely related serine proteases (granzymes) contained in the granules of human and mouse NK and CTL clones (Masson, D., et al., *Cell*, 49: 679 (1987)). These enzymes share significant homology with a number of serine proteases, particularly with the coagulation proteases factor IXa, Xa, and plasmin (Jenne, D., et al., *Proc. Natl. Acad. Sci. USA*, 85: 4814 (1988); Gershenfeld, H. K., et al., *Science*, 232: 854 (1986); Jenne, D., et al., *J. Immunol.*, 140: 318 (1988); Lobe, C. G., et al., *Science*, 232: 858 (1986); Gershenfeld, H. K., et al., *Proc. Natl. Acad. Sci. USA*, 85: 1184 (1988)). It is also noteworthy that dynamic modulation of gene expression and secretion of the granzymes is increased by the same stimuli that are associated with increased EPR-1 expression in vitro, i.e., long term response to antigen and IL-2 (Manyak, C. L., et al., *J. Immunol.*, 142: 3707 (1989); Masson, D., et al., *EMBO J.*, 4: 2533 (1985)). Although the role of the cellular granzymes in NK or CTL killing remains to be elucidated (Dennert, G., et al., *Proc. Natl. Acad. Sci. USA*, 84: 5004 (1987)), a putative role for serine proteases in the lytic process has been suggested by experiments using serine proteases inhibitors (Redelman, D., et al., *J. Immunol.*, 124: 870 (1980); Chang, T. W., et al., *J. Immunol.*, 124: 1028 (1980); Suffys, P., et al., *Eur. J. Biochem.*, 178: 257 (1988); Scuderi, P., *J. Immunol.*, 143: 168 (1989)).

By analogy with the general concept of receptor-mediated amplification of proteolytic activities (Miles, L. A., et al., *Fibrinolysis*, 2: 61 (1988); Morrissey, et al., *Cell*, 50: 129 (1987); Nesheim, M. E., et al., *J. Biol. Chem.*, 254: 10952 (1979)), it is thought that locally released granzymes might interact with a membrane component on the effector cell to deliver optimal catalytic efficiency, protected from neutralization by circulating protease inhibitors. In this context, EPR-1 would embody the requirements for a surface receptor expressed by immune effector cells, displaying ligand recognition for a prototypical and highly conserved serine protease such as factor Xa, and dynamically up-regulated by antigenic stimulation.

By using an uncommon strategy for mAb selection, a new leukocyte marker, a serine protease receptor, and an apparent cell-surface homologue of the plasma coagulation protein V have been identified. Because of its remarkable distribution on immune effector cells, the name "EPR-1" is proposed to tentatively identify this molecule. Although the role of EPR-1 in the mechanism of cell-mediated formation of fibrin is highlighted by its recognition for Xa (Nesheim, M. E., et al., *J. Biol. Chem.*, 254: 10952 (1979)), it is thought that the wide spectrum of biologic activities mediated by serine proteases implicates the involvement of EPR-1 in the recognition of additional ligands and in cell-mediated functions.

Example 12

The Roles of EPR-1 and Factor Xa In Protease-Dependent T Cell Activation

A. Materials and Methods

Cells and cell cultures were prepared as follows. Peripheral blood mononuclear cells (PBMC) were isolated from heparinized blood drawn from normal healthy volunteers after informed consent. Platelet-rich plasma was removed after centrifugation of the blood at 800×g for 12 minutes at 22° C. PBMC were separated by differential centrifugation on FICOLL-HYPAQUE gradient (Sigma Chemical Co., St. Louis, Mo.) (density=1.077 g/ml) at 400×g for 18 minutes at 22° C., washed in PBS plus 5 mM EDTA, pH 7.2, and resuspended in complete RPMI 1640 tissue culture medium (M. A. Whittaker, Walkersville, Md.), containing 10% heat-inactivated fetal calf serum (FCS, Whittaker), 2 mM L-glutamine (Irvine Scientific, Calabasas, Calif.), and 25 mM Hepes (Calbiochem Boehring Diagnostic, La Jolla, Calif.). T lymphocytes (>95% OKT3$^+$) were fractionated from PBMC by two sequential cycles of plastic adherence for 1 hour at 37° C., followed by incubation of the non-adherent population with the lysosomotropic compound leucine methyl esther (Leu-Ome, Sigma) for 45 minutes at 22° C. (Thiele, et al., *J. Immunol.* 131: 2282 (1983)), and filtration of the viable population through a nylon wool column for 1 hour at 37° C. with recovery of non adherent cells.

EPR-1 expression on the various cells used in this study was determined by flow cytometry, as described previously (Altieri, et al., Id. (1990); also see Example 3 above).

The experimental procedures used for the isolation and purification of blood protease factor Xa were as described in Altieri, et al., *J. Biol. Chem.* 264, 2969 (1989)). Antithrombin III (ATIII, Sigma, St. Louis, Mo.) was used as a control irrelevant protein in lymphocyte proliferation experiments. Anti-CD3 mAb was OKT3; mAbs to α/β T cell receptor (WT-31), IL-2 receptor (1HT44H3), and to CD56 (Leu19) were purchased from Becton Dickinson (Mountain View, Calif.). Anti-γ/ΔT cell receptor mAb Δ-1 was generously provided by Dr. D. P. Dialynas (The Scripps Research Institute, La Jolla, Calif.). Anti-CD20 mAb B-1 was purchased from AMAC Inc. (Westbrook, Me.). Isotype-matched controls used in proliferation experiments were anti-CD57 mAb HNK-1 (IgM) (Abu, et al., *J. Immunol.* 129: 1758 (1982)), and two anti-tissue factor mAbs 9C6 and 5G9, generously provided by Dr. W. Ruf (The Scripps Research Institute, La Jolla, Calif.). (Hybridoma 5G9 is described in U.S. Pat. No. 5,110,730 to Edgington, et al., the relevant disclosures of which are incorporated by reference herein.) Non-binding mAb HB3 of unknown specificity was used as a control in flow cytometry experiments.

Cell proliferation experiments were conducted essentially as described previously (Example 1). Suspensions of PBMC in complete RPMI 1640 medium were seeded in triplicates at 3×10$^5$/well in 96-well tissue culture microtiter plates (Costar Corp., Cambridge, Mass.) and incubated with increasing concentrations factor Xa (1.5–300 nM), or control protein ATIII, in the presence or in the absence of non-mitogenic doses of phorbol ester (PMA, Sigma, 1 ng/ml). After a 3-day culture at 37° C., cells were pulsed with 1 μCi/well $^3$HTdR for 12 hours at 37° C., harvested, and radioactivity incorporated under the various conditions was determined in a scintillation β counter.

In another series of experiments, suspensions of PBMC (3×10$^5$/well) or purified T cells (1.5×10$^5$/well) were stimulated with 1 μg/ml soluble anti-CD3 mAb OKT3 (Geppert, et al., *J. Immunol.* 138: 1660 (1987)), and simultaneously mixed with anti-EPR-1 mAbs 12H1 (1:500 dilution ascites fluid) or 13E5 (25 μg/ml), or isotype-matched control mAbs HNK-1 or 5G9 for 3 days at 37° C. Cell proliferation under the various conditions tested was assessed by $^3$HTdR incorporation as described above. Time-course studies of EPR-1-stimulated lymphocyte proliferation were carried out by cultivating a high responder cell concentration of 1×10$^6$ PBMC/well in the presence or in the absence of control mAb 9C6 (50 μg/ml), anti-CD3 mAb OKT3 (1 μg/ml), or anti-EPR-1 mAb 13E5 (50 μg/ml) for various time intervals at 37° C. At the end of each 24 hour culture, wells were pulsed with 1 μCi/well $^3$HTdR, and radioactivity incorporated under the various conditions was determined as described above. In another series of experiments, purified T cells ($1.5\times10^5$/well) or PBMC ($3\times10^5$/well) were cultivated with increasing concentrations PMA (0.01–2.5 ng/ml), or increasing doses IL-2 (0.2–16.7 U/ml) in the presence or in the absence of 25 μg/ml anti-EPR-1 mAb 13E5 for 3 days at 37° C., before quantitation of cell proliferation by $^3$HTdR incorporation.

Phenotypic characterization of the lymphocyte population expanded by EPR-1 engagement was carried out by flow cytometry. PBMC at $1\times10^6$/ml in complete RPMI 1640 medium were cultivated in 24-well tissue culture plates (Costar) in the presence of 50 μg/ml anti-EPR-1 mAb 13E5 or control mAb 9C6 for 7 days at 37° C. Cells were harvested, washed in PBS, pH 7.2, presaturated with 20% normal human serum for 30 minutes at 4° C. to prevent Fc-mediated mAb binding, and incubated with various mAbs to lineage-specific leukocyte surface antigens for 30 minutes at 4° C. After washes, binding of the primary mAbs was revealed by addition of a 1:20 dilution of FITC-conjugated goat anti-mouse F(ab')$_2$ fragments (Tago Inc., Burlingame, Calif.) for additional 30 minutes at 4° C. Cells were washed and immediately analyzed on a Becton Dickinson FacScan. Background fluorescence was assessed in the presence of non-binding mAb HB3, under the same experimental conditions. Actively proliferating blast cells were fractionated on the basis of cell-cycle dependent variations in cell volume as determined by size/forward scatter parameters (Darzynnkiewicz, et al., *PNAS USA* 77: 6696 (1980)).

Early events of intracellular $Ca^{2+}$ signalling after EPR-1 occupancy were characterized in real-time fluorescence measurements at the single cell level (Altieri, et al., *Biochem. J.* 288: 465 (1992)). Freshly isolated T lymphocytes were attached onto Cell-Tak-(Biopolymers, Farmington, Conn.)-coated optical grade glass coverslips (22 mm$^2$ diameter and <0.16 μm thickness), and loaded intracellularly with 1 μM of the $Ca^{2+}$-sensitive fluorescent dye Indo-1/AM (Grynkiewicz, et al., *J. Biol. Chem.* 260: 3440 (1985)) (Calbiochem) in 145 mM NaCl, 5 mM KCl, 1 mM Na$_2$HPO$_4$, 2.5 mM CaCl$_2$, 10 mM glucose, 25 mM HEPES, 0.5 mM MgSO$_4$ for 45 minutes at 37° C. Cells were gently washed in the same loading buffer, and analyzed in real time fluorescence measurements in digitalized imaging using the interactive laser cytometer ACAS 470, as described (Altieri, et al., Id. (1992)). Briefly, 50 μg/ml concentrations of control mAb 9C6, anti-EPR-1 mAb 13E5, or anti-CD3 mAb OKT3 were added after the first scan (25 seconds) of a group of 10–25 adherent T lymphocytes during continuous transectional fluorescent analysis. After 125 seconds from the addition of the primary mAb, 50 μg/ml aliquots of goat anti-mouse F(ab')$_2$ fragments were added as a cross-linking reagent, and fluorescence changes in the target cells were monitored continuously during a 3-minute interval. Changes in cytosolic free $[Ca^{2+}]_i$ under the various conditions tested are expressed as ratio of Detector 1 (free Indo-1, 485 nm wavelength)/Detector 2 (Indo-1:$Ca^{2+}$ complex, 405 nm wavelength).

B. Results

1. Ligation of EPR-1 Stimulates Lymphocyte Proliferation

Initial experiments analyzed the effect of increasing concentrations of the natural EPR-1 ligand, factor Xa, on PBMC proliferation. As shown in FIG. 16, factor Xa plus non-mitogenic doses PMA stimulated DNA synthesis and $^3$HTdR incorporation in unfractionated PBMC in a dose-dependent fashion. Consistent with the equilibrium binding parameters of $^{125}$I-factor Xa association with EPR-1, maximal proliferative response was observed for saturating factor Xa concentrations of 15–75 nM (FIG. 16). In contrast, comparable concentrations of factor Xa alone, or of control protein ATIII plus PMA, did not affect PBMC proliferation, under the same experimental conditions (FIG. 16).

To substantiate the participation of EPR-1 in factor Xa-mediated PBMC proliferation, the anti-EPR-1 mabs 12H1 or 13E5 characterized in previous studies (Altieri, et al., Id. (1989) and (1990)), were used as "surrogate" ligands to co-stimulate lymphocyte proliferation. PBMC at $3\times10^5$/well were stimulated with 1 μg/ml soluble anti-CD3 mAb OKT3 in the presence or in the absence of anti-EPR-1 mAb 12H1 or control mAb HNK-1 (1:500 ascites dilution). Cell proliferation was assessed after a 3-day culture at 37° C. as described in FIG. 16.

The experiment was then repeated, except that suspensions of purified T lymphocytes ($1.5\times10^5$/well, >95% OKT3$^+$) were incubated with soluble anti-CD3 mAb OKT3, in the presence of anti-EPR-1 mAb 13E5 or control mAb 5G9. Cell proliferation was determined by $^3$HTdR incorporation after a 3-day culture at 37° C. (data not shown). Finally, T lymphocytes ($1.5\times10^5$/well) were cultivated for 3 days at 37° C. with increasing concentrations of PMA (0.01–2.5 ng/ml) in the presence or in the absence of 50 μg/ml anti-EPR-1 mAb 13E5 before quantitation of cell proliferation (data not shown).

While neither 12H1 or 13E5 alone affected PBMC proliferation when $3\times10^5$ responder cells/well were used (see below), mAbs 12H1 or 13E5 increased by ~2-fold PBMC (data not shown) or purified T cell proliferation stimulated by soluble anti-CD3 mAb OKT3 (not shown). A similar 2-fold increase in purified T cell proliferation was also observed after receptor cross-linking with co-immobilized mAbs OKT3 and 13E5 (not shown), although the magnitude of this proliferative response was much larger than that observed with soluble mAbs, in agreement with previous observations (Geppert, et al., Id. (1987)). Anti-EPR-1 mAb 12H1 also augmented by ~2-fold polyclonal PBMC proliferation stimulated by lectins ConA (1 μg/ml) or PHA (4 μg/ml) during a 3-day $^3$HTdR incorporation assay (not shown). Finally, consistent with the data presented in FIG. 16, anti-EPR-1 mAb 13E5 stimulated purified T cell proliferation in combination with non-mitogenic, increasing concentrations PMA (data not shown).

As shown earlier, circulating EPR-1$^+$ cells comprise only a small subset of 5–10% of resting T cells (Altieri, et al., Id. (1990)). Therefore, it was of interest to investigate the relationship between the kinetic/magnitude of EPR-1-dependent lymphocyte stimulation and the number of potential EPR-1$^+$ responder cells in the incubation reaction.

For these experiments, a high responder cell concentration of $1\times10^6$ PBMC/well (in triplicate) was incubated with saturating doses anti-EPR-1 mAb 13E5, anti-CD3 mAb OKT3, or control mAb 9C6 for various time intervals at 37° C. At the end of each 24 hour culture, cell proliferation was determined by $^3$HTdR incorporation as described in FIG. 16. At variance with the requirements for accessory co-stimulatory signals implicated in EPR-1-dependent proliferation at low responder cell concentrations (FIG. 16), anti-EPR-1 mAb 13E5 produced a strong primary proliferative response under these experimental conditions, in the absence of additional stimulatory signals. Maximal expansion of the EPR-1-sensitive cellular subset(s) stimulated by mAb 13E5 occurred with a more delayed kinetic as compared with the OKT3-mediated response, and peaked after a 4–6 day culture at 37° C. (data not shown).

2. Mechanism of EPR-1-mediated Lymphocyte Co-stimulation

The role of IL-2, and IL-2 receptor, in EPR-1 dependent lymphocyte stimulation was investigated using two independent experimental approaches. First, the effect of IL-2 on EPR-1 mediated lymphocyte proliferation was determined as follows. PBMC at $3\times10^5$/well were cultivated for 3 days at 37° C. with the indicated concentrations IL-2 (0.2–16 U/ml), in the presence or in the absence of 50 μg/ml anti-EPR-1 mAb 13E5. Control cultures were incubated with antithrombin III (ATIII) plus PMA under the same experimental conditions. Cell proliferation was quantitated by $^3$HTdR incorporation. Data±S.E.M. were representative of two independent experiments (data not shown). Addition of anti-EPR-1 mAb 13E5 to low responder cell concentrations stimulated a 3- to 4-fold increase in lymphocyte proliferation in the presence of very low, non mitogenic doses IL-2 (0.2–2 U/ml), as compared with control cultures incubated with mAb 9C6 under the same experimental conditions (data not shown).

In a second series of experiments, low responder cell concentrations were cultivated with anti-EPR-1 mAb 13E5 or control mAb 9C6 for 24 hours at 37° C. (priming), and subsequently mixed with increasing doses IL-2 (0.2–16 U/ml) for 3 days at 37° C. PBMC at $3\times10^5$/well were cultivated in the presence of 50 μg/ml control mAb 9C6 or anti-EPR-1 mAb 13E5 for 24 hours at 37° C. At the end of the incubation, cells were mixed with increasing doses of IL-2 (0.2–16 U/ml) for an additional 3-day culture at 37° C., before quantitation of $^3$HTdR incorporation (data not shown). Next, PBMC were initially cultivated with IL-2 (2 U/ml) for 24 hours at 37° C., and subsequently mixed with 50 μg/ml control mAb 9C6 or anti-EPR-1 mAb 13E5 and increasing doses IL-2 (0.2–16 U/ml) for 3 days at 37° C. Data±S.E.M. were representative of two independent experiments (not shown). EPR-1 priming with mAb 13E5 resulted in 5 to 8-fold increased PBMC proliferation in response to very low doses IL-2 (0.2 U/ml), as compared with cultures primed with control mAb 9C6 under the same experimental conditions. As determined by flow cytometry, EPR-1-primed cells under these experimental conditions strongly reacted with anti-IL-2 receptor mAb 1HT44H3 (see below).

3. Phenotypical Characterization of EPR-1 Responder Cells

For these experiments, actively proliferating blast cells expanded after EPR-1 engagement were identified by flow cytometry on the basis of cell-cycle-dependent variations in cell volume (Darzynnkiewicz, et al., Id. (1980)). The results of these experiments indicated that, in agreement with $^3$HTdR incorporation experiments, ligation of EPR-1 with mAb 13E5 stimulated the proliferation of a small and discrete cellular subset (16–20%), with size/forward scatter parameters of actively proliferating blasts (data not shown). In contrast, no significant increase in the number of activated cells was observed in control cultures incubated with mAb 9C6 under the same experimental conditions.

Consistent with the phenotypically heterogeneous distribution of EPR-1 on resting PBMC, EPR-1-responder cells comprised lymphocytes of both T and B lineages (WT31$^+$ and B1$^+$, respectively), the former including both α/β$^+$ and γ/Δ$^+$ cells (WT31$^+$ and Δ1$^+$, respectively), CD4$^+$, CD8$^+$, and CD11b$^+$ cells (not shown). In contrast, a considerably smaller increase was observed in the Leu19$^+$, NK fraction of EPR-1-stimulated cells. Finally, in agreement with the postulated IL-2-dependent mechanism of EPR-1-mediated lymphocyte proliferation, EPR-1 responder cells strongly reacted with anti-IL-2 receptor mAb 1HT44H3, as compared with control cultures incubated with mAb 9C6 under the same experimental conditions.

4. Intracellular Signalling Initiated by EPR-1 Engagement

Additional experiments analyzed whether or not occupancy of EPR-1 with the activating mAb 13E5 was associated with early events of intracellular signal transduction in single adherent lymphocytes (Gardner, P., Cell 59: 15 (1989)). T cells loaded intracellularly with the $Ca^{2+}$-sensitive fluorescent dye Indo-1 immediately and homogeneously responded to 7 μM ionomycin with a large and sustained increase in cytosolic free $[Ca^{2+}]_i$ (not shown). Similarly, CD3 cross-linking with mAb OKT3 also produced a $Ca^{2+}$ response in most cells analyzed, in a reaction that temporally coincided with the addition of the goat anti-mouse F(ab')$_2$ fragments, in agreement with previous observations.

In contrast, control mAb 9C6 plus goat anti-mouse cross-linking reagent did not elicit any $Ca^{2+}$ response in target cells. Under these experimental conditions, cross-linking of EPR-1 with mAb 13E5 plus goat anti-mouse F(ab')$_2$ fragments resulted in a temporally and quantitatively heterogeneous $Ca^{2+}$ response that was partially reduced but not abolished in the absence of extracellular $Ca^{2+}$ ions (3 mM EGTA-containing buffer, not shown). As dissected at the single cell level, this $Ca^{2+}$ response was observed in ~20% of the analyzed population, consistent with the expression of EPR-1 on only a small subset of resting T cells (see above).

C. Discussion

This study shows that a novel protease receptor denominated Effector cell Protease Receptor-1 (EPR-1), contributes to T cell activation. In addition to their role in clotting/fibrinolytic mechanisms, blood proteases trigger specialized cellular responses. These include cell motility and aggregation (Ossowski, Cell 52: 321 (1988); Shuman, Ann. N.Y. Acad. Sci. 485: 349 (1986)), transcription of early activation-dependent genes (Daniel, et al., J. Biol. Chem. 261: 9579 (1986)), expression of inducible cell adhesion molecules (Zimmerman, et al., J. Clin. Invest. 76: 2235 (1985)), intracellular signalling pathways of cell activation (Vu, et al., Cell 64: 1057 (1991); Paris, et al., J. Biol. Chem. 259: 10989 (1984); Golden, et al., J. Cell Biol. 111: 3117 (1990)), and DNA synthesis and proliferation of both normal and transformed cells (Glenn, et al., Nature 278: 711 (1979); Kirchheimer, et al., PNAS USA 86: 5424 (1989); Ossowski, et al., J. Biol. Chem. 249: 4312 (1974); Sullivan, et al., Cell, 45: 905 (1986)). Through the recognition and signalling properties of complementary cell surface receptors, thrombin (Vu, et al., Id. (1991)), urokinase (Appella, et al., Id. (1987)), coagulation factors XII/XIIa (Schmeidler-Shapiro, et al., PNAS USA 88: 4382 (19920), and factors X/Xa (Gasic, et al., Id. (1992)), all stimulate proliferation of various mesenchymal cells, in a mechanism potentially contributing to the early molecular events of vascular injury and atherosclerosis (Ross, Nature 362: 801 (1993)).

Earlier characterized for its recognition of the blood coagulation protease factor Xa on various leukocyte subsets, EPR-1 is a typical lymphocyte activation-dependent antigen, that participates in the mechanism of thrombin formation at the cell surface. Here, we show that physiologic concentrations of the natural EPR-1 ligand, factor Xa, stimulate lymphocyte proliferation in the presence of accessory signals, i.e. PMA. The ability of anti-EPR-1 mAbs 12H1 and 13E5 to recapitulate this mitogenic response further substantiated the role of EPR-1 as a factor Xa receptor implicated in lymphocyte stimulation, and concurred to rule out the effect of potential mitogenic contaminants in the factor Xa preparation. Under these experimental conditions, mAb engagement of EPR-1 increased cytosolic free $[Ca^{2+}]_i$ in single adherent T cells, stimulated T cell proliferation in the presence of PMA, and augmented by ~2 fold clonotypic T cell proliferation initiated by mAb OKT3.

As shown in previous studies, EPR-1+ cells in the circulation comprise a small subset of 5–10% of unfractionated lymphocytes (Altieri, et al., Id. (1990)). Consistent with this relatively low cellular representation, the mechanism of EPR-1-dependent lymphocyte proliferation is sharply dependent on the threshold number of EPR-1+ responder cells present in the incubation reaction. At low responder cell concentrations, ligation of EPR-1 transduces an accessory co-stimulatory signal for T cell activation, while EPR-1 engagement at higher responder cell concentrations is per se sufficient to initiate lymphocyte proliferation, in the absence of additional signals. In this context, ligation of EPR-1 increases the mitogenic responsiveness of target cells to very low doses IL-2 (0.2 U/ml), via early surface expression of IL-2 receptors, and expands a discrete (16–20%) and heterogeneous population composed of both B and T lymphocytes, with a more delayed kinetic as compared with the OKT3-mediated response.

Further studies using mutagenized factor Xa are contemplated to further elucidate the role of the protease catalytic active site in this proliferative response. However, the ability of anti-EPR-1 mAbs 12H1 or 13E5 to stimulate T cell activation in the absence of catalytic activity, suggests that the molecular prerequisite of this proliferative response might reside in physical receptor occupancy and ligand-induced intracellular signalling, rather than local receptor proteolysis (Vu, et al., Id. (1991)).

There are profound pathophysiologic implications for the mitogenic pathway described here. First, receptor-mediated assembly of proteases on discrete lymphocyte subsets might provide a novel regulatory mechanism of lymphocyte stimulation/co-stimulation. Consistent with the current models of T cell activation (Janeway, et al., *Curr. Opin. Immunol.* 5: 313 (1993); Jenkins, et al., *Curr. Opin. Immunol.* 5: 361 (1993)), co-stimulatory signals play a crucial role in maintaining antigen-specific mechanisms of the immune response in vivo (Schwartz, *Cell* 71: 1065 (1992)). In this context, lymphocyte co-stimulation functions as a redundant process primarily coordinated by the CD28:B7/B7-2 receptor-counterreceptor pair (Schwartz, et al., Id. (1992); Freeman, et al., *Science* 262: 909 (1993)), but also contributed by a variety of additional signal transducing molecules, that include adhesion receptors of the integrin- (van Noesel, et al., *Nature* 333: 850 (1988), and Ig-gene superfamilies (Cerdan, et al., *Cell. Immunol.* 123: 4579 (1986)), membrane ecto-5'-nucleotidases (Thompson, et al., *J. Immunol.* 142: 1518 (1989)), and lymphocyte homing receptors (Rothman, et al., *J. Immunol.* 147: 2493 (1991)). Based on the data presented here, EPR-1 might provide novel aspects of lymphocyte stimulation/co-stimulation (Schwartz, Id. (1992)).

Proteases are ubiquitously generated in vivo during disparate immune-inflammatory responses, invariably associated with activation of coagulation and fibrinolytic mechanisms (Furie, et al., Id. (1988). Binding of the locally generated factor Xa to EPR-1+ cells might generate an independent "accessory signal" to up-regulate IL-2 receptor expression and increase lymphocyte proliferation in response to very low doses of IL-2, released in the cellular microenvironment of the inflammatory lesion. Along the same line, this mechanism might also contribute to the early molecular events of vascular injury and atherosclerosis, characterized by activation of coagulation and proliferation and intraintimal accumulation of various leukocyte subsets (Ross, Id. (1993); Jonasson, et al., *Arteriosclerosis* 6: 131 (1986); Aqel, et al., *J. Pathol.* 146: 197 (1985)).

Elucidation of the primary structure of EPR-1, and identification of the functional domain(s) participating in intracellular signalling and T cell activation provides insights into this novel regulatory mechanism of lymphocyte proliferation.

Example 13

Deposit of Materials

The MOLT13 #3 cell line was deposited at the American Type Culture Collection (ATCC) 12301 Parklawn Drive, Rockville, Md., USA 20852, on Jan. 11, 1991 and received Accession Number CRL 10638. The deposit was made pursuant to, and in compliance with, all applicable provisions of the Budapest Treaty.

The hybridoma designated 12H1 was deposited on Jan. 11, 1991, at the ATCC pursuant to, and in compliance with, all applicable provisions of the Budapest Treaty. The hybridoma was given the designation ATCC HB 10637.

Hybridoma 2E1 was deposited on Jan. 27, 1994 at the ATCC pursuant to, and in compliance with, all applicable provisions of the Budapest Treaty. The hybridoma was given the designation ATCC HB 11536.

The aforementioned deposits were made in compliance with the Budapest Treaty requirements that the duration of the deposits should be for 30 years from the date of deposit or for 5 years after the last request for the deposit at the depository or for the enforceable life of a U.S. patent that matures from this application, whichever is longer. The deposited cell line and hybridomas will be replenished should it become non-viable at the depository.

While the present invention is described in some detail by way of illustration and example for purposes of clarity, certain obvious modifications can be practiced within the scope of the appended claims. One skilled in the art will readily appreciate that various modifications, changes, omissions and substitutions may be made without departing from the spirit thereof.

We claim:

1. A diagnostic method useful in identifying chronic lymphocytic leukemia (CLL) in a human subject characterized by increased EPR-1 expression on CD5 positive cells, comprising the steps of:
   a. obtaining a cell-containing vascular fluid test sample from a human subject;
   b. admixing said test sample with an antibody molecule that specifically binds EPR-1;
   c. maintaining said admixture under biological assay conditions for a time period sufficient for any CD5 positive cells simultaneously co-expressing EPR-1 to immunoreact with said antibody molecule to form an immunoreaction product;
   d. separating said immunoreaction product from any unreacted antibody molecules present in said admixture;
   e. determining the presence of immunoreaction product formed thereby;
   f. correlating the amount of product detected in step e with the amount of EPR-1 expressed by said cells to ascertain the level of EPR-1 expression; and
   g. comparing the level of EPR-1 expression in said test sample with the level of EPR-1 expression ascertained from a normal human control sample, thereby determining whether the subject has CLL.

2. The method of claim 1, wherein said antibody molecule comprises an immunoglobulin molecule or an immunologically active fragment thereof.

3. The method of claim 1, wherein said fragment is selected from the group consisting of Fab, Fab', F(ab')$_2$ and F$_v$.

4. The method of claim 1, wherein said antibody molecule includes an antibody combining site that specifically binds an EPR-1 protein, but which does not specifically bind factor V.

5. The method of claim 1, wherein said antibody is produced by a hybridoma having ATCC No. HB 10637.

6. The method of claim 1, wherein said antibody molecule is labeled.

7. The method of claim 1, wherein said antibody molecule is affixed to a solid support.

8. The method of claim 1, wherein increased EPR-1 expression is an increase in the number of EPR-1 molecules on the cell surface.

9. The method of claim 1, wherein increased EPR-1 expression is an increase in the number cells expressing both EPR-1 and CD5 molecules.

10. A diagnostic method useful in the characterization of chronic lymphocytic leukemia (CLL) characterized by increased EPR-1 expression, comprising the steps of:
   a. obtaining a cell-containing vascular fluid test sample from a human subject;
   b. admixing said test sample with an antibody molecule that specifically binds EPR-1, wherein said antibody is produced by a hybridoma having ATCC No. HB 11536;
   c. maintaining said admixture under biological assay conditions for a time period sufficient for any cells expressing EPR-1 to immunoreact with said antibody molecule to form an immunoreaction product;
   d. separating said immunoreaction product from any unreacted antibody molecules present in said admixture;
   e. determining the presence of immunoreaction product formed thereby;
   f. correlating the amount of product detected in step e with the amount of EPR-1 expressed by said cells to ascertain the level of EPR-1 expression; and
   g. comparing the level of EPR-1 expression in said test sample with the level of EPR-1 expression ascertained from a normal human control sample, thereby determining whether the presence of CLL is indicated in said test sample.

11. The method of claim 10, wherein said antibody molecule is labeled.

12. The method of claim 10, wherein said antibody molecule is affixed to a solid support.

13. The method of claim 10, wherein said antibody molecule comprises an immunoglobulin molecule or an immunologically active fragment thereof.

14. The method of claim 13, wherein said fragment is selected from the group consisting of Fab, Fab', F(ab')$_2$ and F$_v$.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
    (A) LENGTH: 1165 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (ix) FEATURE:
    (A) NAME/KEY: CDS
    (B) LOCATION: 37..1047

(xi) SEQUENCE DESCRIPTION: SEQ ID NO:1:

```
AAATGACAGG CTTTTTATTT CTCAGGAACA GCCGAG ATG ACC TCC AGA GGT TTC           54
                                        Met Thr Ser Arg Gly Phe
                                         1               5

CAG CGA AGC TGT AAC AAT CCA CCC TGC AGC TCT ATG ACA GGG AGG AGG           102
Gln Arg Ser Cys Asn Asn Pro Pro Cys Ser Ser Met Thr Gly Arg Arg
            10              15                  20

GCG AAT CAA ATC CAT CAT CTT ACG CCA GAC TTC AGC CTG CGG GAG CTG           150
Ala Asn Gln Ile His His Leu Thr Pro Asp Phe Ser Leu Arg Glu Leu
        25              30                  35

CTG CCT CCA AAG AAA GCG GGG ACC TGG GCG GAC TGC GTC TCT CCC CCG           198
Leu Pro Pro Lys Lys Ala Gly Thr Trp Ala Asp Cys Val Ser Pro Pro
    40              45                  50

TGT GGA GAA CGT GAC AGA TGT GAA GGT TGG GCT GAC AGA CAC ACG GCC           246
Cys Gly Glu Arg Asp Arg Cys Glu Gly Trp Ala Asp Arg His Thr Ala
 55              60                  65                  70

TGC AGC AGC CCA GCC AGC ACC TGC CAA GTC CAC ACT CAG GAC TGT GAC           294
Cys Ser Ser Pro Ala Ser Thr Cys Gln Val His Thr Gln Asp Cys Asp
                75                  80                  85

AGC CTC AAC AAC ATG AGG TCC AGA CAC ATT CAC TGT GGA AGG CTC TGC           342
Ser Leu Asn Asn Met Arg Ser Arg His Ile His Cys Gly Arg Leu Cys
                    90                  95                 100

CAC GCG AAC AAA GCT GTC AGC TCT AGC AAA AGG GAC ACT GCC TTC TTC           390
His Ala Asn Lys Ala Val Ser Ser Ser Lys Arg Asp Thr Ala Phe Phe
            105                 110                 115

CTC CCT CAC TTC TCA CCT GGT AAG CCC GGG AAT CAA AAC AGC AAA AAT           438
Leu Pro His Phe Ser Pro Gly Lys Pro Gly Asn Gln Asn Ser Lys Asn
    120                 125                 130

GAG CCC CCA AAA AAG AGA GAG AGA GAG AGC AGC CAC TGT TAC CCA               486
Glu Pro Pro Lys Lys Arg Glu Arg Glu Arg Ser Ser His Cys Tyr Pro
135                 140                 145                 150

GCA GCA CCC GCT GCA CAG GCA GAA GCA CCT CTG GTG CCA CTT TCA AGA           534
Ala Ala Pro Ala Ala Gln Ala Glu Ala Pro Leu Val Pro Leu Ser Arg
                155                 160                 165

CAA AAC AAG AGC ACA GTT GAA ACA TCT AAT TTG AAA ATG TTG ATC TCC           582
Gln Asn Lys Ser Thr Val Glu Thr Ser Asn Leu Lys Met Leu Ile Ser
                170                 175                 180

TTT CCT AAG ACA TTG CTA AGG GGC CCA CAG GAA GGC TGG TGG CAC CAG           630
Phe Pro Lys Thr Leu Leu Arg Gly Pro Gln Glu Gly Trp Trp His Gln
            185                 190                 195

GGA ATA AAC CCT GGA AGT GGT GCA GCC ACT CTG GGA CCA GGC AGC TCC           678
Gly Ile Asn Pro Gly Ser Gly Ala Ala Thr Leu Gly Pro Gly Ser Ser
        200                 205                 210

GAG AGG CCT CAA TCC ATC GAG GCC AGC TGC TCG ATG GCA CGG CGC ACT           726
Glu Arg Pro Gln Ser Ile Glu Ala Ser Cys Ser Met Ala Arg Arg Thr
215                 220                 225                 230
```

```
TTC TTC GCA GTT TCC TCA AAT TCT TTC TTC TTA TTG TTG GTT TCC TTT        774
Phe Phe Ala Val Ser Ser Asn Ser Phe Phe Leu Leu Leu Val Ser Phe
                235                 240                 245

GCA ATT TTG TTC TTG GCT CTT TCT CTG TCC AGT TTC AAA AAT TCA CCA        822
Ala Ile Leu Phe Leu Ala Leu Ser Leu Ser Ser Phe Lys Asn Ser Pro
            250                 255                 260

AGG GTT AAT TCT TCA AAC TGC TTC TTG ACA GAA AGG AAA GCG CAA CCG        870
Arg Val Asn Ser Ser Asn Cys Phe Leu Thr Glu Arg Lys Ala Gln Pro
                265                 270                 275

GAC GAA TGC TTT TTA TGT TCC TCT ATG GGG TCG TCA TCT GGC TCC CAG        918
Asp Glu Cys Phe Leu Cys Ser Ser Met Gly Ser Ser Ser Gly Ser Gln
            280                 285                 290

CCT TCC AGC TCC TTG AAG CAG AAG AAA CAC TGG GCC AAG TCT GGC TCG        966
Pro Ser Ser Ser Leu Lys Gln Lys Lys His Trp Ala Lys Ser Gly Ser
295                 300                 305                 310

TTC TCA GTG GGG CAG TGG ATG AAG CCA GCC TCG GCC ATC CGC TCC GGG       1014
Phe Ser Val Gly Gln Trp Met Lys Pro Ala Ser Ala Ile Arg Ser Gly
                315                 320                 325

GTG CAG CGC AGC CCT CCA AGA AGG GCC AGT TCT TGAATGTAGA GATGCGGTGG     1067
Val Gln Arg Ser Pro Pro Arg Arg Ala Ser Ser
                330                 335

TCCTTGAGAA AGGGCTGCCA GGCAGGGGGC AACGTCGGGG CACCCATGCC GCCGCCGCCA     1127

CCTCTGCCAA CGGGTCCGGC GATTCAAATC TGAGACAG                            1165

(2) INFORMATION FOR SEQ ID NO:2:

(i) SEQUENCE CHARACTERISTICS:
         (A) LENGTH: 337 amino acids
         (B) TYPE: amino acid
         (D) TOPOLOGY: linear (ii) MOLECULE TYPE: protein (xi) SEQUENCE DESCRIPTION: SEQ ID NO:2:

Met Thr Ser Arg Gly Phe Gln Arg Ser Cys Asn Asn Pro Pro Cys Ser
  1               5                  10                  15

Ser Met Thr Gly Arg Arg Ala Asn Gln Ile His His Leu Thr Pro Asp
                 20                  25                  30

Phe Ser Leu Arg Glu Leu Leu Pro Pro Lys Lys Ala Gly Thr Trp Ala
             35                  40                  45

Asp Cys Val Ser Pro Pro Cys Gly Glu Arg Asp Arg Cys Glu Gly Trp
         50                  55                  60

Ala Asp Arg His Thr Ala Cys Ser Ser Pro Ala Ser Thr Cys Gln Val
 65                  70                  75                  80

His Thr Gln Asp Cys Asp Ser Leu Asn Asn Met Arg Ser Arg His Ile
                 85                  90                  95

His Cys Gly Arg Leu Cys His Ala Asn Lys Ala Val Ser Ser Ser Lys
            100                 105                 110

Arg Asp Thr Ala Phe Phe Leu Pro His Phe Ser Pro Gly Lys Pro Gly
        115                 120                 125

Asn Gln Asn Ser Lys Asn Glu Pro Pro Lys Lys Arg Glu Arg Glu Arg
    130                 135                 140

Ser Ser His Cys Tyr Pro Ala Ala Pro Ala Ala Gln Ala Glu Ala Pro
145                 150                 155                 160

Leu Val Pro Leu Ser Arg Gln Asn Lys Ser Thr Val Glu Thr Ser Asn
                165                 170                 175

Leu Lys Met Leu Ile Ser Phe Pro Lys Thr Leu Leu Arg Gly Pro Gln
            180                 185                 190
```

```
Glu Gly Trp Trp His Gln Gly Ile Asn Pro Ser Gly Ala Ala Thr
            195                 200                 205

Leu Gly Pro Gly Ser Ser Glu Arg Pro Gln Ser Ile Glu Ala Ser Cys
            210                 215                 220

Ser Met Ala Arg Arg Thr Phe Phe Ala Val Ser Ser Asn Ser Phe Phe
225                 230                 235                 240

Leu Leu Leu Val Ser Phe Ala Ile Leu Phe Leu Ala Leu Ser Leu Ser
                245                 250                 255

Ser Phe Lys Asn Ser Pro Arg Val Asn Ser Ser Asn Cys Phe Leu Thr
            260                 265                 270

Glu Arg Lys Ala Gln Pro Asp Glu Cys Phe Leu Cys Ser Ser Met Gly
            275                 280                 285

Ser Ser Ser Gly Ser Gln Pro Ser Ser Ser Leu Lys Gln Lys Lys His
            290                 295                 300

Trp Ala Lys Ser Gly Ser Phe Ser Val Gly Gln Trp Met Lys Pro Ala
305                 310                 315                 320

Ser Ala Ile Arg Ser Gly Val Gln Arg Ser Pro Pro Arg Arg Ala Ser
                325                 330                 335

Ser
```

(2) INFORMATION FOR SEQ ID NO:3:

(i) SEQUENCE CHARACTERISTICS:
        (A) LENGTH: 29 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:3:

```
Ala Asp Cys Val Ser Pro Pro Cys Gly Glu Arg Asp Arg Cys Glu Gly
1               5                   10                  15

Trp Ala Asp Arg His Thr Ala Cys Ser Ser Pro Ala Ser
            20                  25
```

(2) INFORMATION FOR SEQ ID NO:4:

(i) SEQUENCE CHARACTERISTICS:
        (A) LENGTH: 427 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:4:

```
Val Leu His Lys Ser Asn Glu Thr Ser Leu Pro Thr Asp Leu Asn Gln
1               5                   10                  15

Thr Leu Pro Ser Met Asp Phe Gly Trp Ile Ala Ser Leu Pro Asp His
            20                  25                  30

Asn Gln Asn Ser Ser Asn Asp Thr Gly Gln Ala Ser Cys Pro Pro Gly
            35                  40                  45

Leu Tyr Gln Thr Val Pro Pro Glu Glu His Tyr Gln Thr Phe Pro Ile
        50                  55                  60

Gln Asp Pro Asp Gln Met His Ser Thr Ser Asp Pro Ser His Arg Ser
65                  70                  75                  80
```

```
Ser Ser Pro Glu Leu Ser Glu Met Leu Glu Tyr Asp Arg Ser His Lys
                85                  90                  95

Ser Phe Pro Thr Asp Ile Ser Gln Met Ser Pro Ser Ser Glu His Glu
            100                 105                 110

Val Trp Gln Thr Val Ile Ser Pro Asp Leu Ser Gln Val Thr Leu Ser
            115                 120                 125

Pro Glu Leu Ser Gln Thr Asn Leu Ser Pro Asp Leu Ser His Thr Thr
        130                 135                 140

Leu Ser Pro Glu Leu Ile Gln Arg Asn Leu Ser Pro Ala Leu Gly Gln
145                 150                 155                 160

Met Pro Ile Ser Pro Asp Leu Ser His Thr Thr Leu Ser Pro Asp Leu
                165                 170                 175

Ser His Thr Thr Leu Ser Leu Asp Leu Ser Gln Thr Asn Leu Ser Pro
            180                 185                 190

Glu Leu Ser Gln Thr Asn Leu Ser Pro Ala Leu Gly Gln Met Pro Leu
        195                 200                 205

Ser Pro Asp Leu Ser His Thr Thr Leu Ser Leu Asp Phe Ser Gln Thr
        210                 215                 220

Asn Leu Ser Pro Glu Leu Ser His Met Thr Leu Ser Pro Glu Leu Ser
225                 230                 235                 240

Gln Thr Asn Leu Ser Pro Ala Leu Gly Gln Met Pro Ile Ser Pro Asp
                245                 250                 255

Leu Ser His Thr Thr Leu Ser Leu Asp Phe Ser Gln Thr Asn Leu Ser
            260                 265                 270

Pro Glu Leu Ser Gln Thr Asn Leu Ser Pro Ala Leu Gly Gln Met Pro
        275                 280                 285

Leu Ser Pro Asp Pro Ser His Thr Thr Leu Ser Leu Asp Leu Ser Gln
        290                 295                 300

Thr Asn Leu Ser Pro Glu Leu Ser Gln Thr Asn Leu Ser Pro Asp Leu
305                 310                 315                 320

Ser Glu Met Pro Leu Phe Ala Asp Leu Ser Gln Ile Pro Leu Thr Pro
                325                 330                 335

Asp Leu Asp Gln Met Thr Leu Ser Pro Asp Leu Gly Glu Thr Asp Leu
            340                 345                 350

Ser Pro Asn Phe Gly Gln Met Ser Leu Ser Pro Asp Leu Ser Gln Val
            355                 360                 365

Thr Leu Ser Pro Asp Ile Ser Asp Thr Thr Leu Leu Pro Asp Leu Ser
        370                 375                 380

Gln Ile Ser Pro Pro Asp Leu Asp Gln Ile Phe Tyr Pro Ser Glu
385                 390                 395                 400

Ser Ser Gln Ser Leu Leu Leu Gln Glu Phe Asn Glu Ser Phe Pro Tyr
                405                 410                 415

Pro Asp Leu Gly Gln Met Pro Ser Pro Ser Ser
            420                 425
```

(2) INFORMATION FOR SEQ ID NO:5:

(i) SEQUENCE CHARACTERISTICS:
        (A) LENGTH: 439 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:5:

-continued

```
Val Val Gly Lys Gly Glu Phe Thr Lys Asp Val Gly Leu Lys Glu Met
 1               5                  10                 15

Val Phe Pro Ser Ser Arg Asn Leu Phe Leu Thr Asn Leu Asp Asn Leu
            20                  25                  30

His Glu Asn Asn Thr His Asn Gln Glu Lys Lys Ile Gln Glu Glu Ile
            35                  40                  45

Glu Lys Lys Glu Thr Leu Ile Gln Glu Asn Val Val Leu Pro Gln Ile
 50                  55                  60

His Thr Val Thr Gly Thr Lys Asn Phe Met Lys Asn Leu Phe Leu Leu
 65                  70                  75                  80

Ser Thr Arg Gln Asn Val Glu Gly Ser Tyr Asp Gly Ala Tyr Ala Pro
            85                  90                  95

Val Leu Gln Asp Phe Arg Ser Leu Asn Asp Ser Thr Asn Arg Thr Lys
            100                 105                 110

Lys His Thr Ala His Pro Ser Lys Lys Gly Glu Glu Asn Leu Glu
            115                 120                 125

Gly Leu Gly Asn Gln Thr Lys Gln Ile Val Glu Lys Tyr Ala Cys Thr
            130                 135                 140

Thr Arg Ile Ser Pro Asn Thr Ser Gln Gln Asn Phe Val Thr Gln Arg
145                 150                 155                 160

Ser Lys Arg Ala Leu Lys Gln Phe Arg Leu Pro Leu Glu Glu Thr Glu
            165                 170                 175

Leu Glu Lys Arg Ile Ile Val Asp Asp Thr Ser Thr Gln Trp Ser Lys
            180                 185                 190

Asn Met Lys His Leu Thr Pro Ser Thr Leu Thr Gln Ile Asp Tyr Asn
            195                 200                 205

Glu Lys Glu Lys Gly Ala Ile Thr Gln Ser Pro Leu Ser Asp Cys Leu
210                 215                 220

Thr Arg Ser His Ser Ile Pro Gln Ala Asn Arg Ser Pro Leu Pro Ile
225                 230                 235                 240

Ala Lys Val Ser Ser Phe Pro Ser Ile Arg Pro Ile Tyr Leu Thr Arg
            245                 250                 255

Val Leu Phe Gln Asp Asn Ser Ser His Leu Pro Ala Ala Ser Tyr Arg
            260                 265                 270

Lys Lys Asp Ser Gly Val Gln Glu Ser Ser His Phe Leu Gln Gly Ala
            275                 280                 285

Lys Lys Asn Asn Leu Ser Leu Ala Ile Leu Thr Leu Glu Met Thr Gly
            290                 295                 300

Asp Gln Arg Glu Val Gly Ser Leu Gly Thr Ser Ala Thr Asn Ser Val
305                 310                 315                 320

Thr Tyr Lys Lys Val Glu Asn Thr Val Leu Pro Lys Pro Asp Leu Pro
            325                 330                 335

Lys Thr Ser Gly Lys Val Glu Leu Leu Pro Lys Val His Ile Tyr Gln
            340                 345                 350

Lys Asp Leu Phe Pro Thr Glu Thr Ser Asn Gly Ser Pro Gly His Leu
            355                 360                 365

Asp Leu Val Glu Gly Ser Leu Leu Gln Gly Thr Glu Gly Ala Ile Lys
            370                 375                 380

Trp Asn Glu Ala Asn Arg Pro Gly Lys Val Pro Phe Leu Arg Val Ala
385                 390                 395                 400

Thr Glu Ser Ser Ala Lys Thr Pro Ser Lys Leu Leu Asp Pro Leu Ala
            405                 410                 415
```

```
-continued

Trp Asp Asn His Tyr Gly Thr Gln Ile Pro Lys Glu Glu Trp Lys Ser
        420                 425                 430

Gln Glu Lys Ser Pro Glu Lys
        435
```